US006667303B1

(12) United States Patent
Gu et al.

(10) Patent No.: US 6,667,303 B1
(45) Date of Patent: Dec. 23, 2003

(54) ARYL SUBSTITUTED 1,4-DIAZEPANES AND METHOD OF USE THEREOF

(75) Inventors: Yansong Gu, Pearl River, NY (US); Jeffrey Claude Pelletier, Lafayette Hill, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/208,561

(22) Filed: Jul. 30, 2002

Related U.S. Application Data
(60) Provisional application No. 60/308,645, filed on Jul. 30, 2001, provisional application No. 60/308,650, filed on Jul. 30, 2001, and provisional application No. 60/308,658, filed on Jul. 30, 2001.

(51) Int. Cl.$^7$ .................. C07D 243/08; C07D 405/00; C07D 403/00; A61K 31/55; A61P 25/24
(52) U.S. Cl. ...................... 514/212.01; 514/217.03; 514/217.08; 514/217.09; 514/217.1; 514/218; 540/575; 540/596; 540/602; 540/603
(58) Field of Search ................ 540/575, 596, 540/602, 603; 514/212.01, 217.03, 217.08, 217.09, 217.1, 218

(56) References Cited

FOREIGN PATENT DOCUMENTS

| EP | 0 556 889 | 8/1993 |
|---|---|---|
| WO | WO 99/32461 | 7/1999 |

OTHER PUBLICATIONS

S. Rosenzweig–Lipson et al., The FASEB Journal, 14, A1321 (2000).
Katsunori Nonogaki et al., Nature Medicine, 4(10), 1152–1156 (1998).
P.A. Sargent et al., Psychopharmacology, 133, 309–312 (1997).
Laurence H. Tecott et al., Nature, 374, 542–546 (1995).
M.J. Piesla et al., International Congress on Schizophrenia Research (2001).
Craig D. Applegate et al., Experimental Neurology, 154, 522–530 (1998).
Mark J. Millan et al., European Journal of Pharmacology, 325, 9–12 (1997).
Andrew J. Grottick et al., The Journal of Pharmacology & Experimental Therapeutics, 295(3), 1183–1191 (2000).
Duckhyun Kim et al., Experimental Neurology, 169, 496–500 (2001).
Roger M. Nitsch et al., The Journal of Biological Chemistry, 271(8), 4188–4194 (1996).
J.R. Martin et al., The Journal of Pharmacology & Experimental Therapeutics, 286, 913–924 (1998).
Marie–Christine Buhot, Current Opinion in Neurobiology, 7, 243–254 (1997).
Yuhao Li et al., European Journal of Pharmacology, 392, 71–77 (2000).
Jotaro Akiyoshi et al., Biol. Psychiatry, 39, 1000–1008, 1996.
Oliver Lowry et al., J. Biol. Chem., 193, 265–275, 1951.
Elaine Sanders–Bush et al., The Journal of Pharmacology & Experimental Therapeutics, 247(1), 169–173, 1988.

*Primary Examiner*—Bruck Kifle
(74) *Attorney, Agent, or Firm*—Kimberly R. Hild

(57) ABSTRACT

Aryl substituted 1,4-diazepanes are provided such as derivatives of 6-(1,4-diazepan-1-yl)benzo[cd]indol-2(1H)-one, 6-(1,4-diazepan-1-yl)acenaphthylen-1(2H)-one and 5-(1,4-diazepan-1-yl)-2H-naphtho[1,8-cd]isothiazole-1,1-dioxide. Also provided are pharmaceutical compositions containing one or more of the aryl substituted 1,4-diazepanes. The aryl substituted 1,4-diazepanes are useful for treating disorders or deficiencies associated with the 5-HT2C receptor.

54 Claims, No Drawings

ARYL SUBSTITUTED 1,4-DIAZEPANES AND METHOD OF USE THEREOF

CROSS REFERENCE TO RELATED APPLICATIONS

This application claims the benefit under 35 U.S.C. §119 (e) to U.S. provisional applications Ser. Nos.: 60/308,645, 60/308,650, and 60/308,658, all filed on Jul. 30, 2001. The disclosures of the '645, '650, and '658 provisional applications are hereby incorporated by reference in their entireties.

FIELD OF THE INVENTION

The present invention relates to aryl substituted 1,4-diazepanes having affinity at the serotonin 5-hydroxytryptamine 2C (5HT2C) receptor and functioning as agonists at that receptor. Compounds having this activity are useful for the treatment of disorders such as obsessive-compulsive disorder, depression, anxiety, schizophrenia, migraine, sleep disorders, eating disorders, sexual dysfunction, obesity, and epilepsy.

BACKGROUND TO THE INVENTION

Serotonin is localized in the central and peripheral nervous systems and is known to affect many types of conditions including psychiatric disorders, feeding behavior, sexual activity, and neuroendocrine regulation among others. 5-HT2C receptor ligands are believed to be of potential use in the treatment of certain central nervous system (CNS) disorders such as anxiety disorders such as generalized anxiety, obsessive-compulsive disorder, social phobias, and panic disorder; affective (i.e., mood) disorders such as depression, atypical depression and bipolar disorders; psychoses involving gross impairment of reality such as schizophrenia and related disorders; sleep disorders; eating disorders (e.g., anorexia, and bulimia); obesity; epilepsy; diabetes; and migraine. EP556889A1 reports the synthesis of arylpiperazines and arylhomopiperazines. WO99/32461 presents a scenario similar to EP556889A1 with the homopiperazine attached to the 1-position of the 1,2,3,4-tetrahydronaphthyl ring.

SUMMARY OF THE INVENTION

This invention relates to novel aryl substituted 1,4-diazepanes, such as derivatives of 6-(1,4-diazepan-1-yl) benzo[cd]indol-2(1H)-one, 6-(1,4-diazepan-1-yl) acenaphthylen-1 (2H)-one and 5-(1,4-diazepan-1-yl)-2H-naphtho[1,8-cd]isothiazole-1,1-dioxide; to processes for their preparation; to pharmaceutical compositions containing them and to their use in therapy. These compounds are believed to have affinity at the serotonin 5-hydroxytrptamine 2C (5HT2C) receptor and are believed to function as agonists at that receptor. Compounds having this activity are useful for the treatment of disorders such as anxiety disorders such as generalized anxiety, obsessive-compulsive disorder, social phobias, and panic disorder; affective (i.e., mood) disorders such as depression, atypical depression and bipolar disorders; psychoses involving gross impairment of reality such as schizophrenia; sleep disorders; eating disorders (e.g., anorexia and bulimia); obesity; epilepsy; diabetes; and migraine.

Compounds of this invention include those of Formula (1) or a non-toxic, pharmaceutically acceptable salt thereof Formula (I)

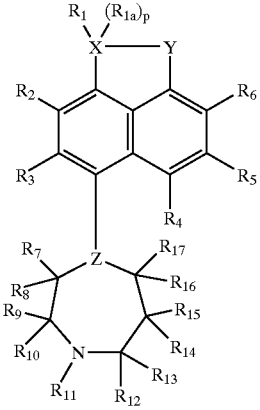

where:

X is C or N;

Y is $CH_2$, C=O, S=O, or $SO_2$;

Z is N or C;

$R_1$, $R_{1a}$ and $R_{11}$ are each independently selected from hydrogen, or an alkyl, cycloalkyl, arylalkyl, alkenyl, or heteroarylalkyl group;

$R_2$, $R_3$, $R_4$, $R_5$ and $R_6$ are each independently selected from hydrogen, halogen, or an alkyl, alkenyl, alkynyl, cycloalkyl, cycloheteroalkyl, aryl, heteroaryl, arylalkyl, alkanoyl, CN, CHO, alkoxy, aryloxy, heteroaryloxy, alkenyloxy, alkynyloxy, OCOalkyl, OCOaryl, OCONR$_{18}$, COOH, COOalkyl, COOaryl, CONR$_{18}$R$_{19}$, CONHOH, NR$_{18}$R$_{19}$, SO$_2$NR$_{18}$R$_{19}$, NO$_2$, NH$_2$, or OH group, where $R_{18}$ and $R_{19}$ are each independently selected from hydrogen, or an alkyl, alkenyl, alkynyl, aryl, heteroaryl, arylalkyl, perfluoroalkyl, COalkyl, COaryl, COheteroaryl, COOalkyl, COOaryl, COOheteroaryl, CONHalkyl, CON(alkyl)$_2$, CONHaryl, CONHheteroaryl, cycloalkyl, cycloheteroalkyl, S(O)$_m$-alkyl or S(O)$_m$-aryl group, where m is 0, 1 or 2;

$R_7$, $R_8$, $R_9$, $R_{10}$, $R_{12}$, $R_{13}$, $R_{14}$, $R_{15}$, $R_{16}$, and $R_{17}$ are each independently selected from hydrogen, or an alkyl, alkenyl, alkynyl, cycloalkyl, cycloheteroalkyl, aryl, arylalkyl or heteroaryl group; and where p is 1 when X is carbon and p is zero when X is nitrogen.

Preferred compounds of the present invention are represented by the general Formula (II) or a pharmaceutically acceptable salt thereof.

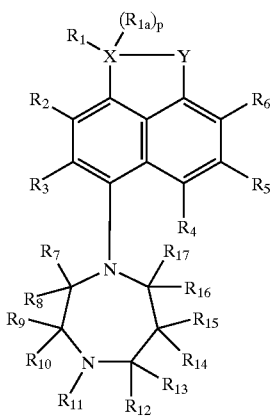

Formula (II)

where:
X is either C or N;
Y is either $CH_2$, $C(O)$ or $SO_2$;
$R_1$, $R_{1a}$, and $R_{11}$ are each independently selected from hydrogen, or an alkyl, cycloalkyl, arylalkyl, or alkenyl group; and
$R_2$, $R_3$, $R_4$, $R_5$, $R_6$, $R_7$, $R_8$, $R_9$, $R_{10}$, $R_{12}$, $R_{13}$, $R_{14}$, $R_{15}$, $R_{16}$, and $R_{17}$ are dedined as before.

A second preferred class of compounds of the present invention is represented by Formulas (III) or (IV), or a pharmaceutically acceptable salt thereof:

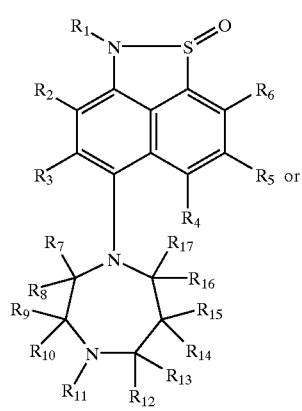

Formula (III)

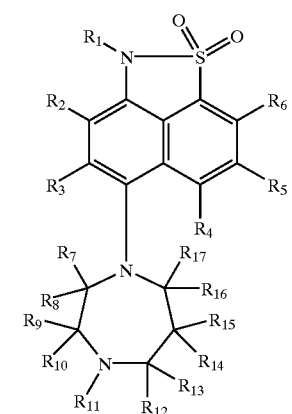

Formula (IV)

where $R_1$ and $R_{11}$ are each independently selected from hydrogen, or an alkyl, cycloalkyl, arylalkyl, alkenyl, or heteroarylalkyl group; and $R_2$, $R_3$, $R_4$, $R_5$, $R_6$, $R_7$, $R_8$, $R_9$, $R_{10}$, $R_{12}$, $R_{13}$, $R_{14}$, $R_{15}$, $R_{16}$, and $R_{17}$ are defined as before.

A third preferred class of compounds of the present invention is represenited by Formulas (V) or (VI), or a pharmaceutically acceptable salt thereof:

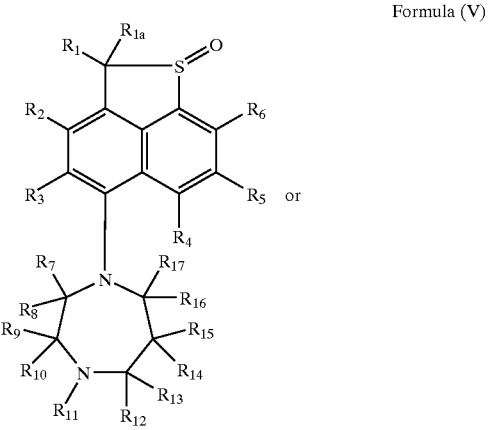

Formula (V)

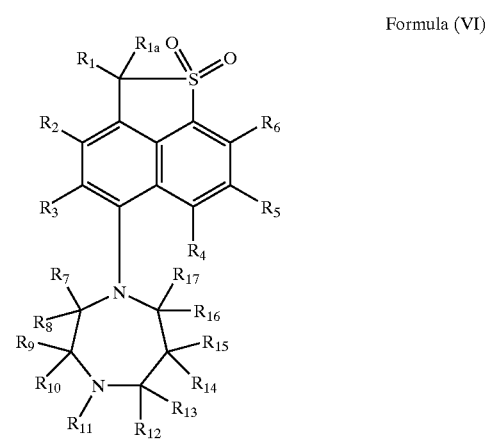

Formula (VI)

where:

$R_1$, $R_{1a}$ and $R_{11}$ are each independently selected from hydrogen, or an alkyl, cycloalkyl, arylalkyl, alkenyl, or heteroarylalkyl group; and $R_2$, $R_3$, $R_4$, $R_5$, $R_6$, $R_7$, $R_8$, $R_9$, $R_{10}$, $R_{12}$, $R_{13}$, $R_{14}$, $R_{15}$, $R_{16}$, and $R_{17}$ are defined as before.

A fourth preferred class of compounds of the present invention is represented by Formulas (VII) or (VIII), or a pharmaceutically acceptable salt thereof:

Formula (VII)

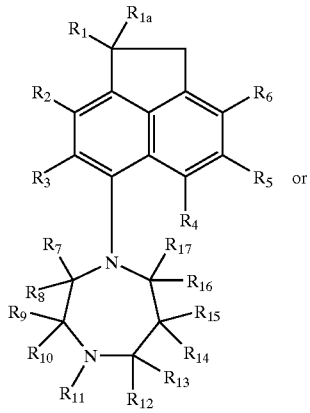

or

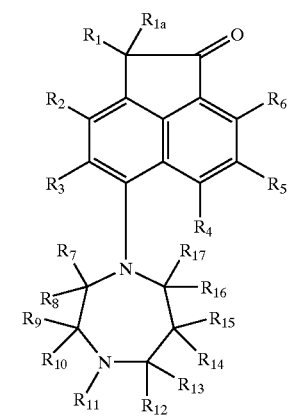

Formula (VIII)

where:

R₁, R₁ₐ and R₁₁ are each independently selected from hydrogen, or an alkyl, cycloalkyl, arylalkyl, alkenyl, or heteroarylalkyl group; and $R_2$, $R_3$, $R_4$, $R_5$, $R_6$, $R_7$, $R_8$, $R_9$, $R_{10}$, $R_{12}$, $R_{13}$, $R_{14}$, $R_{15}$, $R_{16}$, and $R_{17}$ are defined as before.

A fifth preferred class of compounds of the present invention is represented by Formulas (IX) or (X), or a pharmaceutically acceptable salt thereof Formula (IX)

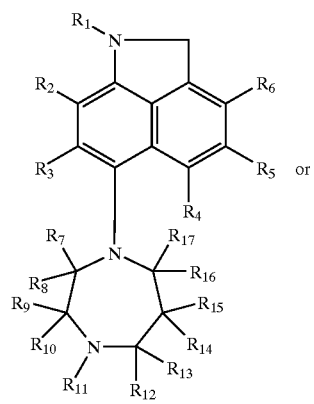

Formula (X)

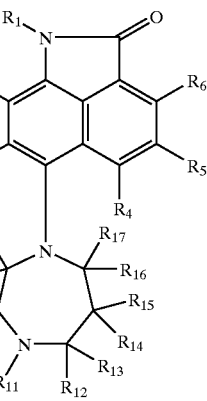

where:

$R_1$ and $R_{11}$ are each independently selected from hydrogen, or an alkyl, cycloalkyl, arylalkyl, alkenyl, or heteroarylalkyl group; and $R_2$, $R_3$, $R_4$, $R_5$, $R_6$, $R_7$, $R_8$, $R_9$, $R_{10}$, $R_{12}$, $R_{13}$, $R_{14}$, $R_{15}$, $R_{16}$, and $R_{17}$ are defined as before.

Within each of the classes of compounds of Formulas (I) through (X), it is preferred that the moiety:

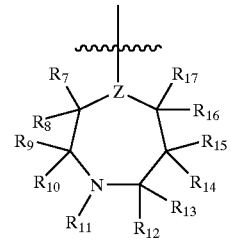

is the moiety:

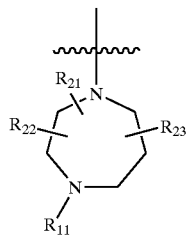

where $R_{21}$, $R_{22}$, and $R_{23}$ are each independently selected from hydrogen, or an alkyl, alkenyl, alkynyl, cycloalkyl, cycloheteroalkyl, aryl, arylalkyl or heteroaryl group, and $R_{11}$ is defined as before for each formula.

In another embodiment of Formulas (I) through (X), the variables $R_7$, $R_8$, $R_9$, $R_{10}$ $R_{12}$, $R_{13}$, $R_{14}$, $R_{15}$, $R_{16}$ and $R_{17}$ are preferably hydrogen and $R_{11}$ is defined as before for each formula.

In another embodiment of Formulas (I) through (X), the variables $R_2$, $R_3$, $R_4$, $R_5$ and $R_6$ are each hydrogen and $R_1$ and $R_7$ through $R_{17}$ are as defined before for each formula.

DETAILED DESCRIPTION OF THE INVENTION

Compounds of the invention include those of Formula (I) or a non-toxic, pharmaceutically acceptable acid addition salt thereof

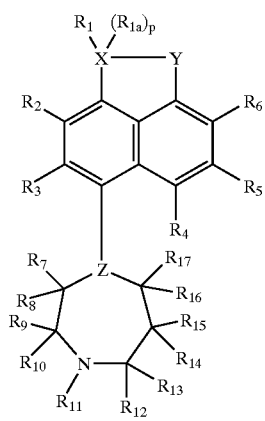

Formula (I)

where:
X is C or N;
Y is CH$_2$, C=O, S=O, or SO$_2$;
Z is C or N;
R$_1$, R$_{1a}$, and R$_{11}$ are each independently selected from hydrogen, or an alkyl, cycloalkyl, arylalkyl, alkenyl, or heteroarylalkyl group;
R$_2$, R$_3$, R$_4$, R$_5$ and R$_6$ are each independently selected from hydrogen, halogen, or an alkyl, alkenyl, alkynyl, cycloalkyl, cycloheteroalkyl, aryl, heteroaryl, arylalkyl, alkanoyl, CN, CHO, alkoxy, aryloxy, heteroaryloxy, alkenyloxy, alkynyloxy, OCOOalkyl, OCOOaryl, OCONR$_{18}$, COOH, COOalkyl, COOaryl, CONR$_{18}$R$_{19}$, CONHOH, NR$_{18}$R$_{19}$, SO$_2$NR$_{18}$R$_{19}$, NO$_2$, NH$_2$, or OH group, where R$_{18}$ and R$_{19}$ are each independently selected from hydrogen, or an alkyl, alkenyl, alkynyl, aryl, arylalkyl, heteroaryl, perfluoroalkyl, COalkyl, COaryl, COheteroaryl, COOalkyl, COOaryl, COOheteroaryl, CONHalkyl, CON(alkyl)$_2$, CONHaryl, CONHheteroaryl, cycloalkyl, cycloheteroalkyl, S(O)$_m$-alkyl or S(O)$_m$-aryl group, where m is 0, 1 or 2;
R$_7$, R$_8$, R$_9$, R$_{10}$, R$_{12}$, R$_{13}$, R$_{14}$, R$_{15}$, R$_{16}$, and R$_{17}$ are each independently selected from hydrogen, or an alkyl, alkenyl, alkynyl, cycloalkyl, cycloheteroalkyl, aryl, arylalkyl or heteroaryl group; and where p is 1 when X is carbon and p is zero when X is nitrogen.

As used in connection with Formulas (I) through (X):

"alkyl" is defined as a C$_{1-8}$ alkyl group, that may optionally be substituted with one to three groups independently selected from R$_{20}$;

"R$_{20}$" is hydrogen, halogen, or an alkyl, alkenyl, alkynyl, cycloalkyl, cycloheteroalkyl, aryl, arylalkyl, heteroaryl, alkanoyl, CN, CHO, alkoxy, aryloxy, heteroaryloxy, alkenyloxy, alkynyloxy, OCOOalkyl, OCOOaryl, OCONR$_{18}$, COOH, COOalkyl, COOaryl, CONR$_{18}$R$_{19}$, CONHOH, NR$_{18}$R$_{19}$, SO$_2$NR$_{18}$R$_{19}$, NO$_2$, NH$_2$, OH, S(O)$_m$-alkyl or S(O)$_m$-aryl group, where m is 0, 1 or 2, R$_{18}$ and R$_{19}$ are defined as in Formula (I), and the alkyl, alkenyl, alkynyl, cycloalkyl, cycloheteroalkyl, aryl, arylalkyl, heteroaryl, alkanoyl, alkoxy, aryloxy, heteroaryloxy, alkenyloxy, alkynyloxy, OCOOalkyl, OCOOaryl, COOalkyl, COOaryl, S(O)$_m$-alkyl and S(O)$_m$-aryl groups may be optionally substituted with one or more halogens (referred to hereinafter as "halogenated");

"alkenyl" is defined as a C$_{3-10}$ alkenyl group having 1 to 2 double bonds, that may be optionally substituted with one to three groups independently selected from R$_{20}$;

"alkynyl" is defined as a C$_{3-10}$ alkynyl group having 1–2 triple bonds, that may be optionally substituted with one to three groups independently selected from R$_{20}$;

"aryl" is defined as

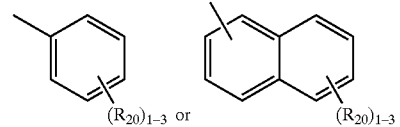

optionally substituted with one to three groups independently selected from R$_{20}$, "arylalkyl" is a type of alkyl (where one R$_{20}$ is aryl) or aryl (where one R$_{20}$ is alkyl) as defined above that contains at least one alkyl group and at least one aryl group, that may optionally be substituted on the aryl and/or alkyl portion of the arylalky with one to three groups independently selected from R$_{20}$; examples include methoxybenzyl, phenylethyl, or phenylpropyl;

"cycloalkyl" is defined as C$_{3-8}$ cycloalkyl, optionally substituted with one to three groups independently selected from R$_{20}$ such as cyclopropyl, cyclobutyl, cyclopentyl, cyclohexyl, cyclopropylmethyl, cyclobutylmethyl, cyclohexylmethyl;

"cycloheteroalkyl" is defined as

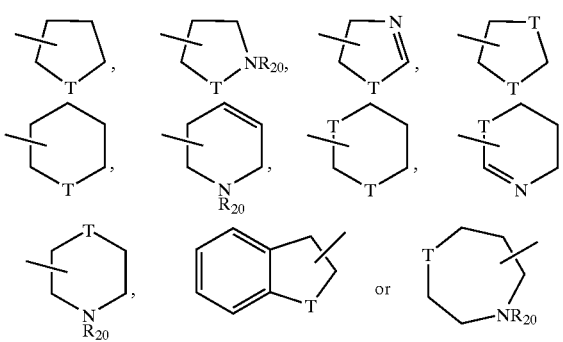

where T is defined as NR$_{18}$, O, or S (R$_{18}$ being defined the same as in Formula (I)), and where each cycloheteroalkyl group may optionally be substituted with one to six groups independently selected from R$_{20}$; it being understood that a carbon of the cycloheteroalkyl may optionally be double bonded to either O or S to form for example, a lactam or urea;

"heteroaryl" is defined as

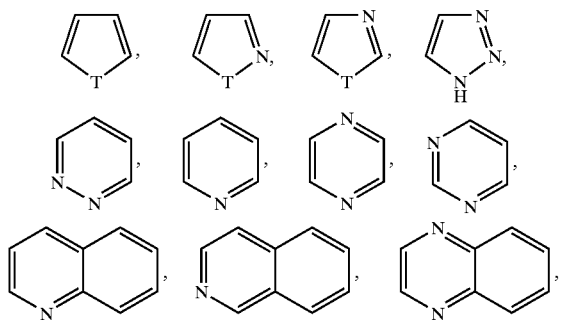

-continued

[chemical structures: benzotriazole (N-H), benzimidazole-type with T, indazole-type with T, or benzofuran-type with T]

where T is defined as before and where each heteroaryl moiety is optionally substituted with one to three groups independently selected from $R_{20}$; and "halogen" is defined as fluorine, chlorine, bromine or iodine.

"Pharmaceutically acceptable salt(s)", as used herein, are the acid addition salts which can be formed from a compound of Formulas (I) through (X) and a pharmaceutically acceptable acid such as, for example, phosphoric, sulfuric, hydrochloric, hydrobromic, citric, maleic, fumaric, acetic, lactic or methanesulfonic acid. By the term "pharmaceutically acceptable" it is meant a substance that is acceptable for use in pharmaceutical applications from a toxicological perspective and does not adversely interact with the active ingredient.

Preferred compounds include those of Formula (I) where:

Z is N;

Y is C=O or $SO_2$;

$R_1$ and $R_{1a}$ are independently selected from hydrogen, an unsubstituted linear or branched saturated $C_1$ to $C_6$ alkyl group, a $C_1$ to $C_6$ linear or branched saturated alkyl group substituted with one to three halogens, $C_1$ to $C_3$ alkoxy groups, halogenated $C_1$ to $C_3$ alkoxy groups or combinations thereof, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, a phenyl $C_1$ to $C_3$ alkyl group substituted with one to three $C_1$ to $C_3$ alkoxy groups or halogenated alkoxy $C_1$ to $C_3$ groups, or a $C_3$ to $C_{10}$ alkenyl group; and more preferably are independently selected from hydrogen, methyl, ethyl, propyl, butyl, pentyl, hexyl, trifluorobutyl, trifluoropropyl, benzyl, methoxybenzyl, phenylethyl, phenylpropyl, cyclobutyl, cyclopentyl, cyclohexyl, cyclopropylmethyl, cyclobutylmethyl, cyclohexylmethyl, or allyl;

$R_{11}$ is selected from hydrogen, an unsubstituted linear or branched saturated $C_1$ to $C_6$ alkyl group, a $C_1$ to $C_6$ linear or branched saturated alkyl group substituted with one to three halogens, $C_1$ to $C_3$ alkoxy groups, halogenated $C_1$ to $C_3$ alkoxy groups, CN, COOalkyl, COOaryl or combinations thereof, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, a phenyl $C_1$ to $C_3$ alkyl group substituted with one to three $C_1$ to $C_3$ alkoxy groups or halogenated $C_1$ to $C_3$ alkoxy groups, or a $C_3$ to $C_{10}$ alkenyl group; and more preferably is selected from hydrogen, methyl, ethyl, propyl, butyl, pentyl, hexyl, trifluorobutyl, trifluoropropyl, benzyl, methoxybenzyl, trifluoromethoxybenzyl, nitrobenzyl, phenylethyl, phenylpropyl, cyclopropylmethyl, cyclobutylmethyl, cyclohexylmethyl, cyclohexyl, allyl, methylallyl, 3,7-dimethylocta-2,6-dienyl, ethoxyethyl, cyanomethyl, cyanobutyl, ethoxycarbonylmethyl, benzyloxycarbonyl methyl;

at least two of $R_7$, $R_8$, $R_9$, $R_{10}$, $R_{12}$, $R_{13}$, $R_{14}$, $R_{15}$, $R_{16}$, and $R_{17}$ are hydrogen and more preferably each of $R_7$, $R_8$, $R_9$, $R_{10}$, $R_{12}$, $R_{13}$, $R_{14}$, $R_{15}$, $R_{16}$, and $R_{17}$ are hydrogen; or at least two of $R_2$, $R_3$, $R_4$, $R_5$ and $R_6$ are hydrogen and more preferably each of $R_2$, $R_3$, $R_4$, $R_5$ and $R_6$ are hydrogen; or any combination of the above preferred variables for Formula (I).

In another preferred embodiment of the present invention $R_1$ and $R_{1a}$ are the same when X of Formula (I) is carbon.

Preferred compounds of the present invention also include those compounds of Formulas (II) through (X) previously defined herein.

Further, with respect to Formulas (III) and (IV), in a preferred embodiment $R_1$ is hydrogen, an unsubstituted linear or branched saturated $C_1$ to $C_6$ alkyl group, a $C_1$ to $C_6$ linear or branched saturated alkyl group substituted with one to three halogens, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, a phenyl $C_1$ to $C_3$ alkyl group substituted with one to three $C_1$ to $C_3$ alkoxy groups, or a $C_3$ to $C_{10}$ alkenyl group, and more preferably methyl, ethyl, propyl, butyl, pentyl, hexyl, trifluorobutyl, trifluoropropyl, benzyl, methoxybenzyl, phenylethyl, phenylpropyl, cyclopropylmethyl, cyclobutylmethyl, cyclohexylmethyl, or allyl. $R_{11}$ is preferably hydrogen, an unsubstituted linear or branched saturated $C_1$ to $C_6$ alkyl group, a $C_1$ to $C_6$ linear or branched saturated alkyl group substituted with one to three halogens, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, a phenyl $C_1$ to $C_3$ alkyl group substituted with one to three $C_1$ to $C_3$ alkoxy groups or $C_1$ to $C_3$ halogenated alkoxy groups, or a $C_3$ to $C_{10}$ alkenyl group, and more preferably hydrogen, methyl, ethyl, propyl, butyl, pentyl, hexyl, trifluorobutyl, trifluoropropyl, benzyl, methoxybenzyl, trifluoromethoxybenzyl, nitrobenzyl, phenylethyl, phenylpropyl, cyclopropylmethyl, cyclobutylmethyl or cyclohexylmethyl.

With respect to Formulas (V), (VI), (VII) and (VIII), in a preferred embodiment $R_1$ and $R_{1a}$ are independently selected from hydrogen, an unsubstituted linear or branched saturated $C_1$ to $C_6$ alkyl group, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, or a phenyl $C_1$ to $C_3$ alkyl group substituted with one to three $C_1$ to $C_3$ alkoxy groups, and more preferably are independently selected from methyl, ethyl, propyl, butyl, pentyl, hexyl, benzyl, cyclobutyl, cyclopentyl, cyclohexyl, cyclopropylmethyl, cyclobutylmethyl, or cyclohexylmethyl. $R_{11}$ is preferably hydrogen, an unsubstituted linear or branched saturated $C_1$ to $C_6$ alkyl group, a $C_1$ to $C_6$ linear or branched saturated alkyl group substituted with one to three halogens, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, a phenyl $C_1$ to $C_3$ alkyl group substituted with one to three $C_1$ to $C_3$ alkoxy groups or $C_1$ to $C_3$ halogenated alkoxy groups, or a $C_3$ to $C_{10}$ alkenyl group, and more preferably is methyl, ethyl, propyl, butyl, pentyl, hexyl, trifluorobutyl, trifluoropropyl, benzyl, methoxybenzyl, trifluoromethoxybenzyl, nitrobenzyl, phenylethyl, phenylpropyl, cyclopropylmethyl, cyclobutylmethyl, cyclohexylmethyl, cyclohexyl, allyl, methylallyl, or 3,7-dimethylocta-2,6-dienyl.

With respect to Formulas (IX) and (X), in a preferred embodiment, $R_1$ is hydrogen, an unsubstituted linear or branched saturated $C_1$ to $C_6$ alkyl group, a $C_1$ to $C_6$ linear or branched saturated alkyl group substituted with one to three halogens, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, a phenyl $C_1$ to $C_3$ alkyl group substituted with one to three $C_1$ to $C_3$ alkoxy groups, or a $C_3$ to $C_{10}$ alkenyl group, and more preferably is methyl, ethyl, propyl, butyl, pentyl, hexyl, trifluorobutyl, trifluoropropyl, benzyl, methoxybenzyl, phenylethyl, phenylpropyl, cyclopropylmethyl, cyclobutylmethyl, cyclohexylmethyl, or allyl. $R_{11}$ is preferably hydrogen, an unsubstituted linear or branched saturated $C_1$ to $C_6$ alkyl group, a $C_1$ to $C_6$ linear or branched saturated alkyl group substituted with one to three halogens, $C_1$ to $C_3$ alkoxy groups, CN, COOalkyl, COOaryl or combinations thereof, an unsubstituted $C_3$ to $C_6$ cycloalkyl group, a $C_3$ to $C_6$ cycloalkyl group substituted with one to three $C_1$ to $C_3$ alkyl groups, an unsubstituted phenyl $C_1$ to $C_3$ alkyl group, a phenyl $C_1$ to $C_3$ alkyl group substituted with one to three $C_1$ to $C_3$ alkoxy groups or $C_1$ to $C_3$ halogenated alkoxy groups, or a $C_3$ to $C_{10}$ alkenyl group, and more preferably is methyl, ethyl, propyl, butyl, pentyl, hexyl, trifluorobutyl, trifluoropropyl, benzyl, methoxybenzyl, trifluoromethoxybenzyl, nitrobenzyl, phenylethyl, phenylpropyl, cyclopropylmethyl, cyclobutylmethyl, cyclohexylmethyl, cyclohexyl, allyl, methylallyl, 3,7-dimethylocta-2,6-dienyl, ethoxyethyl, cyanomethyl, cyanobutyl, ethoxycarbonylmethyl, or benzyloxycarbonylmethyl.

Compounds of the present invention may be prepared by those skilled in the art of organic synthesis using methods disclosed herein, which utilize readily available reagents and starting materials. While the synthesis methods disclosed herein provide specific synthesis examples, one skilled in the art of organic synthesis will be able to produce a variety of compounds falling under Formula (I), based on these synthesis examples in combination with techniques known to those skilled in organic synthesis.

The 4-(homo)piperazinyl isobenzylindoles of the present invention may be synthesized, for example, by the reaction scheme shown below.

In this reaction scheme, the reaction of isobenzoindole (2) and bromine gives the corresponding 4-bromo-isobenzoindole (3). Compound (3) can then be alkylated using different alkyl iodides to give N-alkylated 4-bromo-isobenzoindole (4). Compound (4) can in turn be coupled with (homo)piperazine or piperazine like compounds using a palladium catalyst to give the 4-piperazinyl-isobenzoisoindole (5). Alkylation of compound (5) using an alkyl iodide gives the final compound (6).

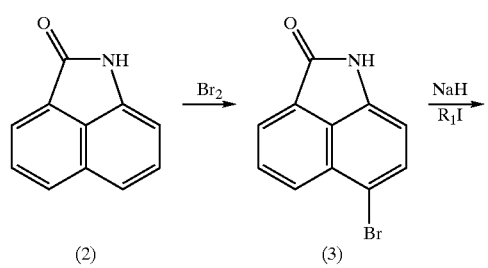

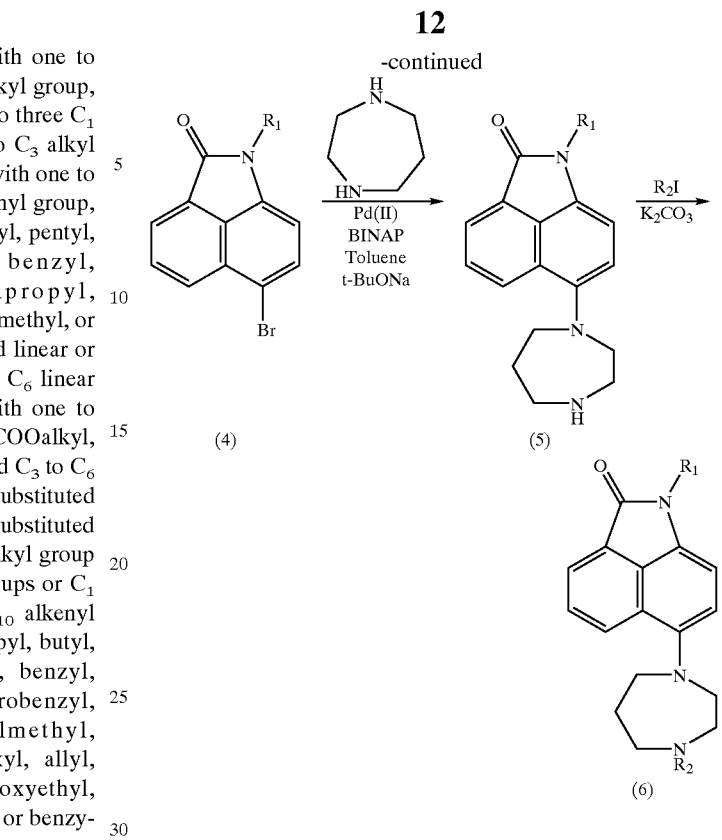

One skilled in the art would recognize that compound 6 above could, for example, be further reduced to convert the C=O moiety to $CH_2$ to produce compounds of Formula (IX).

(Homo)piperazinyl sultam derivatives may, for example, be synthesized via the reaction scheme below starting with a sultam compound (7). Alkylation of brominated sultam (8) can be carried out using Mitsunobu conditions (triphenyl phosphine, alcohol, and di-tert-butyl azodicarboxylate, i.e. DBAD).

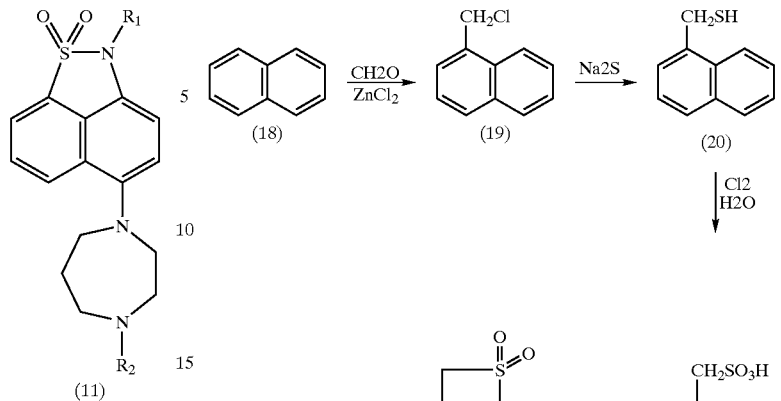

Compounds of Formula (III) could be synthesized, for example, from compound 11 above by reducing the $SO_2$ group to SH and then oxidizing SH using conventional techniques to produce S=O.

Compounds of Formula (VIII) may be synthesized, for example, via the reaction scheme shown below. In this reaction scheme below, the corresponding bromoacenaphthenone (14) is prepared from 1-α-naphthylacetic acid (12) through Friedal-Craft reaction and followed by a bromination. Compound (14) was next subjected to alkylation and palladium catalyzed amination similar to that described earlier for compound (4).

Compound (22) could then, for example, be brominated and coupled with (homo)piperazine or a piperazine like compound using a palladium catalyst in accordance with procedures previously described herein to produce a compound of Formula (VI).

Alternatively, compound (22) could be produced via the following reaction scheme and then converted to a compound of Formula (VI) as previously described.

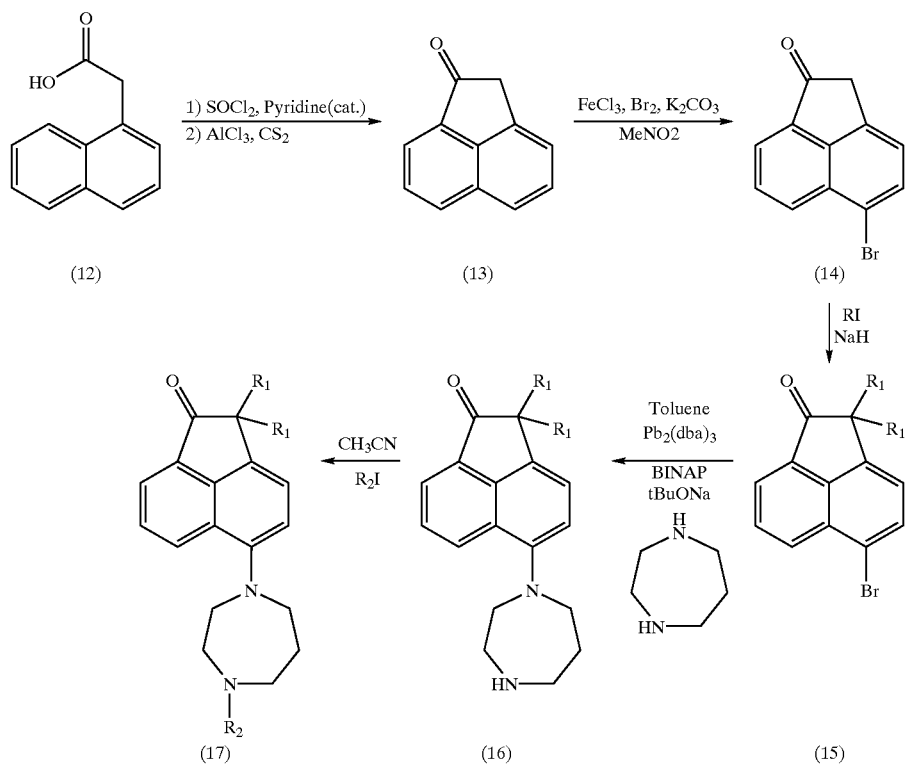

Compounds of Formula (VII) could be produced, for example, by reducing the C=O moiety of compound (17) to $CH_2$ using techniques well known to those skilled in the art.

Intermediates to compounds of Formula (VI) could be produced, for example, via the following reaction scheme:

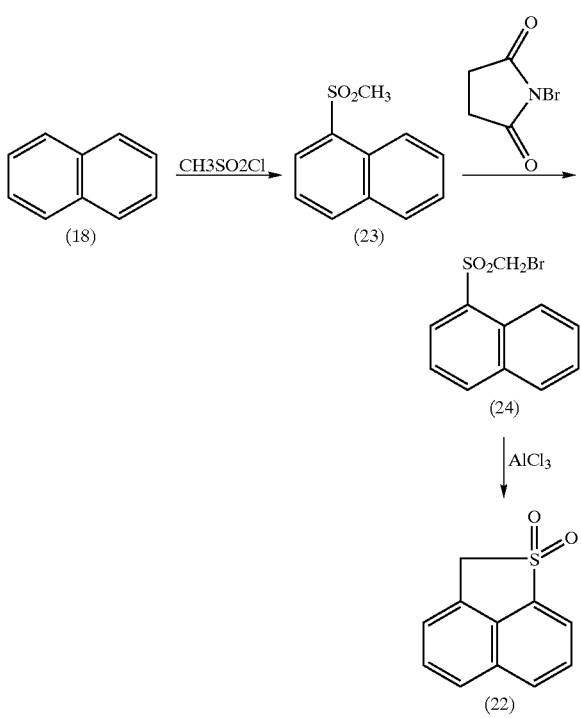

Further examples of synthesizing compounds of Formula (I) are provided hereinafter in the Examples.

The compounds of Formula (I) are 5HT2C agonists as evidenced by standard pharmacological test procedures. The 5HT2C receptor agonists of this invention are useful for the treatment or prevention in mammals, preferably in humans, of disorders involving the central nervous system. These disorders may be organic or psychological based. Examples of central nervous system disorders affected by the 5HT2C receptor include psychoses involving gross impairment of reality such as schizophrenia, schizoaffective disorder, schizophreniform disorder, or L-DOPA-induced psychosis; disorders of the personality; affective disorders (i.e., mood disorders) such as depression, atypical depression, and bipolar disorders; drug and alcohol addiction, including disorders related to withdrawal from drug or alcohol; sleep disorders (e.g., sleep apnea); eating disorders (e.g., hyperphagia, bulimia or anorexia nervosa); obesity, including consequent comorbidities such as Type II diabetes, cardiovascular disease, hypertension, hyperlipidemia, stroke, osteoarthritis, sleep apnea, gall bladder disease, gout, some cancers, some infertility, and early mortality; diabetes; intellectual deficit disorders such as dementia, Alzheimer's disease, and memory deficit; migraines; epilepsy; sexual dysfunction; and premenstrual tension. The term "disorders of the personality" as used herein are meant to include mental disorders involving inflexible and/or maladaptive personality traits and result for example in significant impairment in social functioning. Personality disorders include for example aggressivity; and anxiety disorders such as obsessive-compulsive disorder, panic disorder, generalized anxiety, and social phobias. The compounds of the present invention may be used to treat or prevent one or more of these mental disorders present in a mammal.

The present invention also includes methods of utilizing the compounds herein in treatments or preventative regimens for treatment of central nervous system deficiencies associated, for example, with trauma, stroke, spinal cord injuries, neurodegenerative diseases, toxic or infective CNS ailments including, but not limited to, encephalitis or meningitis; cardiovascular disorders such as thrombosis; or gastrointestinal disorders, such as malfunction of gastrointestinal motility. These methods include the improvement or inhibition of further degradation of central nervous system activity during or following the malady or trauma in question. Included in these improvements are maintenance or improvement in motor and motility skills, control, coordination and strength.

The present invention provides methods for treating, preventing, inhibiting or ameliorating each of these conditions, the methods comprising administering to a mammal in need thereof a pharmaceutically or therapeutically effective amount of a compound of this invention, or a pharmaceutically acceptable salt thereof. The present invention also provides a method for treating conditions related to or are affected by the 5HT2C receptor that includes administering to warm-blooded animals, including humans, an effective amount of at least one compound of the present invention or a pharmaceutically acceptable salt thereof.

A pharmaceutically or therapeutically effective amount of the compounds herein is understood to comprise an amount of the compound(s) in question which will obtain at least a minimum of desired effect in preventing, treating, inhibiting or managing the symptoms or causes of the malady in question. More preferably, the amount will be the minimum needed to alleviate or remove the undesirable physiological consequences of the malady in question and inhibit or prevent their re-occurrence.

The compounds of the present invention may be formulated into pharmaceutical compositions. These pharmaceutical compositions may be administered to mammals in accordance with the methods of the present invention.

Pharmaceutical compositions, in addition to containing a pharmaceutically effective amount of one or more compounds of the present invention, may include one or more ingredients known to those skilled in the art for formulating pharmaceutical compositions. Such ingredients include for example, carriers (e.g., in solid or liquid form), flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators. The pharmaceutical compositions may be in solid form (e.g., powder or tablet) or in liquid form.

Solid pharmaceutical compositions preferably contain one or more solid carriers, and optionally one or more other additives such as flavoring agents, lubricants, solubilizers, suspending agents, fillers, glidants, compression aids, binders or tablet-disintegrating agents or an encapsulating material. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier is preferably a finely divided solid which is in admixture with the finely divided active ingredient. In tablets, the active ingredient is mixed with a carrier having the necessary compression properties in suitable proportions, and optionally, other additives, and compacted into the desired shape and size. Solid pharmaceutical compositions, such as powders and tablets, preferably contain up to 99% of the active ingredient.

Liquid pharmaceutical compositions preferably contain one or more compounds of the present invention and one or more liquid carriers to form solutions, suspensions, emulsions, syrups or elixirs. Pharmaceutically acceptable liquid carriers include water, organic solvent, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above such as cellulose derivatives, preferably sodium carboxymethyl cellulose solution), alcohols (including monohydric alcohols and polyhydric alcohols e.g., glycols) or their derivatives, or oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be administered by, for example, intramuscular, intraperitoneal or subcutaneous injection. Sterile solutions can also be administered intravenously. Pharmaceutical compositions for oral administration may be either in liquid or solid composition form.

Preferably the pharmaceutical composition is in unit dosage form, such as tablets or capsules. In such form, the composition is sub-divided in unit dose containing appropriate quantities of the active ingredient. The unit dosage forms can be packaged compositions, for example packeted powders, vials, ampoules, pre-filled syringes or sachets containing liquids. The unit dosage form can be, for example, a capsule or tablet itself, or it can be the appropriate number of any such compositions in package form.

The pharmaceutically or therapeutically effective dosage to be used in the treatment of a specific ailment must be subjectively determined by the attending physician. The variables involved include the specific ailment, and the size, age and response pattern of the patient. The compounds may be administered orally, rectally, parenterally or topically to the skin and mucosa. The usual daily dose is depending on the specific compound, method of treatment and condition treated. The usual daily dose is 0.01–1000 mg/Kg , preferably 0.5–500 mg/Kg for oral application, and 0.1–100 mg/Kg, preferably 0.5–50 mg/Kg for parenteral application.

EXAMPLES

Compounds of the present invention were prepared and evaluated for their binding affinity to the 5HT2C receptor.

The following compounds of Formula (I) were prepared. In these examples, all chemicals and intermediates are either commercially available, can be prepared by standard procedures found in the literature, or are known to those skilled in the art of organic synthesis.

Example 1

6-[4-(3-Phenylpropyl)-1,4-diazepan-1-yl]-1-(4,4,4-trifluorobutyl) benzo[cd]indol-2(1H)-one Example 1 was prepared as shown in Scheme 1, below:

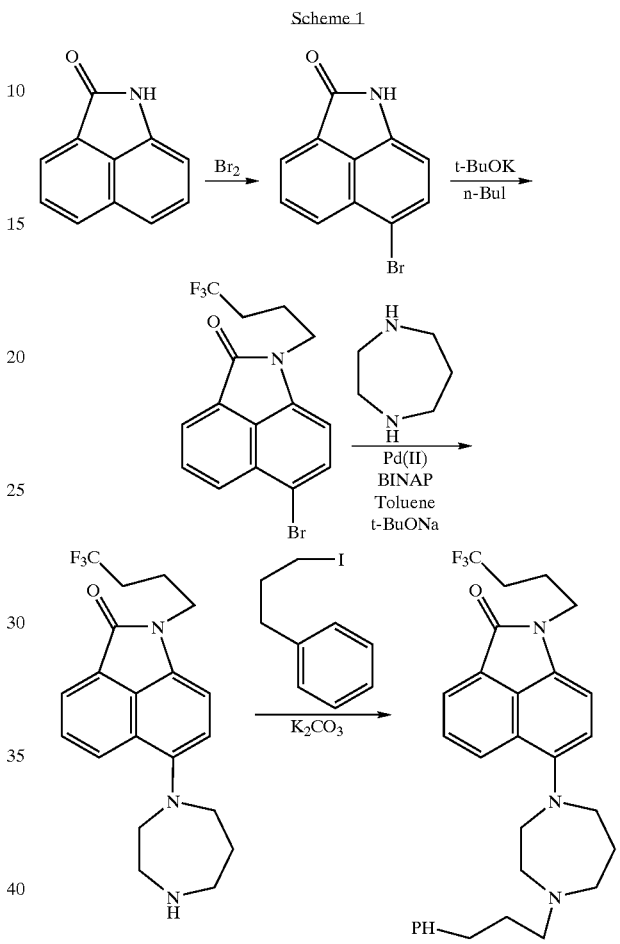

Step 1: 6-Bromo-benzo[cd]indol-2(1H)-one

Benz[cd]indol-2(1H)-one (2.1 g, 12.4 mmol) was dissolved in 50 ml trichloromethane and cooled to 0° C. To this stirred and cooled solution was added dropwise bromine (0.64 ml, 12.4 mmol) within 5 minutes. The reaction was allowed to warm up to room temperature for 24 hours. The reaction mixture was then poured into water and extracted with trichloromethane. The organic layer was dried over sodium sulfate, filtered and concentrated to give 2.935 g product (95% yield).

Step 2: 6-Bromo-1-(4,4,4-trifluorobutyl)-benzo[cd]indol-2 (1H)-one

To a solutiion of 6-bromo-benzo[cd]indol-2(1H)-one (1 g, 4 mmol) in N,N-dimethyl formamide was added $K_2CO_3$ (5.53 g, 40 mmol) and the resulting mixture was stirred for 0.5 hour under nitrogen. 4,4,4-trifluorobutyl iodide (915 mg, 4 mmol) was next injected to the solution and the mixture was heated at 60° C. for 18 hours. The reaction media was next poured into 200 ml water and extracted with trichloromethane (3×100 ml). Column chromatography using gradient ethyl acetate in hexane (10~20%) gave the desired product (1.225 g, 85%).

Step 3: 6-(1,4-Diazepan-1-yl)-1-(4,4,4-trifluorobutyl)-benzo[cd]indol-2(1H)-one

To a mixture of 1-(4,4,4-trifluorobutyl)-6-bromo-benzo[cd]indol-2(1H)-one (1.225 g, 3.42 mmol), homopiperazine (6 g, 60 mmol) and toluene (100 ml) in a round bottomed flask was added BINAP (42 mg, 2%) and $Pd_2(dba)_3$ (30 mg, 1%) and sodium tert-butoxide (333 mg, 3.46 mmol). The reaction mixture was heated at 85° C. for 18 hours and was then poured into 500 ml concentrated HCl solution in water. The organic layer was seperated and the aqueous layer was extracted with more toluene (2×500 ml). The combined organic layers were neutralized with 10 N NaOH (aqueous) and extracted with a one to one mixture of dichloromethane and toluene (3×500 ml). The combined organic layers were dried and filtered and concentrated to give the crude product (1.4 g).

Step 4: 6-[4-(3-Phenylpropyl)-1,4diazepan-1-yl]-1-(4,4,4-trifluorobutyl)benzo [cd]indol-2(1H)-one The crude product from step 3 was dissolved in 30 ml acetonitrile and distributed into 30 vials (2 ml size) pre-loaded with potassium carbonate (300 mg, 2.3 mmol). Next, 1-bromo-3-phenylporpane (135 μl, 0.135 mmol) was then added and the mixture was shaked on a robital shaker for 18 hours at room temperature. The reaction was then worked up by pipetting out most of the solution and running through a prep HPLC using the Gilson system. The product (62 mg, 54%) was obtained by stripping off the solvent on a speed-vac.

Similar compounds to Example 1 containing different $R_a$ and $R_b$ groups (see formula and Table 1 below) were synthesized by following the procedures outlined in Example 1.

TABLE 1

Isobenzoindole Compounds Synthesized and LC/MS Data (min/M + H)

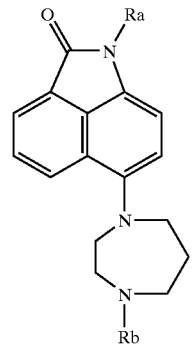

| Isobenzoindole Compound | Example No. | HPLC[1] minutes | MS[2] (M + H) |
|---|---|---|---|
| 6-[4-(3-phenylpropyl)-1,4-diazepan-1-yl]-1-(4,4,4-trifluorobutyl)benzo[cd]indol-2(1H)-one, | Example 1 | 4.72 | 496.3 |
| 6-(4-butyl-1,4-diazepan-1-yl)-1-(4-methoxybenzyl)benzo[cd]indol-2(1H)-one, | Example 2 | 4.188 | 444.3 |
| 1-(4-methoxybenzyl)-6-(4-pentyl-1,4-diazepan-1-yl)benzo[cd]indol-2(1H)-one, | Example 3 | 4.591 | 458.4 |
| 6-(4-isobutyl-1,4-diazepan-1-yl)-1-(4-methoxybenzyl)benzo[cd]indol-2(1H)-one, | Example 4 | 4.333 | 444.3 |
| 1-(4-methoxybenzyl)-6-(4-neopentyl-1,4-diazepan-1-yl)benzo[cd]indol-2(1H)-one, | Example 5 | 4.613 | 458.4 |
| 1-(4-methoxybenzyl)-6-[4-(3,3,3-trifluoropropyl)-1,4-diazepan-1-yl]benzo[cd]indol-2(1H)-one, | Example 6 | 4.351 | 484.2 |
| 1-(4-methoxybenzyl)-6-[4-(4,4,4-trifluorobutyl)-1,4-diazepan-1-yl]benzo[cd]indol-2(1H)-one, | Example 7 | 4.508 | 498.3 |
| ethyl {4-[1-(4-methoxybenzyl)-2-oxo-1,2-dihydrobenzo[cd]indol-6-yl]-1,4-diazepan-1-yl}acetate, | Example 8 | 4.243 | 474.3 |
| 1-(4-methoxybenzyl)-6-[4-(2-phenylethyl)-1,4-diazepan-1-yl]benzo[cd]indol-2(1H)-one, | Example 9 | 4.657 | 492.3 |
| 6-(4-benzyl-1,4-diazepan-1-yl)-1-(4-methoxybenzyl)benzo[cd]indol-2(1H)-one, | Example 10 | 4.507 | 478.3 |
| 1-(4-methoxybenzyl)-6-[4-(3-phenylpropyl)-1,4-diazepan-1-yl]benzo[cd]indol-2(1H)-one, | Example 11 | 4.768 | 506.3 |
| 4-{4-[1-(4-methoxybenzyl)-2-oxo-1,2-dihydrobenzo[cd]indol-6-yl]-1,4-diazepan-1-yl}butanenitrile, | Example 12 | 4.099 | 455.3 |
| 6-[4-(cyclobutylmethyl)-1,4-diazepan-1-yl]-1-(4-methoxybenzyl)benzo[cd]indol-2(1H)-one, | Example 13 | 4.438 | 456.3 |
| 6-{4-[(2E)-3,7-dimethylocta-2,6-dienyl]-1,4-diazepan-1-yl}-1-(4-methoxybenzyl)benzo[cd]indol-2(1H)-one, | Example 14 | 5.259 | 524.3 |
| 6-(4-isopentyl-1,4-diazepan-1-yl)-1-(4-methoxybenzyl)benzo[cd]indol-2(1H)-one, | Example 15 | 4.562 | 458.4 |

TABLE 1-continued

Isobenzoindole Compounds Synthesized and LC/MS Data (min/M + H)

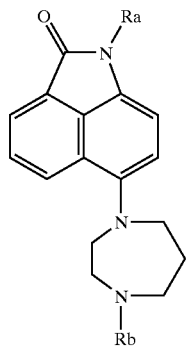

| Isobenzoindole Compound | Example No. | HPLC[1] minutes | MS[2] (M + H) |
|---|---|---|---|
| benzyl {4-[1-(4-methoxybenzyl)-2-oxo-1,2-dihydrobenzo[cd]indol-6-yl]-1,4-diazepan-1-yl}acetate, | Example 16 | 3.924 | 536.2 |
| 6-[4-(cyclopropylmethyl)-1,4-diazepan-1-yl]-1-(4-methoxybenzyl)benzo[cd]indol-2(1H)-one, | Example 17 | 4.258 | 442.3 |
| 1-(4-methoxybenzyl)-6-[4-(3-nitrobenzyl)-1,4-diazepan-1-yl]benzo[cd]indol-2(1H)-one, | Example 18 | 4.54 | 523.2 |
| 1-(cyclobutylmethyl)-6-(4-ethyl-1,4-diazepan-1-yl)benzo[cd]indol-2(1H)-one, | Example 19 | 2.51 | 364.5 |
| 1-(cyclobutylmethyl)-6-(4-propyl-1,4-diazepan-1-yl)benzo[cd]indol-2(1H)-one, | Example 20 | 2.57 | 378.45 |
| 6-(4-butyl-1,4-diazepan-1-yl)-1-(cyclobutylmethyl)benzo[cd]indol-2(1H)-one, | Example 21 | 2.68 | 392.45 |
| 6-(4-allyl-1,4-diazepan-1-yl)-1-(cyclobutylmethyl)benzo[cd]indol-2(1H)-one, | Example 22 | 2.507 | 376.45 |
| 1-(cyclobutylmethyl)-6-(4-pentyl-1,4-diazepan-1-yl)benzo[cd]indol-2(1H)-one, | Example 23 | 2.87 | 406.45 |
| 1-(cyclobutylmethyl)-6-(4-isobutyl-1,4-diazepan-1-yl)benzo[cd]indol-2(1H)-one, | Example 24 | 2.74 | 392.45 |
| 1-(cyclobutylmethyl)-6-[4-(3,3,3-trifluoropropyl)-1,4-diazepan-1-yl]benzo[cd]indol-2(1H)-one, | Example 25 | 2.75 | 432.35 |
| 1-(cyclobutylmethyl)-6-[4-(4,4,4-trifluorobutyl)-1,4-diazepan-1-yl]benzo[cd]indol-2(1H)-one, | Example 26 | 2.76 | 446.35 |
| ethyl {4-[1-(cyclobutylmethyl)-2-oxo-1,2-dihydrobenzo[cd]indol-6-yl]-1,4-diazepan-1-yl}acetate, | Example 27 | 2.59 | 422.45 |
| 1-(cyclobutylmethyl)-6-[4-(2-phenylethyl)-1,4-diazepan-1-yl]benzo[cd]indol-2(1H)-one, | Example 28 | 3 | 440.45 |
| 6-(4-benzyl-1,4-diazepan-1-yl)-1-(cyclobutylmethyl)benzo[cd]indol-2(1H)-one, | Example 29 | 2.94 | 426.45 |
| 4-{4-[1-(cyclobutylmethyl)-2-oxo-1,2-dihydrobenzo[cd]indol-6-yl]-1,4-diazepan-1-yl}butanenitrile, | Example 30 | 2.55 | 403.45 |
| 1-(cyclobutylmethyl)-6-[4-(3-phenylpropyl)-1,4-diazepan-1-yl]benzo[cd]indol-2(1H)-one, | Example 31 | 3.08 | 454.45 |
| 1-(cyclobutylmethyl)-6-[4-(cyclobutylmethyl)-1,4-diazepan-1-yl]benzo[cd]indol-2(1H)-one, | Example 32 | 2.84 | 404.45 |
| 1-(cyclobutylmethyl)-6-[4-(2-ethoxyethyl)-1,4-diazepan-1-yl]benzo[cd]indol-2(1H)-one, | Example 33 | 2.69 | 408.45 |
| 1-(cyclobutylmethyl)-6-{4-[(2E)-3,7-dimethylocta-2,6-dienyl]-1,4-diazepan-1-yl}benzo[cd]indol-2(1H)-one, | Example 34 | 3.47 | 472.45 |
| 1-(cyclobutylmethyl)-6-(4-isopentyl-1,4-diazepan-1-yl)benzo[cd]indol-2(1H)-one, | Example 35 | 2.91 | 406.45 |
| benzyl {4-[1-(cyclobutylmethyl)-2-oxo-1,2-dihydrobenzo[cd]indol-6-yl]-1,4-diazepan-1-yl}acetate, | Example 36 | 3 | 484.45 |
| 1-(cyclobutylmethyl)-6-[4-(cyclohexylmethyl)-1,4-diazepan-1-yl]benzo[cd]indol-2(1H)-one | Example 37 | 3.09 | 432.45 |
| 1-(cyclobutylmethyl)-6-[4-(cyclopropylmethyl)-1,4-diazepan-1-yl]benzo[cd]indol-2(1H)-one, | Example 38 | 2.65 | 390.45 |
| 1-(cyclobutylmethyl)-6-[4-(3-nitrobenzyl)-1,4-diazepan-1-yl]benzo[cd]indol-2(1H)-one, | Example 39 | 2.94 | 471.35 |
| 1-ethyl-6-(4-ethyl-1,4-diazepan-1-yl)benzo[cd]indol-2(1H)-one, | Example 40 | 2.12 | 324.45 |

TABLE 1-continued

Isobenzoindole Compounds Synthesized and LC/MS Data (min/M + H)

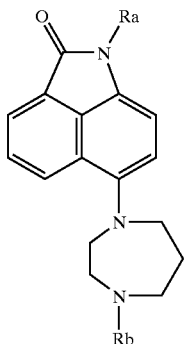

| Isobenzoindole Compound | Example No. | HPLC[1] minutes | MS[2] (M + H) |
|---|---|---|---|
| 1-ethyl-6-(4-propyl-1,4-diazepan-1-yl)benzo[cd]indol-2(1H)-one, | Example 41 | 2.238 | 338.5 |
| 6-(4-butyl-1,4-diazepan-1-yl)-1-ethylbenzo[cd]indol-2(1H)-one, | Example 42 | 2.388 | 352.45 |
| 6-(4-allyl-1,4-diazepan-1-yl)-1-ethylbenzo[cd]indol-2(1H)-one, | Example 43 | 2.216 | 336.45 |
| 1-ethyl-6-(4-pentyl-1,4-diazepan-1-yl)benzo[cd]indol-2(1H)-one, | Example 44 | 2.575 | 366.45 |
| 1-ethyl-6-(4-isobutyl-1,4-diazepan-1-yl)benzo[cd]indol-2(1H)-one, | Example 45 | 2.343 | 352.45 |
| 1-ethyl-6-[4-(3,3,3-trifluoropropyl)-1,4-diazepan-1-yl]benzo[cd]indol-2(1H)-one, | Example 46 | 2.354 | 392.35 |
| 1-ethyl-6-[4-(4,4,4-trifluorobutyl)-1,4-diazepan-1-yl]benzo[cd]indol-2(1H)-one, | Example 47 | 2.469 | 406.35 |
| ethyl [4-(1-ethyl-2-oxo-1,2-dihydrobenzo[cd]indol-6-yl)-1,4-diazepan-1-yl]acetate, | Example 48 | 2.275 | 382.45 |
| 6-(4-cyclohexyl-1,4-diazepan-1-yl)-1-ethylbenzo[cd]indol-2(1H)-one, | Example 49 | 2.551 | 378.45 |
| 1-ethyl-6-[4-(2-phenylethyl)-1,4-diazepan-1-yl]benzo[cd]indol-2(1H)-one, | Example 50 | 2.638 | 400.45 |
| 6-(4-benzyl-1,4-diazepan-1-yl)-1-ethylbenzo[cd]indol-2(1H)-one, | Example 51 | 2.996 | 386.45 |
| 4-[4-(1-ethyl-2-oxo-1,2-dihydrobenzo[cd]indol-6-yl)-1,4-diazepan-1-yl]butanenitrile, | Example 52 | 2.153 | 363.45 |
| 1-ethyl-6-[4-(3-phenylpropyl)-1,4-diazepan-1-yl]benzo[cd]indol-2(1H)-one, | Example 53 | 2.811 | 414.45 |
| 6-[4-(cyclobutylmethyl)-1,4-diazepan-1-yl]-1-ethylbenzo[cd]indol-2(1H)-one, | Example 54 | 2.463 | 364.45 |
| 6-[4-(2-ethoxyethyl)-1,4-diazepan-1-yl]-1-ethylbenzo[cd]indol-2(1H)-one, | Example 55 | 2.299 | 368.48 |
| 6-{4-[(2E)-3,7-dimethylocta-2,6-dienyl]-1,4-diazepan-1-yl}-1-ethylbenzo[cd]indol-2(1H)-one, | Example 56 | 3.168 | 432.45 |
| 1-ethyl-6-(4-isopentyl-1,4-diazepan-1-yl)benzo[cd]indol-2(1H)-one, | Example 57 | 2.546 | 366.45 |
| benzyl [4-(1-ethyl-2-oxo-1,2-dihydrobenzo[cd]indol-6-yl)-1,4-diazepan-1-yl]acetate, | Example 58 | 2.699 | 444.35 |
| 6-[4-(cyclohexylmethyl)-1,4-diazepan-1-yl]-1-ethylbenzo[cd]indol-2(1H)-one, | Example 59 | 2.729 | 392.45 |
| 6-[4-(cyclopropylmethyl)-1,4-diazepan-1-yl]-1-ethylbenzo[cd]indol-2(1H)-one, | Example 60 | 2.301 | 350.45 |
| 1-ethyl-6-[4-(3-nitrobenzyl)-1,4-diazepan-1-yl]benzo[cd]indol-2(1H)-one, | Example 61 | 2.546 | 431.35 |
| 1-isobutyl-6-(4-propyl-1,4-diazepan-1-yl)benzo[cd]indol-2(1H)-one, | Example 62 | 2.62 | 366.45 |
| 6-(4-butyl-1,4-diazepan-1-yl)-1-isobutylbenzo[cd]indol-2(1H)-one, | Example 63 | 2.76 | 380.45 |
| 6-(4-allyl-1,4-diazepan-1-yl)-1-isobutylbenzo[cd]indol-2(1H)-one, | Example 64 | 2.59 | 364.45 |
| 1-isobutyl-6-[4-(3,3,3-trifluoropropyl)-1,4-diazepan-1-yl]benzo[cd]indol-2(1H)-one, | Example 65 | 2.62 | 366.45 |
| 1-isobutyl-6-[4-(4,4,4-trifluorobutyl)-1,4-diazepan-1-yl]benzo[cd]indol-2(1H)-one, | Example 66 | 2.85 | 434.45 |
| ethyl [4-(1-isobutyl-2-oxo-1,2-dihydrobenzo[cd]indol-6-yl)-1,4-diazepan-1-yl]acetate, | Example 67 | 2.65 | 410.45 |
| 1-isobutyl-6-[4-(2-phenylethyl)-1,4-diazepan-1- | Example 68 | 2.99 | 428.45 |

TABLE 1-continued

Isobenzoindole Compounds Synthesized and LC/MS Data (min/M + H)

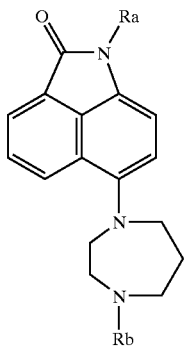

| Isobenzoindole Compound | Example No. | HPLC[1] minutes | MS[2] (M + H) |
|---|---|---|---|
| yl]benzo[cd]indol-2(1H)-one, | | | |
| 6-(4-benzyl-1,4-diazepan-1-yl)-1-isobutylbenzo[cd]indol-2(1H)-one, | Example 69 | 2.87 | 414.45 |
| 4-[4-(1-isobutyl-2-oxo-1,2-dihydrobenzo[cd]indol-6-yl)-1,4-diazepan-1-yl]butanenitrile, | Example 70 | 2.55 | 391.45 |
| 1-isobutyl-6-[4-(3-phenylpropyl)-1,4-diazepan-1-yl]benzo[cd]indol-2(1H)-one, | Example 71 | 3.1 | 442.45 |
| 6-[4-(cyclobutylmethyl)-1,4-diazepan-1-yl]-1-isobutylbenzo[cd]indol-2(1H)-one, | Example 72 | 2.82 | 392.45 |
| 6-[4-(2-ethoxyethyl)-1,4-diazepan-1-yl]-1-isobutylbenzo[cd]indol-2(1H)-one, | Example 73 | 2.69 | 396.45 |
| benzyl [4-(1-isobutyl-2-oxo-1,2-dihydrobenzo[cd]indol-6-yl)-1,4-diazepan-1-yl]acetate, | Example 74 | 3.05 | 472.35 |
| 6-[4-(cyclopropylmethyl)-1,4-diazepan-1-yl]-1-isobutylbenzo[cd]indol-2(1H)-one, | Example 75 | 2.66 | 478.45 |
| 1-isobutyl-6-[4-(3-nitrobenzyl)-1,4-diazepan-1-yl]benzo[cd]indol-2(1H)-one, | Example 76 | 2.88 | 459.35 |
| 6-(4-ethyl-1,4-diazepan-1-yl)-1-(4,4,4-trifluorobutyl)benzo[cd]indol-2(1H)-one, | Example 77 | 3.99 | 406.3 |
| 6-(4-propyl-1,4-diazepan-1-yl)-1-(4,4,4-trifluorobutyl)benzo[cd]indol-2(1H)-one, | Example 78 | 4.11 | 420.3 |
| 6-(4-allyl-1,4-diazepan-1-yl)-1-(4,4,4-trifluorobutyl)benzo[cd]indol-2(1H)-one, | Example 79 | 4.7 | 418.3 |
| 6-(4-pentyl-1,4-diazepan-1-yl)-1-(4,4,4-trifluorobutyl)benzo[cd]indol-2(1H)-one, | Example 80 | 4.54 | 448.3 |
| 6-(4-isobutyl-1,4-diazepan-1-yl)-1-(4,4,4-trifluorobutyl)benzo[cd]indol-2(1H)-one, | Example 81 | 4.27 | 434.3 |
| 1-(4,4,4-trifluorobutyl)-6-[4-(3,3,3-trifluoropropyl)-1,4-diazepan-1-yl]benzo[cd]indol-2(1H)-one, | Example 82 | 4.29 | 474.2 |
| 1-(4,4,4-trifluorobutyl)-6-[4-(4,4,4-trifluorobutyl)-1,4-diazepan-1-yl]benzo[cd]indol-2(1H)-one, | Example 83 | 4.42 | 488.2 |
| ethyl {4-[2-oxo-1-(4,4,4-trifluorobutyl)-1,2-dihydrobenzo[cd]indol-6-yl]-1,4-diazepan-1-yl}acetate, | Example 84 | 4.18 | 464.3 |
| 6-[4-(2-phenylethyl)-1,4-diazepan-1-yl]-1-(4,4,4-trifluorobutyl)benzo[cd]indo-2(1H)-one, | Example 85 | 4.59 | 482.3 |
| 6-(4-benzyl-1,4-diazepan-1-yl)-1-(4,4,4-trifluorobutyl)benzo[cd]indol-2(1H)-one, | Example 86 | 4.45 | 468.2 |
| 4-{4-[2-oxo-1-(4,4,4-trifluorobutyl)-1,2-dihydrobenzo[cd]indol-6-yl]-1,4-diazepan-1-yl}butanenitrile, | Example 87 | 4.02 | 445.3 |
| 1-(4-methoxybenzyl)-6-(4-propyl-1,4-diazepan-1-yl)benzo[cd]indol-2(1H)-one, | Example 88 | 4.377 | 430.3 |
| 6-[4-(cyclobutylmethyl)-1,4-diazepan-1-yl]-1-(4,4,4-trifluorobutyl)benzo[cd]indol-2(1H)-one, | Example 89 | 4.39 | 446.3 |
| 6-[4-(2-ethoxyethyl)-1,4-diazepan-1-yl]-1-(4,4,4-trifluorobutyl)benzo[cd]indol-2(1H)-one, | Example 90 | 4.19 | 450.4 |
| 6-(4-isopentyl-1,4-diazepan-1-yl)-1-(4,4,4-trifluorobutyl)benzo[cd]indol-2(1H)-one, | Example 91 | 4.5 | 448.3 |
| benzyl {4-[2-oxo-1-(4,4,4-trifluorobutyl)-1,2-dihydrobenzo[cd]indol-6-yl)-1,4-diazepan-1-yl}acetate, | Example 92 | 4.68 | 526.2 |
| 6-[4-(cyclopropylmethyl)-1,4-diazepan-1-yl]-1-(4,4,4-trifluorobutyl)benzo[cd]indol-2(1H)-one, | Example 93 | 4.19 | 432.3 |
| 6-[4-(3-nitrobenzyl)-1,4-diazepan-1-yl]-1-(4,4,4- | Example 94 | 4.51 | 513.2 |

TABLE 1-continued

Isobenzoindole Compounds Synthesized and LC/MS Data (min/M + H)

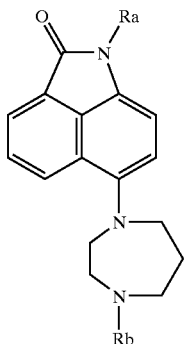

| Isobenzoindole Compound | Example No. | HPLC[1] minutes | MS[2] (M + H) |
|---|---|---|---|
| trifluorobutyl)benzo[cd]indol-2(1H)-one, | | | |
| 6-(4-propyl-1,4-diazepan-1-yl)-1-(3,3,3-trifluoropropyl)benzo[cd]indol-2(1H)-one, | Example 95 | 2.567 | 406.25 |
| 6-(4-butyl-1,4-diazepan-1-yl)-1-(3,3,3-trifluoropropyl)benzo[cd]indol-2(1H)-one, | Example 96 | 2.653 | 420.25 |
| 6-(4-isobutyl-1,4-diazepan-1-yl)-1-(3,3,3-trifluoropropyl)benzo[cd]indol-2(1H)-one, | Example 97 | 2.707 | 420.25 |
| 1-(3,3,3-trifluoropropyl)-6-[4-(3,3,3-trifluoropropyl)-1,4-diazepan-1-yl)benzo[cd]indol-2(1H)-one, | Example 98 | 2.7 | 460.25 |
| 6-[4-(4,4,4-trifluorobutyl)-1,4-diazepan-1-yl]-1-(3,3,3-trifluoropropyl)benzo[cd]indol-2(1H)-one, | Example 99 | 2.735 | 474.25 |
| 6-[4-(2-phenylethyl)-1,4-diazepan-1-yl]-1-(3,3,3-trifluoropropyl)benzo[cd]indol-2(1H)-one, | Example 100 | 2.845 | 468.25 |
| 4-{4-[2-oxo-1-(3,3,3-trifluoropropyl)-1,2-dihydrobenzo[cd]indol-6-yl]-1,4-diazepan-1-yl}butanenitrile, | Example 101 | 2.504 | 431.25 |
| 6-[4-(3-phenylpropyl)-1,4-diazepan-1-yl]-1-(3,3,3-trifluoropropyl)benzo[cd]indol-2(1H)-one, | Example 102 | 2.923 | 842.35 |
| 6-[4-(cyclobutylmethyl)-1,4-diazepan-1-yl]-1-(3,3,3-trifluoropropyl)benzo[cd]indol-2(1H)-one, | Example 103 | 2.722 | 432.25 |
| 6-[4-(2-ethoxyethyl)-1,4-diazepan-1-yl]-1-(3,3,3-trifluoropropyl)benzo[cd]indol-2(1H)-one, | Example 104 | 2.629 | 436.25 |
| 6-(4-isopentyl-1,4-diazepan-1-yl)-1-(3,3,3-trifluoropropyl)benzo[cd]indol-2(1H)-one, | Example 105 | 2.727 | 434.25 |
| benzyl {4-[2-oxo-1-(3,3,3-trifluoropropyl)-1,2-dihydrobenzo[cd)indol-6-yl]-1,4-diazepan-1-yl}acetate, | Example 106 | 2.916 | 512.3 |
| 6-[4-(cyclopropylmethyl)-1,4-diazepan-1-yl)-1-(3,3,3-trifluoropropyl)benzo[cd]indol-2(1H)-one, | Example 107 | 2.607 | 418.25 |
| 6-(4-isopropyl-1,4-diazepan-1-yl)-1-(3,3,3-trifluoropropyl)benzo[cd]indol-2(1H)-one, | Example 108 | 2.52 | 406.25 |
| 6-[4-(2-nitrobenzyl)-1,4-diazepan-1-yl]-1-(3,3,3-trifluoropropyl)benzo[cd]indol-2(1H)-one, | Example 109 | 2.735 | 499.25 |
| 6-[4-(4-methoxybenzyl)-1,4-diazepan-1-yl]-1-(3,3,3-trifluoropropyl)benzo[cd]indol-2(1H)-one, | Example 110 | 2.728 | 484.25 |
| 6-(4-butyl-1,4-diazepan-1-yl)-1-isopentylbenzo[cd]indol-2(1H)-one, | Example 111 | 2.532 | 394.25 |
| 6-(4-allyl-1,4-diazepan-1-yl)-1-isopentylbenzo[cd]indol-2(1H)-one, | Example 112 | 4.363 | 378.25 |
| 1-isopentyl-6-(4-pentyl-1,4-diazepan-1-yl)benzo[cd]indol-2(1H)-one, | Example 113 | 4.467 | 408.25 |
| 6-(4-isobutyl-1,4-diazepan-1-yl)-1-isopentylbenzo[cd]indol-2(1H)-one, | Example 114 | 4.403 | 394.25 |
| 1-isopentyl-6-[4-(3,3,3-trifluoropropyl)-1,4-diazepan-1-yl]benzo[cd]indol-2(1H)-one, | Example 115 | 4.519 | 434.25 |
| ethyl [4-(1-isopentyl-2-oxo-1,2-dihydrobenzo[cd]indol-6-yl)-1,4-diazepan-1-yl]acetate, | Example 116 | 4.389 | 424.25 |
| 1-isopentyl-6-[4-(2-phenylethyl)-1,4-diazepan-1-yl]benzo[cd]indol-2(1H)-one, | Example 117 | 4.48 | 442.25 |
| 4-[4-(1-isopentyl-2-oxo-1,2-dihydrobenzo[cd]indol-6-yl)-1,4-diazepan-1-yl]butanenitrile, | Example 118 | 4.36 | 405.25 |
| 1-isopentyl-6-[4-(3-phenylpropyl)-1,4-diazepan- | Example 119 | 4.496 | 456.25 |

TABLE 1-continued

Isobenzoindole Compounds Synthesized and LC/MS Data (min/M + H)

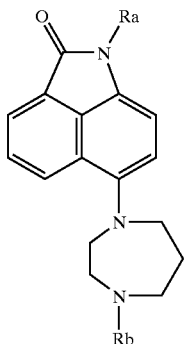

| Isobenzoindole Compound | Example No. | HPLC[1] minutes | MS[2] (M + H) |
|---|---|---|---|
| 1-yl]benzo[cd]indol-2(1H)-one, | | | |
| 6-[4-(cyclobutylmethyl)-1,4-diazepan-1-yl]-1-isopentylbenzo[cd]indol-2(1H)-one, | Example 120 | 4.419 | 406.25 |
| 6-[4-(2-ethoxyethyl)-1,4-diazepan-1-yl]-1-isopentylbenzo[cd]indol-2(1H)-one, | Example 121 | 2.739 | 410.25 |
| 1-isopentyl-6-(4-isopentyl-1,4-diazepan-1-yl)benzo[cd]indol-2(1H)-one, | Example 122 | 2.638 | 408.25 |
| benzyl [4-(1-isopentyl-2-oxo-1,2-dihydrobenzo[cd]indol-6-yl)-1,4-diazepan-1-yl]acetate, | Example 123 | 2.75 | 486.25 |
| 6-[4-(cyclohexylmethyl)-1,4-diazepan-1-yl]-1-isopentylbenzo[cd]indol-2(1H)-one, | Example 124 | 2.74 | 434.25 |
| 6-[4-(cyclopropylmethyl)-1,4-diazepan-1-yl]-1-isopentylbenzo[cd]indol-2(1H)-one, | Example 125 | 2.392 | 392.25 |
| 1-isopentyl-6-(4-isopropyl-1,4-diazepan-1-yl)benzo[cd]indol-2(1H)-one, | Example 126 | 2.35 | 380.25 |
| 1-isopentyl-6-[4-(2-nitrobenzyl)-1,4-diazepan-1-yl]benzo[cd]indol-2(1H)-one, | Example 127 | 2.589 | 473.25 |
| 1-isopentyl-6-[4-(4-methoxybenzyl)-1,4-diazepan-1-yl]benzo[cd]indol-2(1H)-one, | Example 128 | 2.663 | 458.25 |
| 1-butyl-6-(4-propyl-1,4-diazepan-1-yl)benzo[cd]indol-2(1H)-one, | Example 129 | 2.231 | 366.25 |
| 6-(4-allyl-1,4-diazepan-1-yl)-1-butylbenzo[cd]indol-2(1H)-one, | Example 130 | 2.158 | 364.2 |
| 1-butyl-6-(4-pentyl-1,4-diazepan-1-yl)benzo[cd]indol-2(1H)-one, | Example 131 | 2.487 | 394.25 |
| 1-butyl-6-(4-isobutyl-1,4-diazepan-1-yl)benzo[cd]indol-2(1H)-one, | Example 132 | 2.312 | 380.25 |
| 1-butyl-6-(4-cyclohexyl-1,4-diazepan-1-yl)benzo[cd]indol-2(1H)-one, | Example 133 | 2.409 | 406.25 |
| 1-butyl-6-[4-(2-phenylethyl)-1,4-diazepan-1-yl]benzo[cd]indol-2(1H)-one, | Example 134 | 2.52 | 428.25 |
| 4-[4-(1-butyl-2-oxo-1,2-dihydrobenzo[cd]indol-6-yl)-1,4-diazepan-1-yl]butanenitrile, | Example 135 | 2.115 | 391.25 |
| 1-butyl-6-[4-(3-phenylpropyl)-1,4-diazepan-1-yl]benzo[cd]indol-2(1H)-one, | Example 136 | 2.643 | 442.25 |
| 1-butyl-6-[4-(cyclobutylmethyl)-1,4-diazepan-1-yl]benzo[cd]indol-2(1H)-one, | Example 137 | 2.378 | 392.25 |
| 1-butyl-6-[4-(2-ethoxyethyl)-1,4-diazepan-1-yl]benzo[cd]indol-2(1H)-one, | Example 138 | 2.227 | 396.25 |
| 1-butyl-6-(4-isopentyl-1,4-diazepan-1-yl)benzo[cd]indol-2(1H)-one, | Example 139 | 2.478 | 394.25 |
| benzyl [4-(1-butyl-2-oxo-1,2-dihydrobenzo[cd]indol-6-yl)-1,4-diazepan-1-yl]acetate, | Example 140 | 2.578 | 472.25 |
| 1-butyl-6-(4-isopropyl-1,4-diazepan-1-yl)benzo[cd]indol-2(1H)-one, | Example 141 | 2.147 | 366.25 |
| 1-butyl-6-[4-(2-nitrobenzyl)-1,4-diazepan-1-yl]benzo[cd]indol-2(1H)-one, | Example 142 | 2.396 | 459.25 |
| 1-(2-phenylethyl)-6-(4-propyl-1,4-diazepan-1-yl)benzo[cd]indol-2(1H)-one, | Example 143 | 2.351 | 414.25 |
| 6-(4-butyl-1,4-diazepan-1-yl)-1-(2-phenylethyl)benzo[cd]indol-2(1H)-one, | Example 144 | 2.458 | 428.25 |
| 6-(4-allyl-1,4-diazepan-1-yl)-1-(2-phenylethyl)benzo[cd]indol-2(1H)-one, | Example 145 | 2.337 | 412.2 |
| 6-(4-pentyl-1,4-diazepan-1-yl)-1-(2-phenylethyl)benzo[cd]indol-2(1H)-one, | Example 146 | 2.604 | 442.25 |

TABLE 1-continued

Isobenzoindole Compounds Synthesized and LC/MS Data (min/M + H)

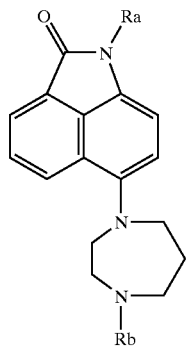

| Isobenzoindole Compound | Example No. | HPLC[1] minutes | MS[2] (M + H) |
|---|---|---|---|
| 6-(4-isobutyl-1,4-diazepan-1-yl)-1-(2-phenylethyl)benzo[cd]indol-2(1H)-one, | Example 147 | 2.462 | 428.25 |
| 1-(2-phenylethyl)-6-[4-(3,3,3-trifluoropropyl)-1,4-diazepan-1-yl]benzo[cd]indol-2(1H)-one, | Example 148 | 2.466 | 468.15 |
| 1-(2-phenylethyl)-6-[4-(4,4,4-trifluorobutyl)-1,4-diazepan-1-yl]benzo[cd]indol-2(1H)-one, | Example 149 | 2.557 | 482.25 |
| ethyl {4-[2-oxo-1-(2-phenylethyl)-1,2-dihydrobenzo[cd]indol-6-yl]-1,4-diazepan-1-yl}acetate, | Example 150 | 2.407 | 458.25 |
| 1-(2-phenylethyl)-6-[4-(2-phenylethyl)-1,4-diazepan-1-yl]benzo[cd]indol-2(1H)-one, | Example 151 | 2.661 | 476.25 |
| 4-{4-[2-oxo-1-(2-phenylethyl)-1,2-dihydrobenzo[cd]indol-6-yl]-1,4-diazepan-1-yl}butanenitrile, | Example 152 | 2.319 | 439.25 |
| 1-(2-phenylethyl)-6-[4-(3-phenylpropyl)-1,4-diazepan-1-yl]benzo[cd]indol-2(1H)-one, | Example 153 | 2.733 | 490.25 |
| 6-[4-(cyclobutylmethyl)-1,4-diazepan-1-yl]-1-(2-phenylethyl)benzo[cd]indol-2(1H)-one, | Example 154 | 2.541 | 440.25 |
| 6-[4-(2-ethoxyethyl)-1,4-diazepan-1-yl]-1-(2-phenylethyl)benzo[cd]indol-2(1H)-one, | Example 155 | 2.391 | /444.25 |
| 6-(4-isopentyl-1,4-diazepan-1-yl)-1-(2-phenylethyl)benzo[cd]indol-2(1H)-one, | Example 156 | 2.533 | 442.2 |
| benzyl (4-[2-oxo-1-(2-phenylethyl)-1,2-dihydrobenzo[cd]indol-6-yl]-1,4-diazepan-1-yl}acetate, | Example 157 | 2.569 | 520.25 |
| 6-[4-(cyclohexylmethyl)-1,4-diazepan-1-yl]-1-(2-phenylethyl)benzo[cd]indol-2(1H)-one, | ExampIe 158 | 2.719 | 468.25 |
| 6-[4-(cyclopropylmethyl)-1,4-diazepan-1-yl]-1-(2-phenylethyl)benzo[cd]indol-2(1H)-one, | Example 159 | 2.389 | 426.25 |
| 6-[4-(2-nitrobenzyl)-1,4-diazepan-1-yl]-1-(2-phenylethyl)benzo[cd]indol-2(1H)-one, | Example 160 | 2.549 | 507.25 |
| 6-[4-(4-methoxybenzyl)-1,4-diazepan-1-yl]-1-(2-phenylethyl)benzo[cd]indol-2(1H)-one, | Example 161 | 2.624 | 492.25 |
| 1-allyl-6-(4-propyl-1,4-diazepan-1-yl)benzo[cd]indol-2(1H)-one, | Example 162 | 1.921 | 350.15 |
| 1-allyl-6-(4-butyl-1,4-diazepan-1-yl)benzo[cd]indol-2(1H)-one, | Example 163 | 1.895 | 364.25 |
| 1-allyl-6-(4-allyl-1,4-diazepan-1-yl)benzo[cd]indol-2(1H)-one, | Example 164 | 2.121 | 348.2 |
| 1-allyl-6-(4-pentyl-1,4-diazepan-1-yl)benzo[cd]indol-2(1H)-one, | Example 165 | 2.286 | 378.25 |
| 1-allyl-6-(4-isobutyl-1,4-diazepan-1-yl)benzo[cd]indol-2(1H)-one, | Example 166 | 0.165 | 364.15 |
| 1-allyl-6-[4-(3,3,3-trifluoropropyl)-1,4-diazepan-1-yl]benzo[cd]indol-2(1H)-one, | Example 167 | 2.105 | 404.15 |
| 1-allyl-6-[4-(4,4,4-trifluorobutyl)-1,4-diazepan-1-yl]benzo[cd]indol-2(1H)-one, | Example 168 | 2.192 | 418.15 |
| 1-allyl-6-[4-(2-phenylethyl)-1,4-diazepan-1-yl]benzo[cd]indol-2(1H)-one, | Example 169 | 2.338 | 412.2 |
| 4-[4-(1-allyl-2-oxo-1,2-dihydrobenzo[cd]indol-6-yl)-1,4-diazepan-1-yl]butanenitrile, | Example 170 | 2.017 | 375.25 |
| 1-allyl-6-[4-(cyclobutylmethyl)-1,4-diazepan-1-yl]benzo[cd]indol-2(1H)-one, | Example 171 | 2.18 | 376.25 |
| 1-allyl-6-[4-(2-ethoxyethyl)-1,4-diazepan-1-yl]benzo[cd]indol-2(1H)-one, | Example 172 | 2.063 | 380.25 |
| 1-allyl-6-(4-isopentyl-1,4-diazepan-1-yl)benzo[cd]indol-2(1H)-one, | Example 173 | 2.234 | 378.25 |

TABLE 1-continued

Isobenzoindole Compounds Synthesized and LC/MS Data (min/M + H)

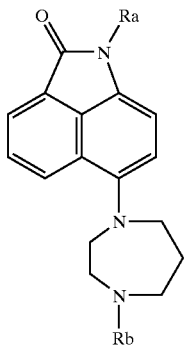

| Isobenzoindole Compound | Example No. | HPLC[1] minutes | MS[2] (M + H) |
|---|---|---|---|
| 1-(cyclohexylmethyl)-6-(4-propyl-1,4-diazepan-1-yl)benzo[cd]indol-2(1H)-one, | Example 174 | 2.541 | 406.25 |
| 6-(4-butyl-1,4-diazepan-1-yl)-1-(cyclohexylmethyl)benzo[cd]indol-2(1H)-one, | Example 175 | 2.681 | 420.25 |
| 6-(4-allyl-1,4-diazepan-1-yl)-1-(cyclohexylmethyl)benzo[cd]indol-2(1H)-one, | Example 176 | 2.526 | 404.25 |
| 1-(cyclohexylmethyl)-6-(4-pentyl-1,4-diazepan-1-yl)benzo[cd]indol-2(1H)-one, | Example 177 | 2.789 | 434.25 |
| 1-(cyclohexylmethyl)-6-(4-isobutyl-1,4-diazepan-1-yl)benzo[cd]indol-2(1H)-one, | Example 178 | 2.662 | 420.25 |
| 1-(cyclohexylmethyl)-6-[4-(3,3,3-trifluoropropyl)-1,4-diazepan-1-yl]benzo[cd]indol-2(1H)-one, | Example 179 | 2.655 | 460.25 |
| 1-(cyclohexylmethyl)-6-[4-(4,4,4-trifluorobutyl)-1,4-diazepan-1-yl)benzo[cd]indol-2(1H)-one, | Example 180 | 2.727 | 474.25 |
| 6-(4-cyclohexyl-1,4-diazepan-1-yl)-1-(cyclohexylmethyl)benzo[cd]indol-2(1H)-one, | Example 181 | 2.723 | 446.25 |
| 1-(cyclohexylmethyl)-6-[4-(2-phenylethyl)-1,4-diazepan-1-yl]benzo[cd]indol-2(1H)-one, | Example 182 | 2.816 | 468.25 |
| 4-{4-[1-(cyclohexylmethyl)-2-oxo-1,2-dihydrobenzo[cd]indol-6-yl]-1,4-diazepan-1-yl}butanenitrile, | Example 183 | 2.454 | 431.25 |
| 6-[4-(cyclobutylmethyl)-1,4-diazepan-1-yl]-1-(cyclohexylmethyl)benzo[cd]indol-2(1H)-one, | Example 184 | 2.694 | 432.25 |
| 1-(cyclohexylmethyl)-6-[4-(2-ethoxyethyl)-1,4-diazepan-1-yl]benzo(cd)indol-2(1H)-one, | Example 185 | 2.594 | 436.25 |
| 1-(cyclohexylmethyl)-6-(4-isopentyl-1,4-diazepan-1-yl)benzo[cd]indol-2(1H)-one, | Example 186 | 2.773 | 434.35 |
| 1-(cyclohexylmethyl)-6-[4-(cyclohexylmethyl)-1,4-diazepan-1-yl]benzo[cd]indol-2(1H)-one, | Example 187 | 2.87 | 460.35 |
| 1-(cyclohexylmethyl)-6-[4-(cyclopropylmethyl)-1,4-diazepan-1-yl)benzo[cd]indol-2(1H)-one, | Example 188 | 2.575 | 418.25 |
| {4-[1-(cyclohexylmethyl)-2-oxo-1,2-dihydrobenzo[cd]indol-6-yl]-1,4-diazepan-1-yl}acetonitrile, | Example 189 | 3.332 | 403.25 |
| 1-(cyclohexylmethyl)-6-[4-(3-nitrobenzyl)-1,4-diazepan-1-yl)benzo[cd]indol-2(1H)-one, | Example 190 | 2.761 | 499.25 |
| 1-(cyclohexylmethyl)-6-(4-isopropyl-1,4-diazepan-1-yl)benzo[cd]indol-2(1H)-one, | Example 191 | 2.522 | 406.25 |
| 1-(cyclohexylmethyl)-6-[4-(2-nitrobenzyl)-1,4-diazepan-1-yl)benzo[cd]indol-2(1H)-one, | Example 192 | 2.73 | 499.25 |

[1]LC conditions: Hewlett Packard 1100; YMC ODS-A 4.6 mm × 50 mm 5 u column at 23° C.; 10 uL injection; Solvent A: 0.05% TFA/water; Solvent B:0.05% TFA/acetonitrile; Gratient: Time 0: 98% A; 1 min: 98% A; 7 min: 10% A, 8 min: 10% A; 8.9 min: 98% A; Post time 1 min. Flow rate 2.5 mL/min; Detection: 220 and 254 nm DAD.
[2]MS conditions: API-electrospray

Example 193

2-Methyl-5-(4-methyl-1,4-diazepan-1-yl)-2H-naphtho[1,8-cd]isothiazole 1,1-Dioxide Example 193 was prepared as shown in Scheme 2

Scheme 2

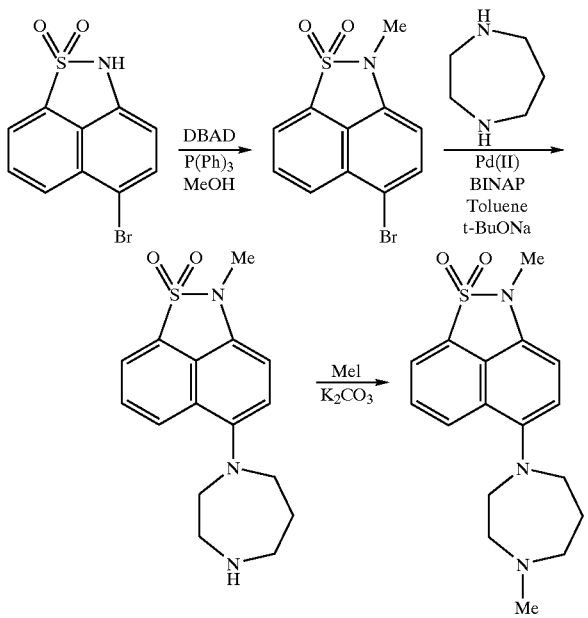

Step 1: 2-Methyl-5-bromo-2H-naphtho[1,8-cd]isothiazole 1,1-Dioxide:

A mixture of 5-bromo-2H-naphtho[1,8-cd]isothiazole 1,1-Dioxide (200 mg, 0.70 mmol), methanol(45 mg, 57 ml), and poly-TPP (Fluka, 580 mg, 1.75 mmol) in DCM (8 ml) under nitrogen was cooled to 5° C. and treated with DBAD (320 mg, 1.4 mmol). The mixture was slowly warmed to 20° C. and stirred for 1.5 hours. TFA (4 ml) was then added and the reaction mixture was stirred for another 1.5 hours. The reaction mixture was then filtered through celite, washed (DCM, 3×), evaporated, partitioned between 1N HCl (3 ml) and DCM (6 ml), filtered, passed through a phase separation tube (8 ml, celite, a little nitrogen pressure applied) and evaporated to a dark solid. The sample was then dried and vacuumed to give 211 mg product (100%). NMR shows the desired product.

Step 2: 2-Methyl-5-(1,4-diazepan-1-yl)-2H-naphtho[1,8-cd]isothiazole 1,1-Dioxide:

An oven dried, $N_2$ purged 8 ml vial was charged with 2-methyl-5-bromo-2H-naphtho[1,8-cd]isothiazole 1,1-dioxide, homopiperazine, $pd_2(dba)_3$, tBuONa and BINAP. The vial was re-purged with nitrogen, and a mixture of 1 ml solvent (1:1 toluene-DME) was added. The vial was capped and shaken at 80° C. for 15 hours, then it was cooled to room temperature and treated with DCM (1.5 ml) and polymer supported triphenyl phosphine (80 mg). After shaking for an hour, 1 ml DCM and 2 ml water were added and the mixture was shaken for another hour and then filtered through celite (12 ml fritted columns) and washed with DCM. The two phases were separated (8 ml phase separation tube) and the organic layer was analyzed. LC-MS showed product in all of the layers, the layer with toluene having the most product.

Step 3: 2-Methyl-5-(4-methyl-1,4-diazepan-1-yl)-2H-naphtho[1,8-cd]iso-thiazole 1,1-Dioxide:

A procedure similar to the procedure described for Step 3 of Example 1 was used.

In addition to Example 193, the following sultam compounds (see Table 2 below) were synthesized using similar procedures to those described for Example 193. The compounds in Table 2 are similar to Example 193 except that the compounds have different $R_a$ and $R_b$ groups as shown in the formula below and Table 2.

TABLE 2

Sultam Compounds Synthesized and LC/MS Data (min/M + H)

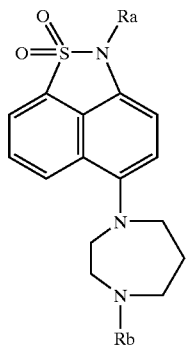

| Sultam Compounds | Example | HPLC[1] (minutes) | MS[2] (M + H) |
|---|---|---|---|
| 2-methyl-5-(4-methyl-1,4-diazepan-1-yl)-2H-naphthop[1,8-cd]isothiazole 1,1-dioxide, | Example 193 | 4.365 | 332.2 |
| 5-(4-ethyl-1,4-diazepan-1-yl)-2-methyl-2H-naphtho[1,8-cd]isothiazole 1,1-dioxide, | Example 194 | 4.557 | 346.3 |
| 2-methyl-5-(4-propyl-1,4-diazepan-1-yl)-2H-naphtho[1,8-cd]isothiazole 1,1-dioxide, | Example 195 | 4.858 | 360.2 |
| 5-(4-butyl-1,4-diazepan-1-yl)-2-methyl-2H-naphtho[1,8-cd]isothiazole 1,1-dioxide, | Example 196 | 5.251 | 374.3 |

TABLE 2-continued

Sultam Compounds Synthesized and LC/MS Data (min/M + H)

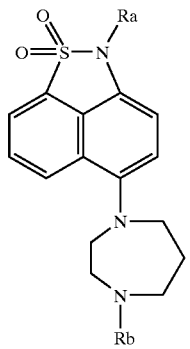

| Sultam Compounds | Example | HPLC[1] (minutes) | MS[2] (M + H) |
| --- | --- | --- | --- |
| 2-methyl-5-(4-neopentyl-1,4-diazepan-1-yl)-2H-naphtho[1,8-cd]isothiazole 1,1-dioxide, | Example 197 | 5.694 | 388.3 |
| 5-(4-benzyl-1,4-diazepan-1-yl)-2-methyl-2H-naphtho[1,8-cd]isothiazole 1,1-dioxide, | Example 198 | 5.606 | 408.3 |
| 2-methyl-5-[4-(2-phenylethyl)-1,4-diazepan-1-yl]-2H-naphtho[1,8-cd]isothiazole 1,1-dioxide, | Example 199 | 5.96 | 422.2 |
| 5-(1,4-diazepan-1-yl)-2-methyl-2H-naphtho[1,8-cd]isothiazole 1,1-dioxide, | Example 200 | 2.067 | 318.4 |
| 2-ethyl-5-(4-methyl-1,4-diazepan-1-yl)-2H-naphtho[1,8-cd]isothiazole 1,1-dioxide, | Example 201 | 4.736 | 346.3 |
| 2-ethyl-5-(4-ethyl-1,4-diazepan-1-yl)-2H-naphtho[1,8-cd]isothiazole 1,1-dioxide, | Example 202 | 4.93 | 360.2 |
| 2-ethyl-5-(4-propyl-1,4-diazepan-1-yl)-2H-naphtho[1,8-cd]isothiazole 1,1-dioxide, | Example 203 | 5.253 | 374.3 |
| 5-(4-butyl-1,4-diazepan-1-yl)-2-ethyl-2H-naphtho[1,8-cd]isothiazole 1,1-dioxide, | Example 204 | 5.621 | 388.3 |
| 2-ethyl-5-(4-neopentyl-1,4-diazepan-1-yl)-2H-naphtho[1,8-cd]isothiazole 1,1-dioxide, | Example 205 | 6.046 | 402.3 |
| 5-(4-benzyl-1,4-diazepan-1-yl)-2-ethyl-2H-naphtho[1,8-cd]isothiazole 1,1-dioxide, | Example 206 | 5.955 | 422.2 |
| 2-ethyl-5-[4-(2-phenylethyl)-1,4-diazepan-1-yl]-2H-naphtho[1,8-cd]isothiazole 1,1-dioxide, | Example 207 | 6.272 | 436.2 |
| 5-(1,4-diazepan-1-yl)-2-ethyl-2H-naphtho[1,8-cd]isothiazole 1,1-dioxide, | Example 208 | 2.193 | 332.4 |
| 5-(4-methyl-1,4-diazepan-1-yl)-2-propyl-2H-naphtho[1,8-cd]isothiazole 1,1-dioxide, | Example 209 | 5.251 | 360.2 |
| 5-(4-ethyl-1,4-diazepan-1-yl)-2-propyl-2H-naphtho[1,8-cd]isothiazole 1,1-dioxide, | Example 210 | 5.435 | 374.3 |
| 2-propyl-5-(4-propyl-1,4-diazepan-1-yl)-2H-naphtho[1,8-cd]isothiazole 1,1-dioxide, | Example 211 | 5.752 | 388.3 |
| 5-(4-butyl-1,4-diazepan-1-yl)-2-propyl-2H-naphtho[1,8-cd]isothiazole 1,1-dioxide, | Example 212 | 6.132 | 402.3 |
| 5-(4-neopentyl-1,4-diazepan-1-yl)-2-propyl-2H-naphtho[1,8-cd]isothiazole 1,1-dioxide, | Example 213 | 6.509 | 416.3 |
| 5-(4-benzyl-1,4-diazepan-1-yl)-2-propyl-2H-naphtho[1,8-cd]isothiazole 1,1-dioxide, | Example 214 | 6.405 | 436.2 |
| 5-[4-(2-phenylethyl)-1,4-diazepan-1-yl]-2-propyl-2H-naphtho[1,8-cd]isothiazole 1,1-dioxide, | Example 215 | 6.703 | 450.3 |
| 5-(1,4-diazepan-1-yl)-2-propyl-2H-naphtho[1,8-cd]isothiazole 1,1-dioxide, | Example 216 | 2.424 | 346.4 |
| 5-(1,4-diazepan-1-yl)-2-isopropyl-2H-naphtho[1,8-cd]isothiazole 1,1-dioxide, | Example 217 | 2.354 | 346.5 |
| 2-butyl-5-(1,4-diazepan-1-yl)-2H-naphtho[1,8-cd]isothiazole 1,1-dioxide, | Example 218 | 2.633 | 360.4 |
| 5-(1,4-diazepan-1-yl)-2-hexyl-2H-naphtho[1,8-cd]isothiazole 1,1-dioxide, | Example 219 | 2.995 | 388.4 |
| 2-isobutyl-5-(4-methyl-1,4-diazepan-1-yl)-2H-naphtho[1,8-cd]isothiazole 1,1-dioxide, | Example 220 | 4.998 | 374.3 |
| 5-(4-ethyl-1,4-diazepan-1-yl)-2-isobutyl-2H-naphtho[1,8-cd]isothiazole 1,1-dioxide, | Example 221 | 5.118 | 388.3 |
| 2-isobutyl-5-(4-propyl-1,4-diazepan-1-yl)-2H-naphtho[1,8-cd]isothiazole 1,1-dioxide, | Example 222 | 5.336 | 402.3 |
| 5-(4-butyl-1,4-diazepan-1-yl)-2-isobutyl-2H-naphtho[1,8-cd]isothiazole 1,1-dioxide, | Example 223 | 5.64 | 416.3 |
| 2-isobutyl-5-(4-neopentyl-1,4-diazepan-1-yl)- | Example 224 | 5.902 | 430.3 |

TABLE 2-continued

Sultam Compounds Synthesized and LC/MS Data (min/M + H)

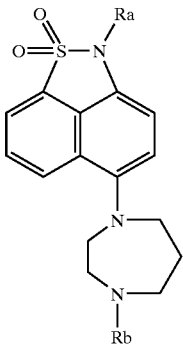

| Sultam Compounds | Example | HPLC[1] (minutes) | MS[2] (M + H) |
|---|---|---|---|
| 2H-naphtho[1,8-cd]isothiazole 1,1-dioxide, | | | |
| 5-(4-benzyl-1,4-diazepan-1-yl)-2-isobutyl-2H-naphtho[1,8-cd]isothiazole 1,1-dioxide, | Example 225 | 5.824 | 450.3 |
| 2-isobutyl-5-[4-(2-phenylethyl)-1,4-diazepan-1-yl]-2H-naphtho[1,8-cd]isothiazole 1,1-dioxide, | Example 226 | 6.035 | 464.3 |
| 5-(4-methyl-1,4-diazepan-1-yl)-2-pentyl-2H-naphtho[1,8-cd]isothiazole 1,1-dioxide, | Example 227 | 5.455 | 388.5 |
| 5-(4-ethyl-1,4-diazepan-1-yl)-2-pentyl-2H-naphtho[1,8-cd]isothiazole 1,1-dioxide, | Example 228 | 5.553 | 402.3 |
| 2-pentyl-5-(4-propyl-1,4-diazepan-1-yl)-2H-naphtho[1,8-cd]isothiazole 1,1-dioxide, | Example 229 | 5.775 | 416.3 |
| 5-(4-benzyl-1,4-diazepan-1-yl)-2-pentyl-2H-naphtho[1,8-cd]isothiazole 1,1-dioxide, | Example 230 | 6.046 | 430.3 |
| 2-pentyl-5-[4-(2-phenylethyl)-1,4-diazepan-1-yl]-2H-naphtho[1,8-cd]isothiazole 1,1-dioxide, | Example 231 | 6.197 | 464.3 |
| 5-(1,4-diazepan-1-yl)-2-pentyl-2H-naphtho[1,8-cd]isothiazole 1,1-dioxide, | Example 232 | 6.394 | 478.3 |
| 5-(4-methyl-1,4-diazepan-1-yl)-2-(2-phenylethyl)-2H-naphtho[1,8-cd]isothiazole 1,1-dioxide, | Example 233 | 5.416 | 422.2 |
| 5-(4-ethyl-1,4-diazepan-1-yl)-2-(2-phenylethyl)-2H-naphtho[1,8-cd]isothiazole 1,1-dioxide, | Example 234 | 5.507 | 436.2 |
| 2-(2-phenylethyl)-5-(4-propyl-1,4-diazepan-1-yl)-2H-naphtho[1,8-cd]isothiazole 1,1-dioxide, | Example 235 | 5.713 | 450.3 |
| 5-(4-butyl-1,4-diazepan-1-yl)-2-(2-phenylethyl)-2H-naphtho[1,8-cd]isothiazole 1,1-dioxide, | Example 236 | 5.963 | 464.3 |
| 5-(4-neopentyl-1,4-diazepan-1-yl)-2-(2-phenylethyl)-2H-naphtho[1,8-cd]isothiazole 1,1-dioxide, | Example 237 | 6.211 | 478.3 |
| 5-(4-benzyl-1,4-diazepan-1-yl)-2-(2-phenylethyl)-2H-naphtho[1,8-cd]isothiazole 1,1-dioxide, | Example 238 | 6.102 | 498.4 |
| 2-(2-phenylethyl)-5-[4-(2-phenylethyl)-1,4-diazepan-1-yl]-2H-naphtho[1,8-cd]isothiazole 1,1-dioxide, | Example 239 | 6.31 | 512.2 |
| 5-(4-methyl-1,4-diazepan-1-yl)-2-(3-phenylpropyl)-2H-naphtho[1,8-cd]isothiazole 1,1-dioxide, | Example 240 | 5.726 | 436.2 |
| 5-(4-ethyl-1,4-diazepan-1-yl)-2-(3-phenylpropyl)-2H-naphtho[1,8-cd]isothiazole 1,1-dioxide, | Example 241 | 5.814 | 450.5 |
| 2-(3-phenylpropyl)-5-(4-propyl-1,4-diazepan-1-yl)-2H-naphtho[1,8-cd]isothiazole 1,1-dioxide, | Example 242 | 6.005 | 464.3 |
| 5-(4-butyl-1,4-diazepan-1-yl)-2-(3-phenylpropyl)-2H-naphtho[1,8-cd]isothiazole 1,1-dioxide, | Example 243 | 6.234 | 478.3 |
| 5-(4-benzyl-1,4-diazepan-1-yl)-2-(3-phenylpropyl)-2H-naphtho[1,8-cd]isothiazole 1,1-dioxide, | Example 244 | 6.393 | 512.2 |

TABLE 2-continued

Sultam Compounds Synthesized and LC/MS Data (min/M + H)

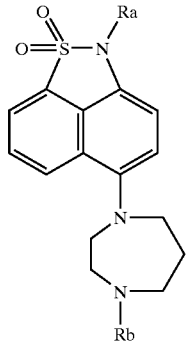

| Sultam Compounds | Example | HPLC[1] (minutes) | MS[2] (M + H) |
|---|---|---|---|
| 5-[4-(2-phenylethyl)-1,4-diazepan-1-yl]-2-(3-pheny(propyl)-2H-naphtho[1,8-cd]isothiazole 1,1-dioxide, | Example 245 | 6.558 | 526.2 |
| 2-(cyclohexylmethyl)-5-(4-methyl-1,4-diazepan-1-yl)-2H-naphtho[1,8-cd]isothiazole 1,1-dioxide, | Example 246 | 5.801 | 414.2 |
| 2-(cyclohexylmethyl)-5-(4-propyl-1,4-diazepan-1-yl)-2H-naphtho[1,8-cd]isothiazole 1,1-dioxide, | Example 247 | 6.129 | 442.3 |
| 5-(4-butyl-1,4-diazepan-1-yl)-2-(cyclohexylmethyl)-2H-naphtho[1,8-cd]isothiazole 1,1-dioxide, | Example 248 | 6.393 | 456.3 |
| 2-(cyclohexylmethyl)-5-(4-neopentyl-1,4-diazepan-1-yl)-2H-naphtho[1,8-cd]isothiazole 1,1-dioxide, | Example 249 | 6.638 | 470.3 |
| 5-(4-benzyl-1,4-diazepan-1-yl)-2-(cyclohexylmethyl)-2H-naphtho[1,8-cd]isothiazole 1,1-dioxide, | Example 250 | 6.549 | 490.3 |
| 2-(cyclohexylmethyl)-5-[4-(2-phenylethyl)-1,4-diazepan-1-yl]-2H-naphtho[1,8-cd]isothiazole 1,1-dioxide, | Example 251 | 6.722 | 504.2 |

[1]LC conditions: Hewlett Packard 1100; YMC ODS-A 4.6 mm × 50 mm 5 u column at 23° C.; 10 uL injection; Solvent A: 0.05% TFA/water; Solvent B: 0.05% TFA/acetonitrile; Gratient: Time 0: 98% A; 1 min; 98% A; 7 min: 10% A, 8 min: 10% A; 8.9 min: 98% A; Post time 1 min. Flow rate 2.5 mL/min; Detection: 220 and 254 nm DAD.
[2]MS conditions: API-electrospray

Example 254

2-Dipropyl-6-(4-methyl-1,4-diazepan-1-yl)-1,2-dihydroacenaphthylen-1-one

Example 254 was prepared as shown in Scheme 3

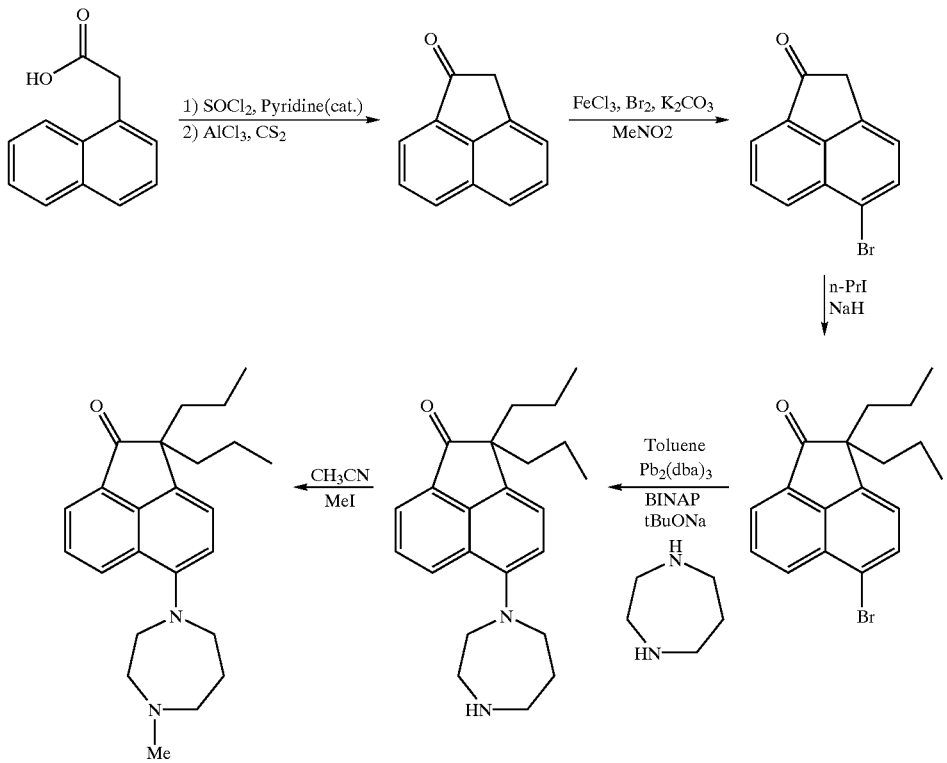

Scheme 3

Step 1: 1,2-Dihydroacenaphthylen-1-one:

To a solution of a-naphthylacetic acid (5 g, 26.9 mmol) in DCM (30 ml) was added a few drops of pyridine followed by the addition of Thionyl chloride (4.79 g, 40.3 mmol) and the reaction mixture was stirred at room temperature for 3 hours. The mixture was then vacuumed to remove the solvent. The residue was solvated with carbon disulfide (100 ml), and aluminum chloride (4.30 g, 32.2 mol) was then added. The resulting black mixture was stirred overnight. Quenching of the reaction mixture was done by adding 80 ml 1 N NaOH over a 40 minute period to the ice cooled solution and stirring was continued for another 30 minutes. The reaction mixture was filtered through celite, and the aqueous layer was extracted twice with toluene. The combined organic layers were dried over $MgSO_4$, filtered and concentrated. NMR confirmed the formation of the desired product.

Step 2: 6-Bromo-1,2-dihydroacenaphthylen-1-one:

To a mixture of 1,2-dihydroacenaphthylen-i-one (200 mg, 1.2 mmol), iron chloride (40 mg, 0.2 mmol), and potassium carbonate (663 mg, 4.8 mmol) in nitromethane (6 ml) was added bromine (943 mg, 5.9 mmol). The reaction was monitored by TLC with DCM as the eluent. The reaction was worked up after 75 minutes by quenching with saturated sodium bisulfite. The mixture was then poured into water and extracted with ethyl acetate and the organic layer was dried over sodium sulfate. Re-crystallization from hexane gave the desired product.

Step 3: 2,2-Dipropyl-6-bromo-1,2-dihydroacenaphthylen-1-one:

To a heat dried 8 ml vial loaded with 6-bromo-1,2-dihydroacenaphthylen-1-one (100 mg, 0.41 mmol) and sodium hydride (49 mg, 0.4 mmol) was added 1 ml THF. Propyl iodide (230 µl, 0.4 mmol) was then added to the above purple solution and the mixture was stirred for 1 hour. The reaction was then quenched with 300 ml acetic acid followed by the addition of DCM. The precipitate formed was filtered off and the filtrate concentrated to dryness to give 2.5 grams (80%) of product. NMR and MS confirmed the product.

Step 4: 6-(4-Methyl-1,4-diazepan-1-yl)-1,2-dihydroacenaphthylen-1-one:

The procedure used in this step was similar to the procedure described in step 2 of Example 1.

Step 5: 6-(4-Methyl-1,4-diazepan-1-yl)-1,2-dihydroacenaphthylen-1-one:

The procedure used in this step was similar to the procedure described in step 3 of Example 1.

In addition to Example 254, the following 1,2-dihydroacenaphthylen-1-one related compounds (see Table 3 below) were synthesized using similar procedures to those described for Example 254. The compounds in Table 3 are similar to Example 254 except that the compounds have different $R_a$, $R_b$ and $R_c$ groups as shown in the formula below and Table 3.

TABLE 3

1,2-dihydroacenaphthylene-1-one Compounds Synthesized and LC/MS Data

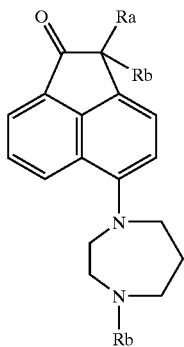

| 1,2-dihydroacenaphthylen-1-one Compounds | Example No. | HPLC[1] minutes | MS[2] (M + H) |
|---|---|---|---|
| 2,2-dimethyl-5-(4-methyl-1,4-diazepan-1-yl)acenaphthylen-1(2H)-one, | Example 252 | 5.039 | 309.3 |
| 2,2-diethyl-5-(4-methyl-1,4-diazepan-1-yl)acenaphthylen-1(2H)-one, | Example 253 | 5.558 | 337.1 |
| 5-(4-methyl-1,4-diazepan-1-yl)-2,2-dipropylacenaphthylen-1(2H)-one, | Example 254 | 6.461 | 365.3 |
| 2,2-dibutyl-5-(4-methyl-1,4-diazepan-1-yl)acenaphthylen-1(2H)-one, | Example 255 | 7.468 | 393.3 |
| 5-(4-methyl-1,4-diazepan-1-yl)-2,2-dipentylacenaphthylen-1(2H)-one, | Example 256 | 8.315 | 421.4 |
| 2,2-dibenzyl-5-(4-methyl-1,4-diazepan-1-yl)acenaphthylen-1(2H)-one, | Example 257 | 6.843 | 461.3 |
| Spiro{cyclopentane-1,2'-[5'-(4''-methyl-1'',4''-diazepan-1''-yl)-acenaphthylen-1'(2'H)-one]}, | Example 258 | 5.728 | 335.2 |
| 5-(4-ethyl-1,4-diazepan-1-yl)-2,2-dimethylacenaphthylen-1(2H)-one, | Example 259 | 5.029 | 323.1 |
| 2,2-diethyl-5-(4-ethyl-1,4-diazepan-1-yl)acenaphthylen-1(2H)-one, | Example 260 | 5.688 | 351.1 |
| 5-(4-ethyl-1,4-diazepan-1-yl)-2,2-dipropylacenaphthylen-1(2H)-one, | Example 261 | 6.78 | 379.4 |
| 2,2-dibutyl-5-(4-ethyl-1,4-diazepan-1-yl)acenaphthylen-1(2H)-one, | Example 262 | 7.394 | 407.4 |
| 5-(4-ethyl-1,4-diazepan-1-yl)-2,2-dipentylacenaphthylen-1(2H)-one, | Example 263 | 8.272 | 453.3 |
| 2,2-dibenzyl-5-(4-ethyl-1,4-diazepan-1-yl)acenaphthylen-1(2H)-one, | Example 264 | 6.972 | 475.3 |
| Spiro{cyclobutane-1,2'-[5'-(4''-ethyl-1'',4''-diazepan-1''-yl)-acenaphthylen-1'(2'H)-one]}, | Example 265 | 5.324 | 335.1 |
| Spiro{cyclopentane-1,2'-[5'-(4''-ethyl-1'',4''-diazepan-1''-yl)-acenaphthylen-1'(2'H)-one]}, | Example 266 | 5.684 | 349.2 |
| Spiro{cyclohexane-1,2'-[5'-(4''-ethyl-1'',4''-diazepan-1''-yl)-acenaphthylen-1'(2'H)-one]}, | Example 267 | 6.121 | 363.3 |
| 2,2-dimethyl-5-(4-propyl-1,4-diazepan-1-yl)acenaphthylen-1(2H)-one, | Example 268 | 5.331 | 337.1 |
| 2,2-diethyl-5-(4-propyl-1,4-diazepan-1-yl)acenaphthylen-1(2H)-one, | Example 269 | 5.972 | 365.3 |
| 2,2-dipropyl-5-(4-propyl-1,4-diazepan-1-yl)acenaphthylen-1(2H)-one, | Example 270 | 6.88 | 393.2 |
| 2,2-dibutyl-5-(4-propyl-1,4-diazepan-1-yl)acenaphthylen-1(2H)-one, | Example 271 | 7.653 | 421.3 |
| 2,2-dipentyl-5-(4-propyl-1,4-diazepan-1-yl)acenaphthylen-1(2H)-one, | Example 272 | 8.521 | 449.3 |
| 2,2-dibenzyl-5-(4-propyl-1,4-diazepan-1-yl)acenaphthylen-1(2H)-one, | Example 273 | 7.202 | 489.2 |
| Spiro{cyclobutane-1,2'-[5'-(4''-propyl-1'',4''-diazepan-1''-yl)-acenaphthylen-1'(2'H)-one]}, | Example 274 | 5.637 | 349.1 |
| Spiro{(cyclopentane-1,2'-[5'-(4''-propyl-1'',4''-diazepan-1''-yl)-acenaphthylen-1'(2'H)-one]}, | Example 275 | 5.989 | 363.3 |
| Spiro{cyclohexane-1,2'-[5'-(4''-propyl-1'',4''-diazepan-1''-yl)-acenaphthylen-1'(2'H)-one]}, | Example 276 | 6.634 | 377.3 |
| 5-(4-allyl-1,4-diazepan-1-yl)-2,2-dimethylacenaphthylen-1(2H)-one, | Example 277 | 5.246 | 335.2 |
| 5-(4-allyl-1,4-diazepan-1-yl)-2,2-diethylacenaphthylen-1(2H)-one, | Example 278 | 6.114 | 363.3 |
| 5-(4-allyl-1,4-diazepan-1-yl)-2,2-dipropylacenaphthylen-1(2H)-one, | Example 279 | 6.803 | 391.2 |

TABLE 3-continued 1,2-dihydroacenaphthylene-1-one Compounds Synthesized and LC/MS Data

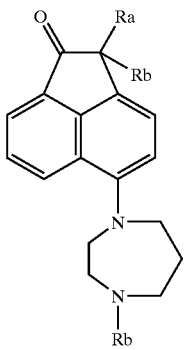

| 1,2-dihydroacenaphthylen-1-one Compounds | Example No. | HPLC[1] minutes | MS[2] (M + H) |
|---|---|---|---|
| 5-(4-allyl-1,4-diazepan-1-yl)-2,2-dibutylacenaphthylen-1(2H)-one, | Example 280 | 7.583 | 419.4 |
| 5-(4-allyl-1,4-diazepan-1-yl)-2,2-dipentylacenaphthylen-1(2H)-one, | Example 281 | 8.432 | 447.3 |
| 5-(4-allyl-1,4-diazepan-1-yl)-2,2-dibenzylacenaphthylen-1(2H)-one, | Example 282 | 7.38 | 487.3 |
| Spiro{cyclobutane-1,2'-[5'-(4"-allyl-1",4"-diazepan-1"-yl)-acenaphthylen-1'(2'H)-one]}, | Example 283 | 5.552 | 347.2 |
| Spiro{cyclopentane-1,2'-[5'-(4"-allyl-1",4"-diazepan-1"-yl)-acenaphthylen-1'(2'H)-one]}, | Example 284 | 5.915 | 361.2 |
| Spiro{cyclohexane-1,2'-[5'-(4"-allyl-1'1",4"-diazepan-1"-yl)-acenaphthylen-1'(2'H)-one]}, | Example 285 | 6.326 | 375.3 |
| 5-(4-butyl-1,4-diazepan-1-yl)-2,2-dimethylacenaphthylen-1(2H)-one, | Example 286 | 5.92 | 351.3 |
| 5-(4-butyl-1,4-diazepan-1-yl)-2,2-diethylacenaphthylen-1(2H)-one, | Example 287 | 6.534 | 379.4 |
| 5-(4-butyl-1,4-diazepan-1-yl)-2,2-dipropylacenaphthylen-1(2H)-one, | Example 288 | 7.46 | 407.3 |
| 2,2-dibutyl-5-(4-butyl-1,4-diazepan-1-yl)acenaphthylen-1(2H)-one, | Example 289 | 8.199 | 435.3 |
| 5-(4-butyl-1,4-diazepan-1-yl)-2,2-dipentylacenaphthylen-1(2H)-one, | Example 290 | 9.051 | 463.3 |
| 2,2-dibenzyl-5-(4-butyl-1,4-diazepan-1-yl)acenaphthylen-1(2H)-one, | Example 291 | 7.701 | 503.3 |
| Spiro{cyclobutane-1,2'-[5'-(4"-butyl-1",4"-diazepan-1"-yl)-acenaphthylen-1'(2'H)-one]}, | Example 292 | 6.214 | 363.3 |
| Spiro{cyclopentane-1,2'-[5'-(4"-butyl-1"1",4"-diazepan-1"-yl)-acenaphthylen-1'(2'H)-one]}, | Example 293 | 6.579 | 377.3 |
| Spiro{cyclohexane-1,2'-[51-(4"1-butyl-1"1,4"1-diazepan-1"-yl)-acenaphthylen-1'(2'H)-one]}, | Example 294 | 6.973 | 391.3 |
| 2,2-dimethyl-5-(4-pentyl-1,4-diazepan-1-yl)acenaphthylen-1(2H)-one, | Example 295 | 6.143 | 365.3 |
| 2,2-diethyl-5-(4-pentyl-1,4-diazepan-1-yl)acenaphthylen-1(2H)-one, | Example 296 | 6.738 | 393.2 |
| 5-(4-pentyl-1,4-diazepan-1-yl)-2,2-dipropylacenaphthylen-1(2H)-one, | Example 297 | 4.453 | 421.3 |
| 2,2-dibutyl-5-(4-pentyl-1,4-diazepan-1-yl)acenaphthylen-1(2H)-one, | Example 298 | 8.186 | 449.3 |
| 2,2-dipentyl-5-(4-pentyl-1,4-diazepan-1-yl)acenaphthylen-1(2H)-one, | Example 299 | 9.013 | 477.4 |
| 2,2-dibenzyl-5-(4-pentyl-1,4-diazepan-1-yl)acenaphthylen-1(2H)-one, | Example 300 | 7.97 | 517.3 |
| Spiro{cyclobutane-1,2'-[5'-(4"-pentyl-1",4"-diazepan-1"-yl)-acenaphthylen-1'(2'H)-one]}, | Example 301 | 6.374 | 377.3 |
| Spiro{cyclopentane-1,2'-[5'-(4"-pentyl-1",4"-diazepan-1"-yl)-acenaphthylen-1'(2'H)-one]}, | Example 302 | 6.692 | 391.3 |
| Spiro{cyclohexane-1,2'-[5'-(4"-pentyl-1",4"-diazepan-1"-yl)-acenaphthylen-1'(2'H)-one]}, | Example 303 | 6.974 | 405.2 |
| 2,2-dimethyl-5-(4-neopentyl-1,4-diazepan-1-yl)acenaphthylen-1(2H)-one, | Example 304 | 6.387 | 365.4 |
| 5-(4-neopentyl-1,4-diazepan-1-yl)-2,2-dipentylacenaphthylen-1(2H)-one, | Example 305 | 9.167 | 477.4 |
| Spiro{cyclobutane-1,2'[5'(4"-neopentyl-1",4"-diazepan-1"-yl)-acenapthylen-1'(2'H)-one]} | Example 306 | 6.455 | 377.3 |
| 2,2-dimethyl-5-[4-(4,4,4-trifluorobutyl)-1,4-diazepan-1-yl]acenaphthylen-1(2H)-one, | Example 307 | 5.893 | 405.2 |

TABLE 3-continued 1,2-dihydroacenaphthylene-1-one Compounds Synthesized and LC/MS Data

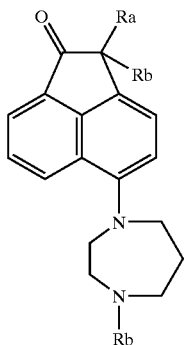

| 1,2-dihydroacenaphthylen-1-one Compounds | Example No. | HPLC[1] minutes | MS[2] (M + H) |
|---|---|---|---|
| 2,2-diethyl-5-[4-(4,4,4-trifluorobutyl)-1,4-diazepan-1-yl]acenaphthylen-1(2H)-one, | Example 308 | 6.552 | 433.2 |
| 2,2-dipropyl-5-[4-(4,4,4-trifluorobutyl)-1,4-diazepan-1-yl)acenaphthylen-1(2H)-one, | Example 309 | 7.293 | 461.3 |
| 2,2-dibutyl-5-[4-(4,4,4-trifluorobutyl)-1,4-diazepan-1-yl]acenaphthylen-1(2H)-one, | Example 310 | 7.967 | 489.2 |
| 2,2-dipentyl-5-[4-(4,4,4-trifluorobutyl)-1,4-diazepan-1-yl]acenaphthylen-1(2H)-one, | Example 311 | 8.822 | 517.2 |
| 2,2-dibenzyl-5-[4-(4,4,4-trifluorobutyl)-1,4-diazepan-1-yl]acenaphthylen-1(2H)-one, | Example 312 | 7.552 | 557.2 |
| Spiro{cyclobutane-1,2'-[5'-(4"-(4,4,4-trifluorobutyl)-1",4"-diazepan-1"-yl)-acenaphthylen-1'(2'H)-one]}, | Example 313 | 6.164 | 417.2 |
| Spiro{cyclopentane-1,2'-[5'-(4"-(4,4,4-trifluorobutyl)-1",4"-diazepan-1"-yl)-acenaphthylen-1'(2'H)-one]}, | Example 314 | 6.469 | 431.2 |
| Spiro{cyclohexane-1,2'-[5'-(4"-(4,4,4-trifluorobutyl)-1",4"-diazepan-1"-yl)-acenaphthylen-1'(2'H)-one]}, | Example 315 | 7.176 | 445.2 |
| 2,2-dimethyl-5-[4-(3,3,3-trifluoropropyl)-1,4-diazepan-1-yl)acenaphthylen-1(2H)-one, | Example 316 | 5.869 | 391.2 |
| 2,2-diethyl-5-[4-(3,3,3-trifluoropropyl)-1,4-diazepan-1-yl)acenaphthylen-1(2H)-one, | Example 317 | 6.256 | 419.2 |
| 2,2-dipropyl-5-[4-(3,3,3-trifluoropropyl)-1,4-diazepan-1-yl]acenaphthylen-1(2H)-one, | Example 318 | 7.403 | 447.2 |
| 2,2-dibutyl-5-[4-(3,3,3-trifluoropropyl)-1,4-diazepan-1-yl]acenaphthylen-1(2H)-one, | Example 319 | 8.152 | 475.3 |
| 2,2-dipentyl-5-[4-(3,3,3-trifluoropropyl)-1,4-diazepan-1-yl]acenaphthylen-1(2H)-one, | Example 320 | 8.697 | 503.2 |
| 2,2-dibenzyl-5-[4-(3,3,3-trifluoropropyl)-1,4-diazepan-1-yl]acenaphthylen-1(2H)-one, | Example 321 | 7.679 | 543.3 |
| Spiro{cyclobutane-1,2'-[5'-(4"-(3,3,3-trifluoropropyl)-1",4"-diazepan-1"-yl)-acenaphthylen-1'(2'H)-one]}, | Example 322 | 6.139 | 403.1 |
| Spiro{cyclopentane-1,2'-[5'-(4"-(3,3,3-trifluoropropyl)-1",4"-diazepan-1"-yl)-acenaphthylen-1'(2'H)-one]}, | Example 323 | 6.245 | 417.2 |
| Spiro{cyclohexane-1,2'-[5'-(4"-(3,3,3-trifluoropropyl)-1",4"1-diazepan-1"-yl)-acenaphthylen-1'(2'H)-one]}, | Example 324 | 6.661 | 431.2 |
| 5-[4-(cyclohexylmethyl)-1,4-diazepan-1-y')-2,2-dimethylacenaphthylen-1(2H)-one, | Example 325 | 6.662 | 391.3 |
| 5-[4-(cyclohexylmethyl)-1,4-diazepan-1-yl]-2,2-dipropylacenaphthylen-1(2H)-one, | Example 326 | 8.039 | 447.3 |
| 2,2-dibutyl-5-[4-(cyclohexylmethyl)-1,4-diazepan-1-yl]acenaphthylen-1(2H)-one, | Example 327 | 8.75 | 475.4 |
| 5-[4-(cyclohexylmethyl)-1,4-diazepan-1-yl]-2,2-dipentylacenaphthylen-1(2H)-one, | Example 328 | 9.576 | 503.4 |
| 2,2-dibenzyl-5-[4-(cyclohexylmethyl)-1,4-diazepan-1-yl]acenaphthylen-1(2H)-one, | Example 329 | 8.215 | 543.4 |
| Spiro{cyclobutane-1,2'-[5'-(4"-cyclohexylmethyl-1",4"-diazepan-1'-yl)-acenaphthylen-1'(2'H)-one]}, | Example 330 | 6.933 | 403.3 |
| 2,2-dimethyl-5-[4-(2-methylprop-2-enyl)-1,4-diazepan-1-yl]acenaphthylen-1(2H)-one, | Example 331 | 5.722 | 349.2 |
| 2,2-diethyl-5-[4-(2-methylprop-2-enyl)-1,4-diazepan-1-y'] acenaphthylen-1(2H)-one, | Example 332 | 6.358 | 377.2 |
| 5-[4-(2-methylprop-2-enyl)-1,4-diazepan-1-yl]-2,2-dipropylacenaphthylen-1(2H)-one, | Example 333 | 7.25 | 405.2 |
| 2,2-dibutyl-5-(4-(2-methylprop-2-enyl)-1,4-diazepan-1-yl]acenaphthylen-1(2H)-one, | Example 334 | 7.996 | 433.3 |
| 5-[4-(2-methylprop-2-enyl)-1,4-diazepan-1-yl]-2,2-dipentylacenaphthylen-1(2H)-one, | Example 335 | 8.863 | 461.3 |

TABLE 3-continued 1,2-dihydroacenaphthylene-1-one Compounds Synthesized and LC/MS Data

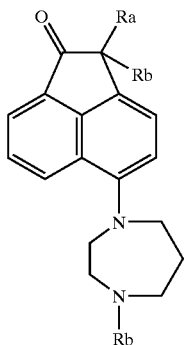

| 1,2-dihydroacenaphthylen-1-one Compounds | Example No. | HPLC[1] minutes | MS[2] (M + H) |
|---|---|---|---|
| 2,2-dibenzyl-5-[4-(2-methylprop-2-enyl)-1,4-diazepan-1-yl]acenaphthylen-1(2H)-one, | Example 336 | 7.518 | 501.2 |
| Spiro{cyclobutane-1,2'-[5'-(4"-(2-methylallyl)-1",4"-diazepan-1"-yl)-acenaphthylen-1'(2'H)-one]}, | Example 337 | 6.021 | 361.2 |
| Spiro{cyclopentane-1,2'-[5'-(4"-(2-methylallyl)-1",4"-diazepan-1"-yl)-acenaphthylen-1'(2'H)-one]}, | Example 338 | 6.367 | 375.3 |
| Spiro{cyclohexane-1,2'-[5'-(4"-(2-methylallyl)-1",4"-diazepan-1"-yl)-acenaphthylen-1'(2'H)-one]}, | Example 339 | 6.773 | 389.2 |
| 5-(4-isopropyl-1,4-diazepan-1-yl)-2,2-dipropylacenaphthylen-1(2H)-one, | Example 340 | 7.007 | 393.3 |
| 2,2-dibutyl-5-(4-isopropyl-1,4-diazepan-1-yl)acenaphthylen-1(2H)-one, | Example 341 | 7.803 | 421.3 |
| 5-(4-isopropyl-1,4-diazepan-1-yl)-2,2-dipentylacenaphthylen-1(2H)-one, | Example 342 | 8.698 | 449.3 |
| 2,2-dibenzyl-5-(4-isopropyl-1,4-diazepan-1-yl)acenaphthylen-1(2H)-one, | Example 343 | 7.35 | 489.3 |
| Spiro{cyclobutane-1,2'-[5'-(4"-(1-methylethyl)-1",4"-diazepan-1"-yl)-acenaphthylen-1'(2'H)-one]}, | Example 344 | 5.72 | 349.3 |
| Spiro{cyclopentane-1,2'-[5'-(4'-(1-methylethyl)-1",4"-diazepan-1"-yl)-acenaphthylen-1'(2'H)-one]}, | Example 345 | 6.067 | 363.3 |
| Spiro{cyclohexane-1,2'-[5'-(4"-(1-methylethyl)-1",4"-diazepan-1"-yl)-acenaphthylen-1'(2'H)-one]}, | Example 346 | 6.507 | 377.3 |
| 2,2-dimethyl-5-{4-[4-(trifluoromethoxy)benzyl]-1,4-diazepan-1-yl}acenaphthylen-1(2H)-one, | Example 347 | 7.036 | 469.3 |
| 2,2-diethyl-5-{4-[4-(trifluoromethoxy)benzyl]-1,4-diazepan-1-yl}acenaphthylen-1(2H)-one, | Example 348 | 7.548 | 497.3 |
| 2,2-dipropyl-5-{4-(4-(trifluoromethoxy)benzyl]-1,4-diazepan-1-yl}acenaphthylen-1(2H)-one, | Example 349 | 8.243 | 525.2 |
| 2,2-dibutyl-5-{4-[4-(trifluoromethoxy)benzyl]-1,4-diazepan-1-yl}acenaphthylen-1(2H)-one, | Example 350 | 8.978 | 553.3 |
| 2,2-dipentyl-5-{4-[4-(trifluoromethoxy)benzyl]-1,4-diazepan-1-yl}acenaphthylen-1(2H)-one, | Example 351 | 9.708 | 581.4 |
| 2,2-dibenzyl-5-{4-[4-(trifluoromethoxy)benzyl]-1,4-diazepan-1-yl}acenaphthylen-1(2H)-one, | Example 352 | 8.42 | 621.2 |
| Spiro{cyclobutane-1,2'-[5'-(4"-(4-trifluoromethoxybenzyl)-1",4"-diazepan-1"-yl)-acenaphthylen-1'(2'H)-one]}, | Example 353 | 7.27 | 481.2 |
| Spiro{cyclopentane-1,2'-[5'-(4"-(4-trifluoromethylbenzyl)-1",4"-diazepan-1"-yl)-acenaphthylen-1'(2'H)-one]}, | Example 354 | 7.567 | 495.3 |
| Spiro{cyclohexane-1,2'-[5'-(4"-(4-trifluoromethoxybenzyl)-1",4"-diazepan-1"-yl)-acenaphthylen-1'(2'H)-one]}, | Example 355 | 7.904 | 509.2 |
| 5-(4-benzyl-1,4-diazepan-1-yl)-2,2-dimethylacenaphthylen-1(2H)-one, | Example 356 | 6.202 | 385.4 |
| 5-(4-benzyl-1,4-diazepan-1-yl)-2,2-diethylacenaphthylen-1(2H)-one, | Example 357 | 6.788 | 413.3 |
| 5-(4-benzyl-1,4-diazepan-1-yl)-2,2-dipropylacenaphthylen-1(2H)-one, | Example 358 | 7.619 | 441.3 |
| 5-(4-benzyl-1,4-diazepan-1-yl)-2,2-dibutylacenaphthylen-1(2H)-one, | Example 359 | 8.354 | 469.3 |
| 5-(4-benzyl-1,4-diazepan-1-yl)-2,2-dipentylacenaphthylen-1(2H)-one, | Example 360 | 9.166 | 497.4 |
| 2,2-dibenzyl-5-(4-benzyl-1,4-diazepan-1-yl)acenaphthylen-1(2H)-one, | Example 361 | 7.869 | 537.4 |
| Spiro{cyclobutane-1,2'-[5'-(4"-benzyl-1",4"-diazepan- | Example 362 | 6.489 | 397.3 |

TABLE 3-continued 1,2-dihydroacenaphthylene-1-one Compounds Synthesized and LC/MS Data

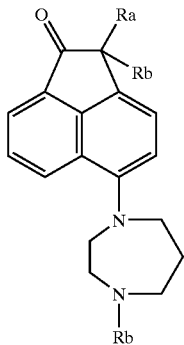

| 1,2-dihydroacenaphthylen-1-one Compounds | Example No. | HPLC[1] minutes | MS[2] (M + H) |
|---|---|---|---|
| 1"-yl)-acenaphthylen-1'(2'H)-one]}, | | | |
| Spiro{cyclopentane-1,2'-[5'-(4"-benzyl-1",4"-diazepan-1"-yl)-acenaphthyten-1'(2'H)-one]}, | Example 363 | 6.802 | 411.2 |
| Spiro{cyclohexane-1,2'-(5'-(4"-benzyl-1",4"-diazepan-1"-yl)-acenaphthylen-1'(2'H)-one]}, | Example 364 | 7.223 | 425.5 |
| 5-(4-(cyclopropylmethyl)-1,4-diazepan-1-yl]-2,2-dimethylacenaphthylen-1(2H)-one, | Example 365 | 5.612 | 349.3 |
| 5-(4-(cyclopropylmethyl)-1,4-diazepan-1-yl]-2,2-diethylacenaphthylen-1(2H)-one, | Example 366 | 6.267 | 377.3 |
| 5-[4-(cyclopropylmethyl)-1,4-diazepan-1-yl]-2,2-dipropylacenaphthylen-1(2H)-one, | Example 367 | 7.153 | 405.2 |
| 2,2-dibutyl-5-[4-(cyclopropylmethyl)-1,4-diazepan-1-yl]acenaphthylen-1(2H)-one, | Example 368 | 7.911 | 433.2 |
| 5-[4-(cyclopropylmethyl)-1,4-diazepan-1-yl]-2,2-dipentylacenaphthylen-1(2H)-one, | Example 369 | 8.76 | 461.3 |
| 2,2-dibenzyl-5-[4-(cyclopropylmethyl)-1,4-diazepan-1-yl]acenaphthylen-1(2H)-one, | Example 370 | 7.453 | 501.2 |
| Spiro{cyctobutane-1,2'-[5'-(4"-cyclopropyl-1",4"-diazepan-1"-yl)-acenaphthylen-1'(2'H)-one]}, | Example 371 | 5.909 | 361.2 |
| Spiro{cyctopentane-1,2'-(5'-(4"-cyclopropy-1",4"-diazepan-1"-yl)-acenaphthylen-1'(2'H)-one]}, | Example 372 | 6.252 | 375.3 |
| Spiro{cyclohexane-1,2'-[5'-(4"-cyclopropyl-1",4"-diazepan-1"-yl)-acenaphthylen-1'(2'H)-one]}, | Example 373 | 6.697 | 389.2 |
| 2,2-dimethyl-5-[4-(3-phenylpropyl)-1,4-diazepan-1-yl]acenaphthylen-1(2H)-one, | Example 374 | 6.744 | 413.3 |
| 2,2-diethyl-5-(4-(3-phenylpropyl)-1,4-diazepan-1-yl]acenaphthylen-1(2H)-one, | Example 375 | 7.287 | 441.2 |
| 5-[4-(3-phenylpropyl)-1,4-diazepan-1-yl]-2,2-dipropylacenaphthylen-1(2H)-one, | Example 376 | 8.107 | 469.3 |
| 2,2-dibutyl-5-[4-(3-phenylpropyl)-1,4-diazepan-1-yl]acenaphthylen-1(2H)-one, | Example 377 | 8.724 | 497.3 |
| 2,2-dipentyl-5-[4-(3-phenylpropyl)-1,4-diazepan-1-yl]acenaphthylen-1(2H)-one, | Example 378 | 9.522 | 525.3 |
| 2,2-dibenzyl-5-[4-(3-phenylpropyl)-1,4-diazepan-1-yl]acenaphthylen-1(2H)-one, | Example 379 | 8.222 | 565.3 |
| Spiro{cyclobutane-1,2'-[5'-(4"-(3-phenylpropyl)-1",4"-diazepan-1"-yl)-acenaphthylen-1'(2'H)-one)]}, | Example 380 | 7.003 | 425.2 |
| Spiro{cyclopentane-1,2'-[5'-(4"-(3-phenylpropyl)-1",4"-diazepan-1'-yl)-acenaphthylen-1'(2'H)-one]}, | Example 381 | 7.3 | 439.2 |
| Spiro{cyclohexane-1,2'-[5'-(4"-(3-phenylpropyl)-1",4"-diazepan-1"-yl)-acenaphthylen-1'(2'H)-one]}, | Example 382 | 7.672 | 453.3 |
| 2,2-dimethyl-5-[4-(2-phenylethyl)-1,4-diazepan-1-yl]acenaphthylen-1(2H)-one, | Example 383 | 6.513 | 399.2 |
| 2,2-diethyl-5-[4-(2-phenylethyl)-1,4-diazepan-1-yl]acenaphthylen-1(2H)-one, | Example 384 | 7.072 | 427.2 |
| 5-[4-(2-phenylethyl)-1,4-diazepan-1-yl]-2,2-dipropylacenaphthylen-1(2H)-one, | Example 385 | 7.837 | 455.3 |
| 2,2-dibutyl-5-[4-(2-phenylethyl)-1,4-diazepan-1-yl]acenaphthylen-1(2H)-one, | Example 386 | 8.547 | 483.4 |
| 2,2-dipentyl-5-[4-(2-phenylethyl)-1,4-diazepan-1-yl]acenaphthylen-1(2H)-one, | Example 387 | 9.409 | 511.4 |
| 2,2-dibenzyl-5-[4-(2-phenylethyl)-1,4-diazepan-1-yl]acenaphthylen-1(2H)-one, | Example 388 | 8.079 | 551.3 |
| Spiro{cyclobutane-1,2'-[5'-(4"-(2-phenylethyl)-1",4"-diazepan-1"-yl)-acenaphthylen-1'(2'H)-one]}, | Example 389 | 6.783 | 411.2 |
| Spiro(cyclopentane-1,2'-[5'-(4"-(2-phenylethyl)-1",4"- | Example 390 | 7.072 | 425.2 |

TABLE 3-continued 1,2-dihydroacenaphthylene-1-one Compounds Synthesized and LC/MS Data

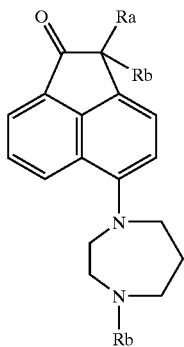

| 1,2-dihydroacenaphthylen-1-one Compounds | Example No. | HPLC[1] minutes | MS[2] (M + H) |
|---|---|---|---|
| diazepan-1"-yl)-acenaphthylen-1'(2'H)-one]}, | | | |
| Spiro{cyclohexane-1,2'-[5'-(4"-(2-phenylethyl)-1",4"-diazepan-1"-yl)-acenaphthylen-1'(2'H)-one]}, | Example 391 | 7.449 | 439.2 |
| 5-(4-isobutyl-1,4-diazepan-1-yl)-2,2-dimethylacenaphthylen-1(2H)-one, | Example 392 | 5.799 | 351.3 |
| 2,2-diethyl-5-(4-isobutyl-1,4-diazepan-1-yl)acenaphthylen-1(2H)-one, | Example 393 | 6.462 | 379.4 |
| 5-(4-isobutyl-1,4-diazepan-1-yl)-2,2-dipropylacenaphthylen-1(2H)-one, | Example 394 | 7.354 | 407.4 |
| 2,2-dibutyl-5-(4-isobutyl-1,4-diazepan-1-yl)acenaphthylen-1(2H)-one, | Example 395 | 8.101 | 435.3 |
| 5-(4-isobutyl-1,4-diazepan-1-yl)-2,2-dipentylacenaphthylen-1(2H)-one, | Example 396 | 8.816 | 4.634 |
| 2,2-dibenzyl-5-(4-isobutyl-1,4-diazepan-1-yl)acenaphthylen-1(2H)-one, | Example 397 | 7.615 | 503.4 |
| Spiro{cyclobutane-1,2'-[5'-(4"-(2-methylpropyl)-1",4"-diazepan-1"-yl)-acenaphthylen-1'(2'H)-one]}, | Example 398 | 6.1 | 363.4 |
| Spiro{cyclopentane-1,2'[5'-(4"-(2-methylpropyl)-1",4"-diazepan-1"-yl)-acenaphthylen-1'(2'H)-one]}, | Example 399 | 6.449 | 377.4 |
| 5-(4-isopentyl-1,4-diazepan-1-yl)-2,2-dimethylacenaphthylen-1(2H)-one, | Example 400 | 6.283 | 365.4 |
| 2,2'diethyl-5-(4-isopentyl-1,4-diazepan-1-yl)acenaphthylen-1(2H)-one, | Example 401 | 6.894 | 393.2 |
| 5-(4-isopentyl-1,4-diazepan-1-yl)-2,2-dipropylacenaphthylen-1(2H)-one, | Example 402 | 7.73 | 421.3 |
| 2,2-dibutyl-5-(4-isopentyl-1,4-diazepan-1-yl)acenaphthylen-1(2H)-one, | Example 403 | 8.465 | 449.3 |
| 5-(4-isopentyl-1,4-diazepan-1-yl)-2,2-dipentylacenaphthylen-1(2H)-one, | Example 404 | 9.319 | 477.5 |
| 2,2-dibenzyl-5-(4-isopentyl-1,4-diazepan-1-yl)acenaphthylen-1(2H)-one, | Example 405 | 7.965 | 517.4 |
| Spiro{cyclobutane-1,2'-[5'-(4"-(3-methylbutyl)-1",4"-diazepan-1"-yl)-acenaphthylen-1'(2'H)-one]}, | Example 406 | 6.567 | 377.3 |
| Spiro{cyclopentane-1,2'-[5'-(4"-(3-methylbutyl)-1",4"-diazepan-1"-yl)-acenaphthylen-1'(2'H)-one]}, | Example 407 | 6.901 | 391.3 |
| Spiro{cyclohexane-1,2'-[5'-(4"-(3-methylbutyl)-1",4"-diazepan-1"-yl)-acenaphthylen-1'(2'H)-one]}, | Example 408 | 7.305 | 405.4 |
| 5-[4-(cyclobutylmethyl)-1,4-diazepan-1-yl]-2,2-dimethylacenaphthylen-1(2H)-one, | Example 409 | 6.039 | 363.4 |
| 5-[4-(cyclobutylmethyl)-1,4-diazepan-1-yl]-2,2-diethylacenaphthylen-1(2H)-one, | Example 410 | 6.68 | 391.3 |
| 5-[4-(cyclobutylmethyl)-1,4-diazepan-1-yl]-2,2-dipropylacenaphthylen-1(2H)-one, | Example 411 | 7.52 | 419.4 |
| 2,2-dibutyl-5-[4-(cyclobutylmethyl)-1,4-diazepan-1-yl]acenaphthylen-1(2H)-one, | Example 412 | 8.273 | 447.4 |
| 5-[4-(cyclobutylmethyl)-1,4-diazepan-1-yl]-2,2-dipentylacenaphthylen-1(2H)-one, | Example 413 | 9.145 | 475.4 |
| Spiro{cyclobutane-1,2'-[5'-(4"-cyclobutylmethyl-1",4"-diazepan-1"-yl)-acenaphthylen-1'(2'H)-one]}, | Example 414 | 6.323 | 375.3 |
| Spiro{cyclopentane-1,2'-[5'-(4"-cyclobutylmethyl-1",4"-diazepan-1"-yl)-acenaphthylen-1'(2'H)-one]}, | Example 415 | 6.66 | 389.3 |
| Spiro{cyclohexane-1,2'-[5'-(4'cyclobutylmethyl-1',4"-diazepan-1"-yl)-acenaphthylen-1'(2'H)-one]}, | Example 416 | 7.065 | 403.3 |

TABLE 3-continued 1,2-dihydroacenaphthylene-1-one Compounds Synthesized and LC/MS Data

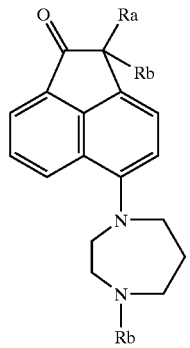

| 1,2-dihydroacenaphthylen-1-one Compounds | Example No. | HPLC[1] minutes | MS[2] (M + H) |
|---|---|---|---|

[1] LC conditions: Hewlett Packard 1100; YMC ODS-A 4.6 mm × 50 mm 5 u column at 23° C.; 10 uL injection; Solvent A: 0.05% TFA/water; Solvent B: 0.05% TFA/acetonitrile; Gratient: Time 0: 98% A; 1 min: 98% A; 7 min: 10% A, 8 min: 10% A; 8.9 min: 98% A; Post time 1 min. Flow rate 2.5 mL/min; Detection: 220 and 254 nm DAD.
[2] MS conditions: API-electrospray

[1] LC conditions: Hewlett Packard 1100; YMC ODS-A 4.6 mm×50 mm 5 u column at 23° C.; 10 uL injection; Solvent A: 0.05% TFA/water; Solvent B: 0.05% TFA/acetonitrile; Gratient: Time 0: 98% A; 1 min: 98% A; 7 min: 10% A, 8 min: 10% A; 8.9 min: 98% A; Post time 1 min. Flow rate 2.5 mL/min; Detection: 220 and 254 nm DAD.
[2] MS conditions: API-electrospray 5HT2C Receptor Binding Affinity Evaluation To determine for compounds of Formula (I) the affinity for the 5HT2C receptor, the following 5HT2C receptor binding assay was performed. A CHO (Chinese Hamster Ovary) cell line transfected with the cDNA expressing the human 5-hydroxytryptamine2C (h5HT2C) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10–25 microliter ($\mu$l) volumes. Bovine Serum Albumin (BSA) was used as the standard in the protein determination by the method of Lowry et al., (J. Biol. Chem., 193:265 (1951)). The volume of the suspended cell membranes was adjusted with 50 mM Tris.HCl buffer containing: 0.1% ascorbic acid, 10 mM pargyline and 4 mM $CaCl_2$ to give a tissue protein concentration of 1–2 mg per ml of suspension. The preparation membrane suspension (many times concentrated) was aliquoted in 1 ml volumes and stored at −70° C. until used in subsequent binding experiments.

Binding experiments were performed in a 96 well microtiter plate format, in a total volume of 200 $\mu$l. To each well was added: 60 $\mu$l of incubation buffer made in 50 mM Tris.HCl buffer, pH 7.4 and containing 4 mM $CaCl_2$; 20 $\mu$l of [$^{251}$I] DOI [1-(4-iodo-2,5-dimethoxyphenyl)-2-aminopropane] (S.A., 2200 Ci/mmol, NEN Life Science).

The dissociation constant, KD of [$^{125}$I] DOI at the human serotonin 5HT2C receptor was 0.4 nM by saturation binding with increasing concentrations of [$^{125}$I] DOI. The reaction was initiated by the final addition of 100.0 $\mu$l of tissue suspension containing 50 $\mu$g of receptor protein. Nonspecific binding was measured in the presence of 1 $\mu$M unlabeled DOI added in 20.0 $\mu$l volume. Test compounds are added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 $\mu$l Microscint-20 scintillant in a Packard TopCount® equipped with six (6) photomultiplier detectors.

Description of this method can be found in Sanders-Bush, E. et al., Putative selective 5-HT2C antagonists block serotonin 5-HT$_{1C}$ receptors in the choroid plexus, J. Pharmacol. Exper. Ther., 247: 169–173 (1988), and Akiyoshi, J., et al., Effects of antidepressants on intracellular calcium mobilization in CHO cells transfected with the human 5-HT2C receptors, Biol. Psychiatry, 39:1000–1008 (1996).

Specific binding is defined as the total radioactivity bound less the amount bound in the presence of 1 $\mu$M unlabeled DOI. Binding in the presence of varying concentrations of test drugs was expressed as percent of specific binding in the absence of drug. These results were then plotted as log % bound versus log concentration of test drug. Non linear regression analysis of data points with a computer assisted program Prism* yielded both the $IC_{50}$ and the Ki values of test compounds with 95% confidence limits. Alternatively, a linear regression line of decline of data points was plotted, from which the $IC_{50}$ value was read off the curve and the Ki value determined by solving the following equation:

$$Ki = \frac{IC_{50}}{1 + L/KD}$$

where L is the concentration of the radioactive ligand used and the KD is the dissociation constant of the ligand for the receptor, both expressed in nM.

The following compounds were evaluated according to the procedure described above for inhibition of the serotonin-displaceable serotonin-2C receptor binding. The results for 5HT2C binding affinity are reported below for DOI, and Examples 5, 11, 13, 22, 24, 28, 32, 44, 80, 85, and 88. The binding affinities for the Examples indicate that these compounds would function as agonists at the 5HT2C receptor.

| Compound Tested | 5HT2C Binding Affinity Ki (nM) |
|---|---|
| DOI | 19.48 |
| Example 5 | 131.74 |

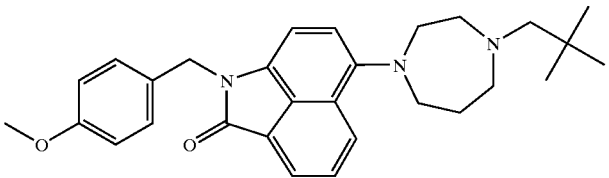

1-(4-methoxybenzyl)-6-(4-neopentyl-1,4-diazepan-1-yl)benzo[cd]indol-2(1H)-one
Example 11      165.15

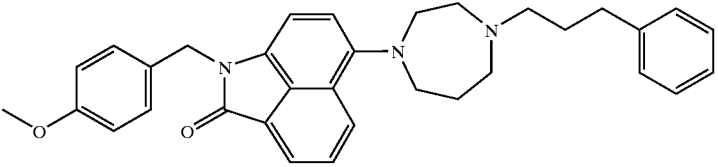

1-(4-methoxybenzyl)-6-[4-(3-phenylpropyl)-1,4-diazepan-1-yl]benzo[cd]indol-2(1H)-one
Example 13      257.23

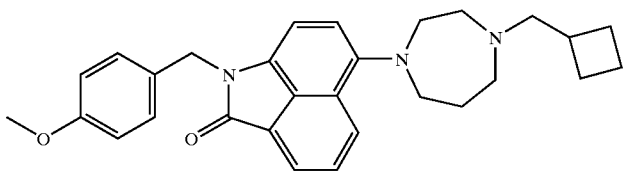

6-[4-cyclobutylmethyl)-1,4-diazepan-1-yl]-1-(4-methoxybenzyl)benzo[cd]indol-2(1H)-one
Example 22      241.48

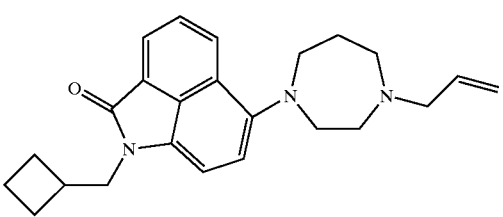

6-(4-allyl-1,4-diazepan-1-yl)-1-(cyclobutylmethyl)benzo[cd]indol-2(1H)-one
Example 24      260.26

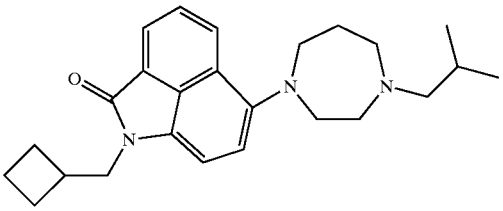

1-(cyclobutylmethyl)-6-(4-isobutyl-1,4-diazepan-1-yl)benzo[cd]indol-2(1H)-one

-continued

| Compound Tested | 5HT2C Binding Affinity Ki (nM) |
|---|---|
| Example 28 | 178.08 |

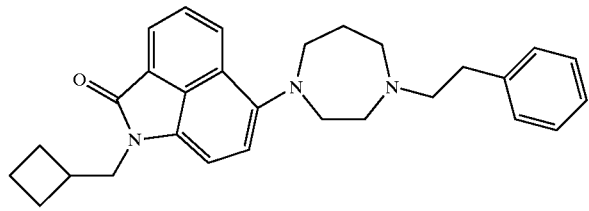

1-(cyclobutylmethyl)-6-[4-(2-phenylethyl)-1,4-diazepan-1-yl]benzo[cd]indol-2(1H)-one

| Example 32 | 256.14 |
|---|---|

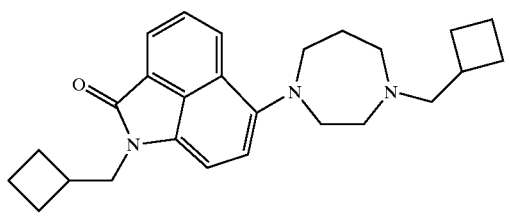

1-(cyclobutylmethyl)-6-[4-(cyclobutylmethyl)-1,4-diazepan-1-yl]benzo[cd]indol-2(1H)-one

| Example 44 | 246.88 |
|---|---|

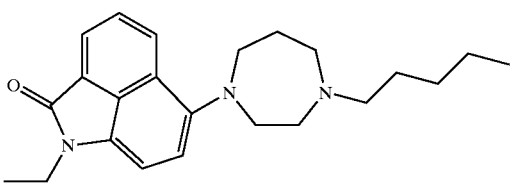

1-ethyl-6-(4-pentyl-1,4-diazepan-1-yl)benzo[cd]indol-2(1H)-one

| Example 80 | 190.2 |
|---|---|

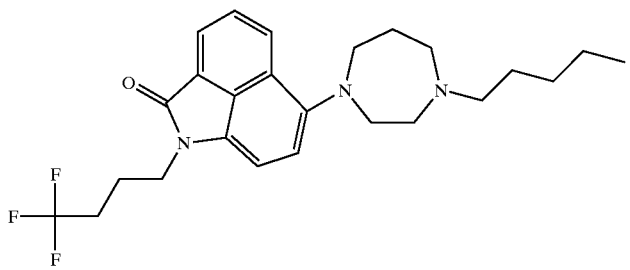

6-(4-pentyl-1,4-diazepan-1-yl)-1-(4,4,4-trifluorobutyl)benzo[cd]indol-2(1H)-one

| Example 85 | 112.13 |
|---|---|

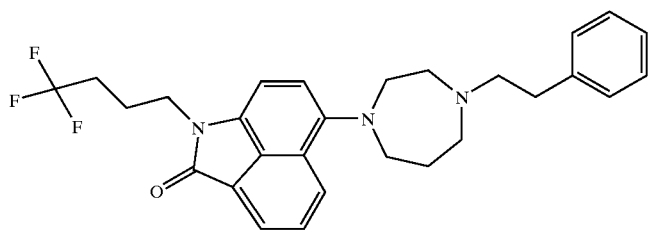

6-[4-(2-phenylethyl)-1,4-diazepan-1-yl]-1-(4,4,4-trifluorobutyl)benzo[cd]indol-2(1H)-one

| Example 88 | 242.5 |
|---|---|

| Compound Tested | 5HT2C Binding Affinity Ki (nM) |
|---|---|
| 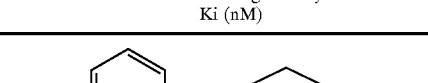 1-(4-methoxybenzyl)-6-(4-propyl-1,4-diazepan-1-yl)benzo[cd]indol-2(1H)-one | |

Although the present invention has been described above with respect to particular preferred embodiments, it will be apparent to those skilled in the art that numerous modifications and variations can be made to the present invention without departing from the scope of the present invention.

What is claimed is:

1. A compound of Formula (I) or a pharmaceutically acceptable salt thereof:

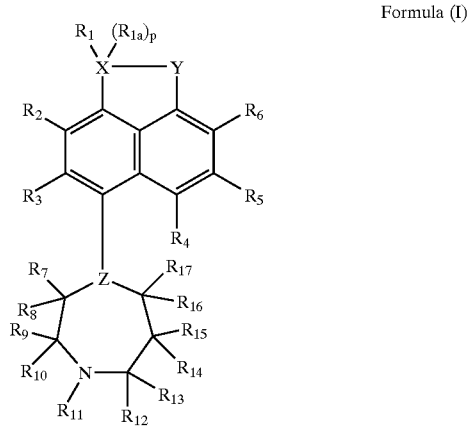

Formula (I)

wherein:

X is C or N;

Y is $CH_2$, C=O, S=O, or $SO_2$;

Z is N;

$R_1$, $R_{1a}$ and $R_{11}$ are each independently selected from hydrogen, an alkyl or alkenyl group, a $C_3$ to $C_8$ cycloalkyl group, or an arylalkyl or heteroarylalkyl group, or when X is C, $R_1$ and $R_{1a}$ may form together with the carbon atom to which they are attached a $C_3$ to $C_8$ cycloalkyl group in spiro form;

$R_2$, $R_3$, $R_4$, $R_5$ and $R_6$ are each independently selected from hydrogen, halogen, an alkyl, alkenyl, or alkynyl group, a $C_3$ to $C_8$ cycloalkyl group, or a cycloheteroalkyl, aryl, heteroaryl, arylalkyl, alkanoyl, CN, CHO, alkoxy, aryloxy, heteroaryloxy, alkenyloxy, alkynyloxy, OCOalkyl, OCOaryl, OCONR$_{18}$, COOH, COOalkyl, COOaryl, CONR$_{18}$R$_{19}$, CONHOH, NR$_{18}$R$_{19}$, SO$_2$NR$_{18}$R$_{19}$, NO$_2$, or NH$_2$, or OH group, where $R_{18}$ and $R_{19}$ are each independently selected from hydrogen, an alkyl, alkenyl, or alkynyl group, a $C_3$ to $C_8$ cycloalkyl group, or an aryl, heteroaryl, arylalkyl, perfluoroalkyl, COalkyl, COaryl, COheteroaryl, COOalkyl, COOaryl, COOheteroaryl, CONHalkyl, CON(alkyl)$_2$, CONHaryl, CONHheteroaryl, cycloheteroalkyl, S(O)$_m$-alkyl or S(O)$_m$-aryl group, where m is 0, 1 or 2;

$R_7$, $R_8$, $R_9$, $R_{10}$, $R_{12}$, $R_{13}$, $R_{14}$, $R_{15}$, $R_{16}$, and $R_{17}$ are each independently selected from hydrogen, an alkyl, alkenyl or alkynyl group, a $C_3$ to $C_8$ cycloalkyl group, or a cycloheteroalkyl, aryl, arylalkyl or heteroaryl group;

p is 1 when X is carbon, and p is zero when X is nitrogen;

wherein aryl is

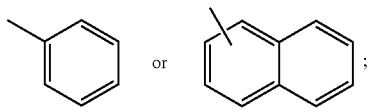

cycloheteroalkyl is

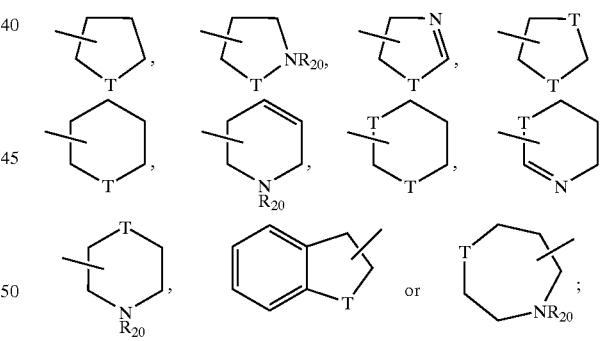

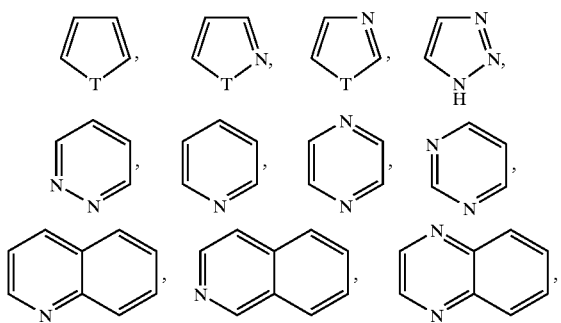

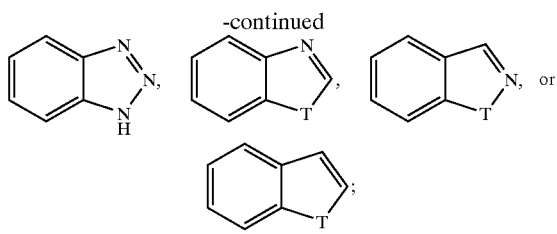

where a carbon of the cycloheteroalkyl may optionally be double bonded to either O or S, where T is $NR_{18}$, O, or S, and where $R_{20}$ is hydrogen, halogen, an alkyl, alkenyl or alkynyl group, a $C_3$ to $C_8$ cycloalkyl group, a cycloheteroalkyl, aryl, arylalkyl, heteroaryl, alkanoyl, CN, CHO, alkoxy, aryloxy, heteroaryloxy, alkenyloxy, alkynyloxy, OCOalkyl, OCOOaryl, OCONR$_{18}$, COOH, COOalkyl, COOaryl, CONR$_{18}$ R$_{19}$, CONHOH, NR$_{18}$R$_{19}$, SO$_2$NR$_{18}$R$_{19}$, NO$_2$, NH$_2$, OH, S(O)$_m$-alkyl or S(O)$_m$-aryl group, where the alkyl or alkoxy groups of $R_{20}$ may be optionally substituted with one or more halogens; and wherein any alkyl, alkenyl, alkynyl, aryl, arylalkyl, heteroaryl or cycloalkyl moiety of $R_1$, $R_{1a}$, or $R_2$ to $R_{17}$ may optionally be substituted with one to three groups independently selected from $R_{20}$ and where any cycloheteroaryl moiety of $R_1$, $R_{1a}$, or $R_2$ to $R_{17}$ may optionally be substituted with one to six groups independently selected from $R_{20}$.

2. The compound of claim 1 wherein $R_2$, $R_3$, $R_4$, $R_5$ and $R_6$ are hydrogen.

3. The compound of claim 2 wherein the moiety:

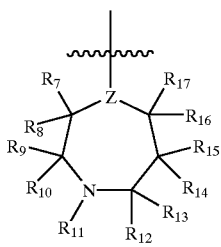

of Formula (I) is:

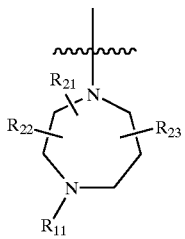

wherein $R_{21}$, $R_{22}$, and $R_{23}$ are each independently selected from hydrogen, an alkyl, alkenyl or alkynyl group, a $C_3$ to $C_8$ cycloalkyl group, or a cycloheteroalkyl, aryl, arylalkyl or heteroaryl group.

4. The compound of claim 3 wherein $R_{21}$, $R_{22}$, and $R_{23}$ are hydrogen.

5. The compound of claim 3 wherein $R_1$ and $R_{1a}$ are independently selected from hydrogen; an unsubstituted linear or branched saturated $C_1$ to $C_6$ alkyl group; a $C_1$ to $C_6$ linear or branched saturated alkyl group substituted with one to three halogens, $C_1$ to $C_3$ alkoxy groups, halogenated $C_1$ to $C_3$ alkoxy groups, or combinations thereof; a unsubstituted or substituted $C_3$ to $C_{10}$ alkenyl group; an unsubstituted $C_3$ to $C_6$ cycloalkyl group; a $C_3$ to $C_6$ cycloalkyl group substituted with one to three $C_1$ to $C_3$ alkyl groups; an unsubstituted phenyl $C_1$ to $C_3$ alkyl group; or a phenyl $C_1$ to $C_3$ alkyl group substituted with one to three $C_1$ to $C_3$ alkoxy groups or halogenated $C_1$ to $C_3$ alkoxy groups; or when X is C, $R_1$, and $R_{1a}$ may form together with the carbon atom to which they are attached a $C_4$ to $C_6$ cycloalkyl group in spiro form.

6. The compound of claim 5 wherein $R_{11}$ is selected from hydrogen; an unsubstituted linear or branched saturated $C_1$ to $C_6$ alkyl group; a $C_1$ to $C_6$ linear or branched saturated alkyl group substituted with one to three halogens, $C_1$ to $C_3$ alkoxy groups, halogenated $C_1$ to $C_3$ alkoxy groups, CN, COOalkyl, COOaryl or combinations thereof; a unsubstituted or substituted $C_3$ to $C_{10}$ alkenyl group; an unsubstituted $C_3$ to $C_6$ cycloalkyl group; a $C_3$ to $C_6$ cycloalkyl group substituted with one to three $C_1$ to $C_3$ alkyl groups; an unsubstituted phenyl $C_1$ to $C_3$ alkyl group; or a phenyl $C_1$ to $C_3$ alkyl group substituted with one to three $NO_2$ groups, $C_1$ to $C_3$ alkoxy groups or halogenated $C_1$ to $C_3$ alkoxy groups.

7. The compound of claim 3 wherein Y is C=O or $SO_2$.

8. The compound of claim 1 wherein X is N and Y is C=O or $CH_2$.

9. The compound of claim 8 wherein $R_2$, $R_3$, $R_4$, $R_5$ and $R_6$ are hydrogen.

10. The compound of claim 9 wherein each of $R_7$, $R_8$, $R_9$, $R_{10}$, $R_{12}$, $R_{13}$, $R_{14}$, $R_{15}$, $R_{16}$, and $R_{17}$ are hydrogen.

11. The compound of claim 10 wherein $R_1$ is hydrogen; an unsubstituted linear or branched saturated $C_1$ to $C_6$ alkyl group; a $C_1$ to $C_6$ linear or branched saturated alkyl group substituted with one to three halogens; an unsubstituted $C_3$ to $C_6$ cycloalkyl group; a $C_3$ to $C_6$ cycloalkyl group substituted with one to three $C_1$ to $C_3$ alkyl groups; a unsubstituted or substituted $C_3$ to $C_{10}$ alkenyl group; an unsubstituted phenyl $C_1$ to $C_3$ alkyl group; or a phenyl $C_1$ to $C_3$ alkyl group substituted with one to three $C_1$ to $C_3$ alkoxy groups.

12. The compound of claim 11 wherein $R_1$ is selected from methyl, ethyl, propyl, butyl, pentyl, hexyl, trifluorobutyl, trifluoropropyl, benzyl, methoxybenzyl, phenylethyl, phenylpropyl, cyclopropylmethyl, cyclobutylmethyl, cyclohexylmethyl, or allyl.

13. The compound of claim 10 wherein $R_{11}$ is selected from hydrogen; an unsubstituted linear or branched saturated $C_1$ to $C_6$ alkyl group; a $C_1$ to $C_6$ linear or branched saturated alkyl group substituted with one to three halogens, $C_1$ to $C_3$ alkoxy groups, CN, COOalkyl, COOaryl or combinations thereof; an unsubstituted $C_3$ to $C_6$ cycloalkyl group; a $C_3$ to $C_6$ cycloalkyl group substituted with one to three $C_1$ to $C_3$ alkyl groups; a unsubstituted or substituted $C_3$ to $C_{10}$ alkenyl group; an unsubstituted phenyl $C_1$ to $C_3$ alkyl group; or a phenyl $C_1$ to $C_3$ alkyl group substituted with one to three $NO_2$ groups, $C_1$ to $C_3$ alkoxy groups, or $C_1$ to $C_3$ halogenated alkoxy groups.

14. The compound of claim 13 wherein $R_{11}$ is selected from methyl, ethyl, propyl, butyl, pentyl, hexyl, trifluorobutyl, trifluoropropyl, benzyl, methoxybenzyl, trifluoromethoxybenzyl, nitrobenzyl, phenylethyl, phenylpropyl, cyclopropylmethyl, cyclobutylmethyl, cyclohexylmethyl, cyclohexyl, allyl, methylallyl, 3,7-dimethylocta-2,6-dienyl, ethoxyethyl, cyanomethyl, cyanobutyl, ethoxycarbonylmethyl, or benzyloxycarbonylmethyl.

15. The compound of claim 10 wherein Y is C=O.

16. The compound of claim 8 selected from at least one of:

6-(4-butyl-1,4-diazepan-1-yl)-1-(4-methoxybenzyl) benzo[cd]indol-2(1H)-one;

1-(4-methoxybenzyl)-6-(4-pentyl-1,4-diazepan-1-yl)
benzo[cd]indol-2(1H)-one;
6-(4-isobutyl-1,4-diazepan-1-yl)-1-(4-methoxybenzyl)
benzo[cd]indol-2(1H)-one;
1-(4-methoxybenzyl)-6-(4-neopentyl-1,4-diazepan-1-yl)
benzo[cd]indol-2(1H)-one;
1-(4-methoxybenzyl)-6-[4-(3,3,3-trifluoropropyl)-1,4-
diazepan-1-yl]benzo[cd]indol-2(1H)-one;
1-(4-methoxybenzyl)-6-[4-(4,4,4-trifluorobutyl)-1,4-
diazepan-1-yl]benzo[cd]indol-2(1H)-one;
ethyl {4-[1-(4-methoxybenzyl)-2-oxo-1,2-dihydrobenzo
[cd]indol-6-yl]-1,4-diazepan-1-yl}acetate;
1-(4-methoxybenzyl)-6-[4-(2-phenylethyl)-1,4-diazepan-
1-yl]benzo[cd]indol-2(1H)-one;
6-(4-benzyl-1,4-diazepan-1-yl)-1-(4-methoxybenzyl)
benzo[cd]indol-2(1H)-one;
1-(4-methoxybenzyl)-6-[4-(3-phenylpropyl)-1,4-
diazepan-1-yl]benzo[cd]indol-2(1H)-one;
4-{4-[1-(4-methoxybenzyl)-2-oxo-1,2-dihydrobenzo[cd]
indol-6-yl]-1,4-diazepan-1-yl}butanenitrile;
6-[4-(cyclobutylmethyl)-1,4-diazepan-1-yl]-1-(4-
methoxybenzyl)benzo[cd]indol-2(1H)-one;
6-{4-[(2E)-3,7-dimethylocta-2,6-dienyl]-1,4-diazepan-1-
yl}-1-(4-methoxybenzyl)benzo[cd]indol-2(1H)-one;
6-(4-isopentyl-1,4-diazepan-1-yl)-1-(4-methoxybenzyl)
benzo[cd]indol-2(1H)-one;
benzyl {4-[1-(4-methoxybenzyl)-2-oxo-1,2-
dihydrobenzo[cd]indol-6-yl]-1,4-diazepan-1-
yl}acetate;
6-[4-(cyclopropylmethyl)-1,4-diazepan-1-yl]-1-(4-
methoxybenzyl) benzo[cd]indol-2(1H)-one;
1-(4-methoxybenzyl)-6-[4-(3-nitrobenzyl)-1,4-diazepan-
1-yl]benzo[cd]indol-2(1H)-one;
1-(2-phenylethyl)-6-(4-propyl-1,4-diazepan-1- yl)benzo
[cd]indol-2(1H)-one;
6-(4-butyl-1,4-diazepan-1-yl)-1-(2-phenylethyl)benzo
[cd]indol-2(1H)-one;
6-(4-allyl-1,4-diazepan-1-yl)-1-(2-phenylethyl)benzo[cd]
indol-2(1H)-one;
6-(4-pentyl-1,4-diazepan-1-yl)-1-(2-phenylethyl)benzo
[cd]indol-2(1H)-one;
6-(4-isobutyl-1,4-diazepan-1-yl)-1-(2-phenylethyl)benzo
[cd]indol-2(1H)-one;
1-(2-phenylethyl)-6-[4-(3,3,3-trifluoropropyl)-1,4-
diazepan-1-yl]benzo[cd]indol-2(1H)-one;
1-(2-phenylethyl)-6-[4-(4,4,4-trifluorobutyl)-1,4-
diazepan-1-yl]benzo[cd]indol-2(1H)
ethyl {4-[2-oxo-1-(2-phenylethyl)-1,2-dihydro benzo[cd]
indol-6-yl]-1,4-diazepan-1-yl}acetate;
1-(2-phenylethyl)-6-[4-(2-phenylethyl)-1,4-diazepan-1-
yl]benzo[cd]indol-2(1H)-one;
4-{4-[2-oxo-1-(2-phenylethyl)-1,2-dihydrobenzo [cd]
indol-6-yl]-1,4-diazepan-1-yl}butanenitrile;
1-(2-phenylethyl)-6-[4-(3-phenylpropyl)-1,4-diazepan-1-
yl]benzo[cd]indol-2(1H)-one;
6-[4-(cyclobutylmethyl)-1,4-diazepan-1-yl]-1-(2-
phenylethyl)benzo[cd]indol-2(1H)-one;
6-[4-(2-ethoxyethyl)-1,4-diazepan-1-yl]-1-(2-
phenylethyl)benzo[cd]indol-2(1H)-one;
6-(4-isopentyl-1,4-diazepan-1-yl)-1-(2-phenylethyl)
benzo[cd]indol-2(1H)-one;
benzyl {4-[2-oxo-1-(2-phenylethyl)-1,2-dihydrobenzo
[cd]indol-6-yl]-1,4-diazepan-1-yl}acetate;
6-[4-(cyclohexylmethyl)-1,4-diazepan-1-yl]-1-(2-
phenylethyl)benzo[cd]indol-2(1H)-one;
6-[4-(cyclopropylmethyl)-1,4-diazepan-1-yl]-1-(2-
phenylethyl)benzo[cd]indol-2(1H)-one;
6-[4-(2-nitrobenzyl)-1,4-diazepan-1-yl]-1-(2-
phenylethyl)benzo[cd]indol-2(1H)-one;
6-[4-(4-methoxybenzyl)-1,4-diazepan-1-yl]-1-(2-
phenylethyl)benzo[cd]indol-2(1H)-one; or a pharma-
ceutically acceptable salt thereof.

17. The compound of claim 8 selected from at least one of:

1-(cyclobutylmethyl)-6-(4-ethyl-1,4-diazepan-1-yl)benzo
[cd]indol-2(1H)-one;
1-(cyclobutylmethyl)-6-(4-propyl-1,4-diazepan-1-yl)
benzo[cd]indol-2(1H)-one;
6-(4-butyl-1,4-diazepan-1-yl)-1-(cyclobutylmethyl)
benzo[cd]indol-2(1H)-one;
6-(4-allyl-1,4-diazepan-1-yl)-1-(cyclobutylmethyl)benzo
[cd]indol-2(1H)-one;
1-(cyclobutylmethyl)-6-(4-pentyl-1,4-diazepan-1-yl)
benzo[cd]indol-2(1H)-one;
1-(cyclobutylmethyl)-6-(4-isobutyl-1,4-diazepan-1-yl)
benzo[cd]indol-2(1H)-one,
1-(cyclobutylmethyl)-6-[4-(3,3,3-trifluoropropyl)-1,4-
diazepan-1-yl]benzo[cd]indol-2(1H)-one;
1-(cyclobutylmethyl)-6-[4-(4,4,4-trifluorobutyl)-1,4-
diazepan-1-yl]benzo[cd]indol-2(1H)-one;
ethyl {4-[1-(cyclobutylmethyl)-2-oxo-1,2-dihydrobenzo
[cd]indol-6-yl]-1,4-diazepan-1-yl}acetate;
1-(cyclobutylmethyl)-6-[4-(2-phenylethyl)-1,4-diazepan-
1-yl] benzo [cd]indol-2(1H)-one;
6-(4-benzyl -1,4-diazepan-1-yl)-1-(cyclobutylmethyl)
benzo[cd]indol-2(1H)-one;
4-{4-[1-(cyclobutylmethyl)-2-oxo-1,2-dihydrobenzo [cd]
indol-6-yl]-1,4-diazepan-1-yl}butanenitrile;
1-(cyclobutylmethyl)-6-[4-(3-phenylpropyl)-1,4-
diazepan-1-yl]benzo[cd]indol-2(1H)-one;
1-(cyclobutylmethyl)-6-[4-(cyclobutylmethyl)-1,4-
diazepan-1-yl]benzo[cd]indol-2(1H)-one;
1-(cyclobutylmethyl)-6-[4-(2-ethoxyethyl)-1,4-diazepan-
1-yl]benzo[cd]indol-2(1H)-one;
1-(cyclobutylmethyl)-6-{4-[(2E)-3,7-dimethylocta-2,6-
dienyl]-1,4-diazepan-1-yl}benzo[cd]indol-2(1H)-one;
1-(cyclobutylmethyl)-6-(4-isopentyl-1,4-diazepan-1-yl)
benzo[cd]indol-2(1H)-one;
benzyl {4-[1-(cyclobutylmethyl)-2-oxo-1,2-
dihydrobenzo[cd]indol-6-yl]-1,4-diazepan-1-
yl}acetate;
1-(cyclobutylmethyl)-6-[4-(cyclohexylmethyl)-1,4-
diazepan-1-yl]benzo[cd]indol-2(1H)-one;
1-(cyclobutylmethyl)-6-[4-(cyclopropylmethyl)-1,4-
diazepan-1-yl]benzo[cd]indol-2(1H)-one;
1-(cyclobutylmethyl)-6-[4-(3-nitrobenzyl)-1,4-diazepan-
1-yl]benzo[cd]indol-2(1H)-one;
1-(cyclohexylmethyl)-6-(4-propyl-1,4-diazepan-1-yl)
benzo[cd]indol-2(1H)-one;
6-(4-butyl-1,4-diazepan-1-yl)-1-(cyclohexylmethyl)
benzo[cd]indol-2(1H)-one;
6-(4-allyl-1,4-diazepan-1-yl)-1-(cyclohexylmethyl)benzo
[cd]indol-2(1H)-one;
1-(cyclohexylmethyl)-6-(4-pentyl-1,4-diazepan-1-yl)
benzo[cd]indol-2(1H)-one;

1-(cyclohexylmethyl)-6-(4-isobutyl-1,4-diazepan-1-yl) benzo[cd]indol-2(1H)-one;
1-(cyclohexylmethyl)-6-[4-(3,3,3-trifluoropropyl)-1,4-diazepan-1-yl]benzo[cd]indol-2(1H)-one;
1-(cyclohexylmethyl)-6-[4-(4,4,4-trifluorobutyl)-1,4-diazepan-1-yl]benzo[cd]indol-2(1H)-one;
6-(4-cyclohexyl-1,4-diazepan-1-yl)-1-(cyclohexylmethyl)benzo[cd]indol-2(1H)-one;
1-(cyclohexylmethyl)-6-[4-(2-phenylethyl)-1,4-diazepan-1-yl]benzo[cd]indol-2(1H)-one
4-{4-[1-(cyclohexylmethyl)-2-oxo-1,2-dihydrobenzo[cd]indol-6-yl]-1,4-diazepan-1-yl}butanenitrile;
6-[4-(cyclobutylmethyl)-1,4-diazepan-yl]-1-(cyclohexylmethyl)benzo[cd]indol-2(1H)-one;
1-(cyclohexylmethyl)-6-[4-(2-ethoxyethyl)-1,4-diazepan-1-yl]benzo[cd]indol-2(1H)-one;
1-(cyclohexylmethyl)-6-(4-isopentyl-1,4-diazepan-1-yl) benzo[cd]indol-2(1H)-one;
1-(cyclohexylmethyl)-6-[4-(cyclohexylmethyl)-1,4-diazepan-1-yl]benzo[cd]indol-2(1H)-one;
1-(cyclohexylmethyl)-6-[4-(cyclopropylmethyl)-1,4-diazepan-1-yl]benzo[cd]indol-2(1H)-one;
{4-[1-(cyclohexylmethyl)-2-oxo-1,2-dihydrobenzo[cd] indol-6-yl]-1,4-diazepan-1-yl}acetonitrile;
1-(cyclohexylmethyl)-6-[4-(3-nitrobenzyl)-1,4-diazepan-1-yl]benzo[cd]indol-2(1H)-one;
1-(cyclohexylmethyl)-6-[4-(4-isopropyl-1,4-diazepan-1-yl) benzo[cd]indol-2(1H)-one; or
1-(cyclohexylmethyl)-6-[4-(2-nitrobenzyl)-1,4-diazepan-1-yl]benzo[cd]indol-2(1H)-one; or a pharmaceutically acceptable salt thereof.

18. The compound of claim 8 selected from at least one of:

1-ethyl-6-(4-ethyl-1,4-diazepan-1-yl)benzo[cd]indol-2 (1H)-one;
1-ethyl-6-(4-propyl-1,4-diazepan-1-yl)benzo [cd]indol-2 (1H)-one;
6-(4-butyl-1,4-diazepan-1-yl)-1-ethylbenzo[cd]indol-2 (1H)-one;
6-(4-allyl-1,4-diazepan-1-yl)-1-ethylbenzo[cd]indol-2 (1H)-one;
1-ethyl-6-(4-pentyl-1,4-diazepan-1-yl)benzo[cd]indol-2 (1H)-one;
1-ethyl-6-(4-isobutyl-1,4-diazepan-1-yl) benzo[cd]indol-2(1H)-one;
1-ethyl-6-[4-(3,3,3-trifluoropropyl)-1,4-diazepan-1-yl] benzo[cd]indol-2(1H)-one;
1-ethyl-6-[4-(4,4,4-trifluorobutyl)-1,4-diazepan-1-yl] benzo[cd]indol-2(1H)-one;
ethyl [4-(1-ethyl-2-oxo-1,2-dihydrobenzo[cd]indol-6-yl)-1,4-diazepan-1-yl]acetate;
6-(4-cyclohexyl-1,4-diazepan-1-yl)-1-ethylbenzo[cd] indol-2(1H)-one;
1-ethyl-6-[4-(2-phenylethyl)-1,4-diazepan-1-yl]benzo [cd]indol-2(1H)-one;
6-(4-benzyl-1,4-diazepan-1-yl)-1-ethylbenzo[cd]indol-2 (1H)-one;
4-[4-(1-ethyl-2-oxo-1,2-dihydrobenzo[cd]indol-6-yl)-1, 4-diazepan-1-yl]butanenitrile;
1-ethyl-6-[4-(3-phenylpropyl)-1,4-diazepan-1-yl]benzo [cd]indol-2(1H)-one;
6-[4-(cyclobutylmethyl)-1,4-diazepan-1-yl]-1-ethylbenzo [cd]indol-2(1H)-one;
6-[4-(2-ethoxyethyl)-1,4-diazepan-1-yl]-1-ethylbenzo [cd]indol-2(1H)-one;
6-{4-[(2E)-3,7-dimethylocta-2,6-dienyl]-1,4-diazepan-1-yl}-1-ethylbenzo[cd]indol-2(1H)-one;
1-ethyl-6-(4-isopentyl-1,4-diazepan-1-yl)benzo[cd]indol-2(1H)-one;
benzyl [4-(1-ethyl-2-oxo-1,2-dihydrobenzo[cd]indol-6-yl)-1,4-diazepan-1-yl]acetate;
6-[4-(cyclohexylmethyl)-1,4-diazepan-1-yl]-1-ethylbenzo[cd]indol-2(1H)-one;
6-[4-(cyclopropylmethyl)-1,4-diazepan-1-yl]-1-ethylbenzo[cd]indol-2(1H)-one;
1-ethyl-6-[4-(3-nitrobenzyl)-1,4-diazepan-1-yl]benzo[cd] indol-2(1H)-one;
1-isobutyl-6-(4-propyl-1,4-diazepan-1-yl)benzo[cd] indol-2(1H)-one;
6-(4-butyl-1,4-diazepan-1-yl)-1-isobutylbenzo[cd]indol-2(1H)-one;
6-(4-allyl-1,4-diazepan-1-yl)-1-isobutylbenzo[cd]indol-2 (1H)-one;
1-isobutyl-6-[4-(3,3,3-trifluoropropyl)-1,4-diazepan-1-yl]benzo[cd]indol-2(1H)-one;
1-isobutyl-6-[4-(4,4,4-trifluorobutyl)-1,4-diazepan-1-yl] benzo[cd]indol-2(1H)-one;
ethyl [4-(1-isobutyl-2-oxo-1,2-dihydrobenzo[cd]indol-6-yl)-1,4-diazepan-1-yl]acetate;
1-isobutyl-6-[4-(2-phenylethyl)-1,4-diazepan-1-yl]benzo [cd]indol-2(1H)-one;
6-(4-benzyl-1,4-diazepan-1-yl)-1-isobutylbenzo[cd] indol-2(1H)-one;
4-[4-(1-isobutyl-2-oxo-1,2-dihydrobenzo[cd]indol-6-yl)-1,4-diazepan-1-yl]butanenitrile;
1-isobutyl-6-[4-(3-phenylpropyl)-1,4-diazepan-1-yl] benzo[cd]indol-2(1H)-one;
6-[4-(cyclobutylmethyl)-1,4-diazepan-1-yl]-1-isobutylbenzo[cd]indol-2(1H)-one;
6-[4-(2-ethoxyethyl)-1,4-diazepan-1-yl]-1-isobutylbenzo [cd]indol-2(1H)-one;
benzyl [4-(1-isobutyl-2-oxo-1,2-dihydrobenzo[cd]indol-6-yl)-1,4-diazepan-1-yl]acetate;
6-[4-(cyclopropylmethyl)-1,4-diazepan-1-yl]-1-isobutylbenzo[cd]indol-2(1H)-one;
1-isobutyl-6-[4-(3-nitrobenzyl)-1,4-diazepan-1-yl]benzo [cd]indol-2(1H)-one;
6-(4-ethyl-1,4-diazepan-1-yl)-1-(4,4,4-trifluorobutyl) benzo[cd]indol-2(1H)-one;
6-(4-propyl-1,4-diazepan-1-yl)-1-(4,4,4-trifluorobutyl) benzo[cd]indol-2(1H)-one;
6-(4-allyl-1,4-diazepan-1-yl)-1-(4,4,4-trifluorobutyl) benzo[cd]indol-2(1H)-one;
6-(4-pentyl-1,4-diazepan-1-yl)-1-(4,4,4-trifluorobutyl) benzo[cd]indol-2(1H)-one;
6-(4-isobutyl-1,4-diazepan-1-yl)-1-(4,4,4-trifluorobutyl) benzo[cd]indol-2(1H)-one;
1-(4,4,4-trifluorobutyl)-6-[4-(3,3,3-trifluoropropyl) -1,4-diazepan-1-yl]benzo[cd]indol-2(1H)-one;
1-(4,4,4-trifluorobutyl)-6-[4-(4,4,4-trifluorobutyl)-1,4-diazepan-1-yl]benzo[cd]indol-2(1H)-one;
ethyl {4-[2-oxo-1-(4,4,4-trifluorobutyl)-1,2-dihydrobenzo[cd]indol-6-yl]-1,4-diazepan-1-yl}acetate;
6-[4-(2-phenylethyl)-1,4-diazepan-1-yl]-1-(4,4,4-trifluorobutyl)benzo[cd]indol-2(1H)-one;

6-(4-benzyl-1,4-diazepan-1-yl)-1-(4,4,4-trifluorobutyl)benzo[cd]indol-2(1H)-one;

4-{4-[2-oxo-1-(4,4,4-trifluorobutyl)-1,2-dihydrobenzo[cd]indol-6-yl]-1,4-diazepan-1-yl}butanenitrile;

1-(4-methoxybenzyl)-6-(4-propyl-1,4-diazepan-1-yl)benzo[cd]indol-2(1H)-one;

6-[4-(cyclobutylmethyl)-1,4-diazepan-1-yl]-1-(4,4,4-trifluorobutyl)benzo[cd]indol-2(1H)-one;

6-[4-(2-ethoxyethyl)-1,4-diazepan-1-yl]-1-(4,4,4-trifluorobutyl)benzo[cd]indol-2(1H)-one;

6-(4-isopentyl-1,4-diazepan-1-yl)-1-(4,4,4-trifluorobutyl)benzo[cd]indol-2(1H)-one;

benzyl {4-[2-oxo-1-(4,4,4-trifluorobutyl)-1,2-dihydrobenzo[cd]indol-6-yl]-1,4-diazepan-1-yl}acetate;

6-[4-(3-phenylpropyl)-1,4-diazepan-1-yl]-1-(4,4,4-trifluorobutyl)benzo[cd]indol-2(1H)-one;

6-[4-(cyclopropylmethyl)-1,4-diazepan-1-yl]-1-(4,4,4-trifluorobutyl)benzo[cd]indol-2(1H)-one;

6-[4-(3-nitrobenzyl)-1,4-diazepan-1-yl]-1-(4,4,4-trifluorobutyl)benzo[cd]indol-2(1H)-one;

6-(4-propyl-1,4-diazepan-1-yl)-1-(3,3,3-trifluoropropyl)benzo[cd]indol-2(1H)-one;

6-(4-butyl-1,4-diazepan-1-yl)-1-(3,3,3-trifluoropropyl)benzo[cd]indol-2(1H)-one;

6-(4-isobutyl-1,4-diazepan-1-yl)-1-(3,3,3-trifluoropropyl)benzo[cd]indol-2(1H)-one;

1-(3,3,3-trifluoropropyl)-6-[4-(3,3,3-trifluoropropyl)-1,4-diazepan-1-yl]benzo[cd]indol-2(1H)-one;

6-[4-(4,4,4-trifluorobutyl)-1,4-diazepan-1-yl]-1-(3,3,3-trifluoropropyl)benzo[cd]indol-2(1H)-one;

6-[4-(2-phenylethyl)-1,4-diazepan-1-yl]-1-(3,3,3-trifluoropropyl)benzo[cd]indol-2(1H)-one;

4-{4-[2-oxo-1-(3,3,3-trifluoropropyl)-1,2-dihydrobenzo[cd]indol-6-yl]-1,4-diazepan-1-yl}butanenitrile;

6-[4-(3-phenylpropyl)-1,4-diazepan-1-yl]-1-(3,3,3-trifluoropropyl)benzo[cd]indol-2(1H)-one;

6-[4-(cyclobutylmethyl)-1,4-diazepan-1-yl] 1-(3,3,3-trifluoropropyl)benzo[cd]indol-2(1H)-one;

6-[4-(2-ethoxyethyl)-1,4-diazepan-1-yl]-1-(3,3,3-trifluoropropyl)benzo[cd]indol-2(1H)-one;

6-(4-isopentyl-1,4-diazepan-1-yl)-1-(3,3,3-trifluoropropyl)benzo[cd]indol-2(1H)-one;

benzyl {4-[2-oxo-1-(3,3,3-trifluoropropyl)-1,2-dihydrobenzo[cd]indol-6-yl]-1,4-diazepan-1-yl}acetate;

6-[4-(cyclopropylmethyl)-1,4-diazepan-1-yl]-1-(3,3,3-trifluoropropyl)benzo[cd]indol-2(1H)-one;

6-(4-isopropyl-1,4-diazepan-1-yl)-1-(3,3,3-trifluoropropyl)benzo[cd]indol-2(1H)-one;

6-[4-(2-nitrobenzyl)-1,4-diazepan-1-yl]-1-(3,3,3-trifluoropropyl)benzo[cd]indol-2(1H)-one;

6-[4-(4-methoxybenzyl)-1,4-diazepan-1-yl]-1-(3,3,3-trifluoropropyl)benzo[cd]indol-2(1H)-one;

6-(4-butyl-1,4-diazepan-1-yl)-1-isopentylbenzo[cd]indol-2(1H)-one;

6-(4-allyl-1,4-diazepan-1-yl)-1-isopentylbenzo[cd]indol-2(1H)-one;

1-isopentyl-6-(4-pentyl-1,4-diazepan-1-yl)benzo[cd]indol-2(1H)-one;

6-(4-isobutyl-1,4-diazepan-1-yl)-1-isopentylbenzo[cd]indol-2(1H)-one;

1-isopentyl-6-[4-(3,3,3-trifluoropropyl)-1,4-diazepan-1-yl]benzo[cd]indol-2(1H)-one;

ethyl [4-(1-isopentyl-2-oxo-1,2-dihydrobenzo[cd]indol-6-yl)-1,4-diazepan-1-yl]acetate;

1-isopentyl-6-[4-(2-phenylethyl)-1,4-diazepan-1-yl]benzo[cd]indol-2(1H)-one;

4-[4-(1-isopentyl-2-oxo-1,2-dihydrobenzo[cd]indol-6-yl)-1,4-diazepan-1-yl]butanenitrile;

1-isopentyl-6-[4-(3-phenylpropyl)-1,4-diazepan-1-yl]benzo[cd]indol-2(1H)-one;

6-[4-(cyclobutylmethyl)-1,4-diazepan-1-yl]-1-isopentylbenzo[cd]indol-2(1H)-one;

6-[4-(2-ethoxyethyl)-1,4-diazepan-1-yl]-1-isopentylbenzo[cd]indol-2(1H)-one;

1-isopentyl-6-(4-isopentyl-1,4-diazepan-1-yl)benzo[cd]indol-2(1H)-one;

benzyl [4-(1-isopentyl-2-oxo-1,2-dihydrobenzo[cd]indol-6-yl)-1,4-diazepan-1-yl]acetate;

6-[4-(cyclohexylmethyl)-1,4-diazepan-1-yl]-1-isopentylbenzo[cd]indol-2(1H)-one;

6-[4-(cyclopropylmethyl)-1,4-diazepan-1-yl]-1-isopentylbenzo[cd]indol-2(1H)-one;

1-isopentyl-6-(4-isopropyl-1,4-diazepan-1-yl)benzo[cd]indol-2(1H)-one;

1-isopentyl-6-[4-(2-nitrobenzyl)-1,4-diazepan-1-yl]benzo[cd]indol-2(1H)-one;

1-isopentyl-6-[4-(4-methoxybenzyl)-1,4-diazepan-1-yl]benzo[cd]indol-2(1H)-one;

1-butyl-6-(4-propyl-1,4-diazepan-1-yl)benzo[cd]indol-2(1H)-one;

6-(4-allyl-1,4-diazepan-1-yl)-1-butylbenzo[cd]indol-2(1H)-one;

1-butyl-6-(4-pentyl-1,4-diazepan-1-yl)benzo[cd]indol-2(1H)-one;

1-butyl-6-(4-isobutyl-1,4-diazepan-1-yl)benzo[cd]indol-2(1H)-one;

1-butyl-6-(4-cyclohexyl-1,4-diazepan-1-yl)benzo[cd]indol-2(1H)-one;

1-butyl-6-[4-(2-phenylethyl)-1,4-diazepan-1-yl]benzo[cd]indol-2(1H)-one;

4-[4-(1-butyl-2-oxo-1,2-dihydrobenzo[cd]indol-6-yl)-1,4-diazepan-1-yl]butanenitrile;

1-butyl-6-[4-(3-phenylpropyl)-1,4-diazepan-1-yl]benzo[cd]indol-2(1H)-one;

1-butyl-6-[4-(cyclobutylmethyl)-1,4-diazepan-1-yl]benzo[cd]indol-2(1H)-one;

1-butyl-6-[4-(2-ethoxyethyl)-1,4-diazepan-1-yl]benzo[cd]indol-2(1H)-one;

1-butyl-6-(4-isopentyl-1,4-diazepan-1-yl)benzo[cd]indol-2(1H)-one;

benzyl [4-(1-butyl-2-oxo-1,2-dihydrobenzo[cd]indol-6-yl)-1,4-diazepan-1-yl]acetate;

1-butyl-6-(4-isopropyl-1,4-diazepan-1-yl)benzo[cd]indol-2(1H)-one;

1-butyl-6-[4-(2-nitrobenzyl)-1,4-diazepan-1-yl]benzo[cd]indol-2(1H)-one;

1-allyl-6-(4-propyl-1,4-diazepan-1-yl)benzo[cd]indol-2(1H)-one;

1-allyl-6-(4-butyl-1,4-diazepan-1-yl)benzo[cd]indol-2(1H)-one;

1-allyl-6-(4-allyl-1,4-diazepan-1-yl)benzo[cd]indol-2(1H)-one;

1-allyl-6-(4-pentyl-1,4-diazepan-1-yl)benzo[cd]indol-2 (1H)-one;

1-allyl-6-(4-isobutyl-1,4-diazepan-1-yl)benzo[cd]indol-2 (1H)-one;

1-allyl-6-[4-(3,3,3-trifluoropropyl)-1,4-diazepan-1-yl] benzo[cd]indol-2(1H)-one;

1-allyl-6-[4-(4,4,4-trifluorobutyl)-1,4-diazepan-1-yl] benzo[cd]indol-2(1H)-one;

1-allyl-6-[4-(2-phenylethyl)-1,4-diazepan-1-yl]benzo[cd] indol-2(1H)-one;

4-[4-(1-allyl-2-oxo-1,2-dihydrobenzo[cd]indol-6-yl)-1,4-diazepan-1-yl]butanenitrile;

1-allyl-6-[4-(cyclobutylmethyl)-1,4-diazepan-1-yl]benzo [cd]indol-2(1H)-one;

1-allyl-6-[4-(2-ethoxyethyl)-1,4-diazepan-1-yl]benzo[cd] indol-2(1H)-one; or 1-allyl-6-(4-isopentyl-1,4-diazepan-1-yl)benzo[cd]indol-2(1H)-one; or a pharmaceutically acceptable salt thereof.

19. The compound of claim 1 wherein X is C and Y is C=O or $CH_2$.

20. The compound of claim 19 wherein $R_2$, $R_3$, $R_4$, $R_5$ and $R_6$ are hydrogen.

21. The compound of claim 20 wherein each of $R_7$, $R_8$, $R_9$, $R_{10}$, $R_{12}$, $R_{13}$, $R_{14}$, $R_{15}$, $R_{16}$, and $R_{17}$ are hydrogen.

22. The compound of claim 21 wherein $R_1$ and $R_{1a}$ are independently selected from hydrogen; an unsubstituted linear or branched saturated $C_1$ to $C_6$ alkyl group; an unsubstituted $C_3$ to $C_6$ cycloalkyl group; a $C_3$ to $C_6$ cycloalkyl group substituted with one to three $C_1$ to $C_3$ alkyl groups; an unsubstituted phenyl $C_1$ to $C_3$ alkyl group; or a phenyl $C_1$ to $C_3$ alkyl group substituted with one to three $C_1$ to $C_3$ alkoxy groups; or $R_1$, and $R_{1a}$ may form together with the carbon atom to which they are attached a $C_4$ to $C_6$ cycloalkyl group in spiro form.

23. The compound of claim 22 wherein $R_1$ and $R_{1a}$ are independently selected from methyl, ethyl, propyl, butyl, pentyl, hexyl, benzyl, cyclobutyl, cyclopentyl, cyclohexyl, cyclopropylmethyl, cyclobutylmethyl, or cyclohexylmethyl; or $R_1$ and $R_{1a}$ form together with the carbon atom to which they are attached cyclobutyl, cyclopentyl, cyclohexyl in spiro form.

24. The compound of claim 22 wherein $R_1$ and $R_{1a}$ are the same.

25. The compound of claim 21 wherein $R_{11}$ is selected from hydrogen; an unsubstituted linear or branched saturated $C_1$ to $C_6$ alkyl group; a $C_1$ to $C_6$ linear or branched saturated alkyl group substituted with one to three halogens; an unsubstituted $C_3$ to $C_6$ cycloalkyl group; a $C_3$ to $C_6$ cycloalkyl group substituted with one to three $C_1$ to $C_3$ alkyl groups; unsubstituted or substituted $C_3$ to $C_{10}$ alkenyl group; an unsubstituted phenyl $C_1$ to $C_3$ alkyl group; or a phenyl $C_1$ to $C_3$ alkyl group substituted with one to three $C_1$ to $C_3$ alkoxy groups or $C_1$ to $C_3$ halogenated alkoxy groups.

26. The compound of claim 25 wherein $R_{11}$ is selected from methyl, ethyl, propyl, butyl, pentyl, hexyl, trifluorobutyl, trifluoropropyl, benzyl, methoxybenzyl, trifluoromethoxybenzyl, phenylethyl, phenylpropyl, cyclopropylmethyl, cyclobutylmethyl, cyclohexylmethyl, cyclohexyl, allyl, methylallyl, or 3,7-dimethylocta-2,6-dienyl.

27. The compound of claim 21 wherein Y is C=O.

28. The compound of claim 19 selected from at least one of:

2,2-dimethyl-5-(4-methyl-1,4-diazepan-1-yl) acenaphthylen-1(2H)-one;

2,2-diethyl-5-(4-methyl-1,4-diazepan-1-yl) acenaphthylen-1(2H)-one;

5-(4-methyl-1,4-diazepan-1-yl)-2,2-dipropylacenaphthylen-1(2H)-one;

2,2-dibutyl-5-(4-methyl-1,4-diazepan-1-yl) acenaphthylen-1(2H)-one;

5-(4-methyl-1,4-diazepan-1-yl)-2,2-dipentylacenaphthylen-1(2H)-one;

2,2-dibenzyl-5-(4-methyl-1,4-diazepan-1-yl) acenaphthylen-1(2H)-one;

Spiro{cyclopentane-1,2'-[5'-(4"-methyl-1",4"-diazepan-1"-yl)-acenaphthylen-1'(2'H)-one]};

5-(4-ethyl-1,4-diazepan-1-yl)-2,2-dimethylacenaphthylen-1(2H)-one;

2,2-diethyl-5-(4-ethyl-1 4-diazepan-1-yl)acenaphthylen-1(2H)-one;

5-(4-ethyl-1,4-diazepan-1-yl)-2,2-dipropylacenaphthylen-1(2H)-one;

2,2-dibutyl-5-(4-ethyl-1,4-diazepan-1-yl)acenaphthylen-1(2H)-one;

5-(4-ethyl-1,4-diazepan-1-yl)-2,2-dipentylacenaphthylen-1(2H)-one;

2,2-dibenzyl-5-(4-ethyl-1,4-diazepan-1-yl) acenaphthylen-1(2H)-one;

Spiro{cyclobutane-1,2'-[5'-(4"-ethyl-1",4"-diazepan-1"-yl)-acenaphthylen-1'(2'H)-one]};

Spiro{cyclopentane-1,2'-[5'-(4"-ethyl-1",4"-diazepan-1"-yl)-acenaphthylen-1'(2'H)-one]};

Spiro{cyclohexane-1,2'-[5'-(4"-ethyl-1",4"-diazepan-1"-yl)-acenaphthylen-1'(2'H)-one]};

2,2-dimethyl-5-(4-propyl-1,4-diazepan-1-yl) acenaphthylen-1(2H)-one;

2,2-diethyl-5-(4-propyl-1,4-diazepan-1-yl) acenaphthylen-1(2H)-one;

2,2-dipropyl-5-(4-propyl-1,4-diazepan-1-yl) acenaphthylen-1(2H)-one;

2,2-dibutyl-5-(4-propyl-1,4-diazepan-1-yl) acenaphthylen-1(2H)-one;

2,2-dipentyl-5-(4-propyl-1,4-diazepan-1-yl) acenaphthylen-1(2H)-one;

2,2-dibenzyl-5-(4-propyl-1,4-diazepan-1-yl) acenaphthylen-1(2H)-one;

Spiro{cyclobutane-1,2'-[5'-(4"-propyl-1,4"-diazepan-1"-yl)-acenaphthylen-1'(2'H)-one]};

Spiro{cyclopentane-1,2'-[5'-(4"-propyl-1",4"-diazepan-1"-yl)-acenaphthylen-1'(2'H)-one]};

Spiro{cyclohexane-1,2'-[5'-(4"-propyl-1",4"-diazepan-1"-yl)-acenaphthylen-1'(2'H)-one]};

5-(4-allyl-1,4-diazepan-1-yl)-2,2-dimethylacenaphthylen-1(2H)-one;

5-(4-allyl-1,4-diazepan-1-yl)-2,2-diethylacenaphthylen-1(2H)-one;

5-(4-allyl-1,4-diazepan-1-yl)-2,2-dipropylacenaphthylen-1(2H)-one;

5-(4-allyl-1,4-diazepan-1-yl)-2,2-dibutylacenaphthylen-1(2H)-one;

5-(4-allyl-1,4-diazepan-1-yl)-2,2-dipentylacenaphthylen-1(2H)-one;

5-(4-allyl-1,4-diazepan-1-yl)-2,2-dibenzylacenaphthylen-1(2H)-one;

Spiro{cyclobutane-1,2'-[5'-(4"-allyl-1",4"-diazepan-1"-yl)-acenaphthylen-1'(2'H)-one]};

Spiro{cyclopentane-1,2'-[5'-(4"-allyl-1",4"-diazepan-1"-yl)-acenaphthylen-1'(2'H)-one]};

Spiro{cyclohexane-1,2'-[5'-(4"-allyl-1",4"-diazepan-1"-yl)-acenaphthylen-1'(2'H)-one]};

5-(4-butyl-1,4-diazepan-1-yl)-2,2-dimethylacenaphthylen-1(2H)-one;

5-(4-butyl-1,4-diazepan-1-yl)-2,2-diethylacenaphthylen-1(2H)-one;

5-(4-butyl-1,4-diazepan-1-yl)-2,2-dipropylacenaphthylen-1(2H)-one;

2,2-dibutyl-5-(4-butyl-1,4-diazepan-1-yl)acenaphthylen-1(2H)-one;

5-(4-butyl-1,4-diazepan-1-yl)-2,2-dipentylacenaphthylen-1(2H)-one;

2,2-dibenzyl-5-(4-butyl-1,4-diazepan-1-yl)acenaphthylen-1(2H)-one;

Spiro{cyclobutane-1,2'-[5'-(4"-butyl-1",4"-diazepan-1"-yl)-acenaphthylen-1'(2'H)-one]};

Spiro{cyclopentane-1,2'-[5'-(4"-butyl-1",4"-diazepan-1"-yl)-acenaphthylen-1'(2'H)-one]};

Spiro{cyclohexane-1,2'-[5'-(4"-butyl-1",4"-diazepan-1"-yl)-acenaphthylen-1'(2'H)-one]};

2,2-dimethyl-5-(4-pentyl-1,4-diazepan-1-yl)acenaphthylen-1(2H)-one;

2,2-diethyl-5-(4-pentyl-1,4-diazepan-1-yl)acenaphthylen-1(2H)-one;

5-(4-pentyl-1,4-diazepan-1-yl)-2,2-dipropylacenaphthylen-1(2H)-one;

2,2-dibutyl-5-(4-pentyl-1,4-diazepan-1-yl)acenaphthylen-1(2H)-one;

2,2-dipentyl-5-(4-pentyl-1,4-diazepan-1-yl)acenaphthylen-1(2H)-one;

2,2-dibenzyl-5-(4-pentyl-1,4-diazepan-1-yl)acenaphthylen-1(2H)-one;

Spiro{cyclobutane-1,2'-[5'-(4"-pentyl-1",4"-diazepan-1"-yl)-acenaphthylen-1'(2'H)-one]};

Spiro{cyclopentane-1,2'-[5'-(4"-pentyl-1",4"-diazepan-1"-yl)-acenaphthylen-1'(2'H)-one]};

Spiro{cyclohexane-1,2'-[5'-(4"-pentyl-1",4"-diazepan-1"-yl)-acenaphthylen-1'(2'H)-one]};

2,2-dimethyl-5-(4-neopentyl-1,4-diazepan-1-yl)acenaphthylen-1(2H)-one;

5-(4-neopentyl-1,4-diazepan-1-yl)-2,2-dipentylacenaphthylen-1(2H)-one;

Spiro{cyclobutane-1,2'[5'(4"-neopentyl-1",4"-diazepan-1"-yl)-acenapthylen-1'(2'H)-one]};

2,2-dimethyl-5-[4-(4,4,4-trifluorobutyl)-1,4-diazepan-1-yl]acenaphthylen-1(2H)-one;

2,2-diethyl-5-[4-(4,4,4-trifluorobutyl)-1,4-diazepan-1-yl]acenaphthylen-1(2H)-one;

2,2-dipropyl-5-[4-(4,4,4-trifluorobutyl)-1,4-diazepan-1-yl]acenaphthylen-1(2H)-one;

2,2-dibutyl-5-[4-(4,4,4-trifluorobutyl)-1,4-diazepan-1-yl]acenaphthylen-1(2H)-one;

2,2-dipentyl-5-[4-(4,4,4-trifluorobutyl)-1,4-diazepan-1-yl]acenaphthylen-1(2H)-one;

2,2-dibenzyl-5-[4-(4,4,4-trifluorobutyl)-1,4-diazepan-1-yl]acenaphthylen-1(2H)-one;

Spiro{cyclobutane-1,2'-[5'-(4"-(4,4,4-trifluorobutyl)-1",4"-diazepan-1"-yl)-acenaphthylen-1'(2'H)-one]};

Spiro{cyclopentane-1,2'-[5'-(4"-(4,4,4-trifluorobutyl)-1",4"-diazepan-1"-yl)-acenaphthylen-1'(2'H)-one]};

Spiro{cyclohexane-1,2'-[5'-(4"-(4,4,4-trifluorobutyl)-1",4"-diazepan-1"-yl)-acenaphthylen-1'(2'H)-one]};

2,2-dimethyl-5-[4-(3,3,3-trifluoropropyl)-1,4-diazepan-1-yl]acenaphthylen-1(2H)-one;

2,2-diethyl-5-[4-(3,3,3-trifluoropropyl)-1,4-diazepan-1-yl]acenaphthylen-1(2H)-one;

2,2-dipropyl-5-[4-(3 ,3,3-trifluoropropyl)-1,4-diazepan-1-yl]acenaphthylen-1(2H)-one;

2,2-dibutyl-5-[4-(3,3,3-trifluoropropyl)-1,4-diazepan-1-yl]acenaphthylen-1(2H)-one;

2,2-dipentyl-5-[4-(3,3,3-trifluoropropyl)-1,4-diazepan-1-yl]acenaphthylen-1(2-one;

2,2-dibenzyl-5-[4-(3,3,3-trifluoropropyl)-1,4-diazepan-1-yl]acenaphthylen-1(2H)-one;

Spiro{cyclobutane-1,2'-[5'-(4"-(3,3,3-trifluoropropyl)-1",4"-diazepan-1"-yl)-acenaphthylen-1'(2'H)-one]};

Spiro{cyclopentane-1,2'-[5'-(4"-(3,3,3-trifluoropropyl)-1",4"-diazepan-1"-yl)-acenaphthylen-1'(2'H)-one]};

Spiro{cyclohexane-1,2'-[5'-(4"-(3,3,3-trifluoropropyl)-1",4"-diazepan-1"-yl)-acenaphthylen-1'(2'H)-one]};

2,2-dimethyl-5-[4-(2-methylprop-2-enyl)-1,4-diazepan-1-yl]acenaphthylen-1(2H)-one;

2,2-diethyl-5-[4-(2-methylprop-2-enyl)-1,4-diazepan-1-yl]acenaphthylen-1(1H)-one;

5-[4-(2-methylprop-2-enyl)-1,4-diazepan-1-yl]-2,2-dipropylacenaphthylen-1(2H)-one;

2,2-dibutyl-5-[4-(2-methylprop-2-enyl)-1,4-diazepan-1-yl]acenaphthylen-1(2H)-one;

5-[4-(2-methylprop-2-enyl)-1,4-diazepan-1-yl]-2,2-dipentylacenaphthylen-1(2H)-one;

2,2-dibenzyl-5-[4-(2-methylprop-2-enyl)-1,4-diazepan-1-yl]acenaphthylen-1(2H)-one;

Spiro{cyclobutane-1,2'-[5'-(4"-(2-methylallyl)-1",4"-diazepan-1"-yl)-acenaphthylen-1'(2'H)-one]};

Spiro{cyclopentane-1,2'-[5'-(4"-(2-methylallyl)-1",4"-diazepan-1"-yl)-acenaphthylen-1'(2'H)-one]};

Spiro{cyclohexane-1,2'-[5'-(4"-(2-methylallyl)-1",4"-diazepan-1"-yl)-acenaphthylen-1'(2'H)-one]};

5-(4-isopropyl-1,4-diazepan-1-yl)-2,2-dipropylacenaphthylen-1(2H)-one;

2,2-dibutyl-5-(4-isopropyl-1,4-diazepan-1-yl)acenaphthylen-1(2H)-one;

5-(4-isopropyl-1,4-diazepan-1-yl)-2,2-dipentylacenaphthylen-1(2H)-one;

2,2-dibenzyl-5-(4-isopropyl-1,4-diazepan-1-yl)acenaphthylen-1(2H)-one;

Spiro{cyclobutane-1,2'-[5'-(4"-(1-methylethyl)-1",4"-diazepan-1"-yl)-acenaphthylen-1'(2'H)-one]};

Spiro{cyclopentane-1,2'-[5'-(4"-(1-methylethyl)-1",4"-diazepan-1"-yl)-acenaphthylen-1'(2'H)-one]};

Spiro{cyclohexane-1,2'-[5'-(4"-(1-methylethyl)-1",4"-diazepan-1"-yl)-acenaphthylen-1'(2'H)-one]};

5-(4-isobutyl-1,4-diazepan-1-yl)-2,2-dimethylacenaphthylen-1(2H)-one;

2,2-diethyl-5-(4-isobutyl-1,4-diazepan-1-yl)acenaphthylen-1(2H)-one;

5-(4-isobutyl-1,4-diazepan-1-yl)-2,2-dipropylacenaphthylen-1(2H)-one;

2,2-dibutyl-5-(4-isobutyl-1,4-diazepan-1-yl)acenaphthylen-1(2H)-one;

5-(4-isobutyl-1,4-diazepan-1-yl)-2,2-dipentylacenaphthylen-1(2H)-one, 2,2-dibenzyl-5-(4-isobutyl-1,4-diazepan-1-yl)acenaphthylen-1(2H)-one;

Spiro{cyclobutane-1,2'-[5'-(4''-(2-methylpropyl)-1'',4''-diazepan-1''-yl)-acenaphthylen-1'(2'H)-one]};

Spiro{cyclopentane-1,2'-[5'-(4''-(2-methylpropyl)-1'',4''-diazepan-1''-yl)-acenaphthylen-1'(2'H)-one]};

5-(4-isopentyl-1,4-diazepan-1-yl)-2,2-dimethylacenaphthylen-1(2H)-one;

2,2-diethyl-5-(4-isopentyl-1,4-diazepan-1-yl)acenaphthylen-1(2H)-one;

5-(4-isopentyl-1,4-diazepan-1-yl)-2,2-dipropylacenaphthylen-1(2H)-one;

2,2-dibutyl-5-(4-isopentyl-1,4-diazepan-1-yl)acenaphthylen-1(2H)-one;

5-(4-isopentyl-1,4-diazepan-1-yl)-2,2-dipentylacenaphthylen-1(2H)-one;

2,2-dibenzyl-5-(4-isopentyl-1,4-diazepan-1-yl)acenaphthylen-1(2H)-one;

Spiro{cyclobutane-1,2'-[5'-(4''-(3-methylbutyl)-1'',4''-diazepan-1''-yl)-acenaphthylen-1'(2'H)-one]};

Spiro{cyclopentane-1,2'-[5'-(4''-(3-methylbutyl)-1'',4''-diazepan-1''-yl)-acenaphthylen-1'(2'H)-one]}; or Spiro{cyclohexane-1,2'-[5'-(4''-(3-methylbutyl)-1'',4''-diazepan-1''-yl)-acenaphthylen-1'(2'H)-one]}; or a pharmaceutically acceptable salt thereof.

29. The compound of claim 19 selected from at least one of:

2,2-dimethyl-5-{4-[4-(trifluoromethoxy)benzyl]-1,4-diazepan-1-yl}acenaphthylen-1(2H)-one;

2,2-diethyl-5-{4-[4-(trifluoromethoxy)benzyl]-1,4-diazepan-1-yl}acenaphthylen-1(2H)-one;

2,2-dipropyl-5-{4-[4-(trifluoromethoxy)benzyl]-1,4-diazepan-1-yl}acenaphthylen-1(2H)-one;

2,2-dibutyl-5-{4-[4-(trifluoromethoxy)benzyl]-1,4-diazepan-1-yl}acenaphthylen-1(2H)-one;

2,2-dipentyl-5-{4-[4-(trifluoromethoxy)benzyl]-1,4-diazepan-1-yl}acenaphthylen-1(2H)-one;

2,2-dibenzyl-5-{4-[4-(trifluoromethoxy)benzyl]-1,4-diazepan-1-yl}acenaphthylen-1(2H)-one;

Spiro{cyclobutane-1,2'-[5'-(4''-(4-trifluoromethoxybenzyl)-1'',4''-diazepan-1''-yl)-acenaphthylen-1'(2'H)-one]};

Spiro{cyclopentane-1,2'-[5'-(4''-(4-tifluoromethylbenzyl)-1'',4''-diazepan-1''-yl)-acenaphthylen-1'(2'H)-one]};

Spiro{cyclohexane-1,2'-[5'-(4''-(4-trifluoromethoxybenzyl)-1'',4''-diazepan-1''-yl)-acenaphthylen-1'(2'H)-one]};

5-(4-benzyl-1,4-diazepan-1-yl)-2,2-dimethylacenaphthylen-1(2H)-one;

5-(4-benzyl-1,4-diazepan-1-yl)-2,2-diethylacenaphthylen-1(2H)-one;

5-(4-benzyl -1,4-diazepan-1-yl)-2,2-dipropylacenaphthylen-1(2H)-one;

5-(4-benzyl -1,4-diazepan-1-yl)-2,2-dibutylacenaphthylen-1(2H)-one;

5-(4-benzyl-1,4-diazepan-1-yl)-2,2-dipentylacenaphthylen-1(2H)-one;

2,2-dibenzyl-5-(4-benzyl-1,4-diazepan-1-yl)acenaphthylen-1(2H)-one;

Spiro{cyclobutane-1,2'-[5'-(4''-benzyl-1'',4''-diazepan-1''-yl)-acenaphthylen-1'(2'H)-one]};

Spiro{cyclopentane-1,2'-[5'-(4''-benzyl-1'',4''-diazepan-1''-yl)-acenaphthylen-1'(2'H)-one]};

Spiro{cyclohexane-1,2'-[5'-(4''-benzyl-1'',4''-diazepan-1''-yl)-acenaphthylen-1'(2'H)-one]};

2,2-dimethyl-5-[4-(3-phenylpropyl)-1,4-diazepan-1-yl]acenaphthylen-1(2H)-one;

2,2-diethyl-5-[4-(3-phenylpropyl)-1,4-diazepan-1-yl]acenaphthylen-1(2H)-one;

5-[4-(3-phenylpropyl)-1,4-diazepan-1-yl]-2,2-dipropylacenaphthylen-1(2H)-one;

2,2-dibutyl-5-[4-(3-phenylpropyl)-1,4-diazepan-1-yl]acenaphthylen-1(2H)-one;

2,2-dipentyl-5-[4-(3-phenylpropyl)-1,4-diazepan-1-yl]acenaphthylen-1(2H)-one;

2,2-dibenzyl-5-[4-(3-phenylpropyl)-1,4-diazepan-1-yl]acenaphthylen-1(2H)-one;

Spiro{cyclobutane-1,2'-[5'-(4''-(3-phenylpropyl)-1'',4''-diazepan-1''-yl)-acenaphthylen-1'(2'H)-one]};

Spiro{cyclopentane-1,2'-[5'-(4''-(3-phenylpropyl)-1'',4''-diazepan-1''-yl)-acenaphthylen-1'(2'H)-one]};

Spiro{cyclohexane-1,2'-[5'-(4''-(3-phenylpropyl)-1'',4''-diazepan-1''-yl)-acenaphthylen-1'(2'H)-one]};

2,2-dimethyl-5-[4-(2-phenylethyl)-1,4-diazepan-1-yl]acenaphthylen-1(2H)-one;

2,2-diethyl-5-[4-(2-phenylethyl)-1,4-diazepan-1-yl]acenaphthylen-1(2H)-one;

5-[4-(2-phenylethyl)-1,4-diazepan-1-yl]-2,2-dipropylacenaphthylen-1(2H)-one;

2,2-dibutyl-5-[4-(2-phenylethyl)-1,4-diazepan-1-yl]acenaphthylen-1(21)-one;

2,2-dipentyl-5-[4-(2-phenylethyl)-1,4-diazepan-1-yl]acenaphthylen-1(2H)-one;

2,2-dibenzyl-5-[4-(2-phenylethyl)-1,4-diazepan-1-yl]acenaphthylen-1(2H)-one;

Spiro{cyclobutane-1,2'-[5'-(4''-(2-phenylethyl)-1'',4''-diazepan-1''-yl)-acenaphthylen-1'(2'H)-one]};

Spiro{cyclopentane-1,2'-[5'-(4''-(2-phenylethyl)-1'',4''-diazepan-1''-yl)-acenaphthylen-1'(2'H)-one]}; or Spiro{cyclohexane-1,2'-[5'-(4''-(2-phenylethyl)-1'',4''-diazepan-1''-yl)-acenaphthylen-1'(2'H)-one]}; or a pharmaceutically acceptable salt thereof.

30. The compound of claim 19 selected from at least one of

5-[4-(cyclohexylmethyl)-1,4-diazepan-1-yl]-2,2-dimethylacenaphthylen-1(2H)-one;

5-[4-(cyclohexylmethyl)-1,4-diazepan-1-yl]-2,2-dipropylacenaphthylen-1(2H)-one;

2,2-dibutyl-5-[4-(cyclohexylmethyl)-1,4-diazepan-1-yl]acenaphthylen-1(2H)-one;

5-[4-(cyclohexylmethyl)-1,4-diazepan-1-yl]-2,2-dipentylacenaphthylen-1(2H)-one;

2,2-dibenzyl-5-[4-(cyclohexylmethyl)-1,4-diazepan-1-yl]acenaphthylen-1(2H)-one;

Spiro{cyclobutane-1,2'-[5'-(4''-cyclohexylmethyl-1'',4''-diazepan-1''-yl)-acenaphthylen-1'(2'H)-one]};

5-[4-(cyclopropylmethyl)-1,4-diazepan-1-yl]-2,2-dimethylacenaphthylen-1(2H)-one;

5-[4-(cyclopropylmethyl)-1,4-diazepan-1-yl]-2,2-diethylacenaphthylen-1(2H)-one;

5-[4-(cyclopropylmethyl)-1,4-diazepan-1-yl]-2,2-dipropylacenaphthylen-1(2H)-one;

2,2-dibutyl-5-[4-(cyclopropylmethyl)-1,4-diazepan-1-yl]acenaphthylen-1(2H)-one;

5-[4-(cyclopropylmethyl)-1,4-diazepan-1-yl]-2,2-dipentylacenaphthylen-1(2H)-one;

2,2-dibenzyl-5-[4-(cyclopropylmethyl)-1,4-diazepan-1-yl]acenaphthylen-1(2H)-one;

Spiro{cyclobutane-1,2'-[5'-(4"-cyclopropyl-1",4"-diazepan-1"-yl)-acenaphthylen-1'(2'H)-one]};

Spiro{cyclopentane-1,2'-[5'-(4"-cyclopropy-1",4"-diazepan-1"-yl)-acenaphthylen-1'(2'H)-one]};

Spiro{cyclohexane-1,2'-[5'-(4"-cyclopropyl-1",4"-diazepan-1"-yl)-acenaphthylen-1'(2'H)-one]};

5-[4-(cyclobutylmethyl)-1,4-diazepan-1-yl]-2,2-dimethylacenaphthylen-1(2H)-one;

5-[4-(cyclobutylmethyl)-1,4-diazepan-1-yl]-2,2-diethylacenaphthylen-1(2H)-one;

5-[4-(cyclobutylmethyl)-1,4-diazepan-1-yl]-2,2-dipropylacenaphthylen-1(2H)-one;

2,2-dibutyl-5-[4-(cyclobutylmethyl)-1,4-diazepan-1-yl]acenaphthylen-1(2H)-one;

5-[4-(cyclobutylmethyl)-1,4-diazepan-1-yl]-2,2-dipentylacenaphthylen-1(2H)-one;

Spiro{cyclobutane-1,2'-[5'-(4"-cyclobutylmethyl-1",4"-diazepan-1"-yl)-acenaphthylen-1'(2'H)-one]};

Spiro{cyclopentane-1,2'-[5'-(4"-cyclobutylmethyl-1",4"-diazepan-1"-yl)-acenaphthylen-1'(2'H)-one]}; or Spiro{cyclo hexane-1,2'-[5'-(4"-cyclobutylmethyl-1",4"-diazepan-1"-yl)-acenaphthylen-1'(2'H)-one]}; or a pharmaceutically acceptable salt thereof.

31. The compound of claim 1 wherein X is N and Y is SO or $SO_2$.

32. The compound of claim 31 wherein $R_2$, $R_3$, $R_4$, $R_5$ and $R_6$ are hydrogen.

33. The compound of claim 32 wherein each of $R_7$, $R_8$, $R_9$, $R_{10}$, $R_{12}$, $R_{13}$, $R_{14}$, $R_{15}$, $R_{16}$, and $R_{17}$ are hydrogen.

34. The compound of claim 33 wherein $R_1$ is hydrogen; an unsubstituted linear or branched saturated $C_1$ to $C_6$ alkyl group; a $C_1$ to $C_6$ linear or branched saturated alkyl group substituted with one to three halogens; an unsubstituted $C_3$ to $C_6$ cycloalkyl group; a $C_3$ to $C_6$ cycloalkyl group substituted with one to three $C_1$ to $C_3$ alkyl groups; a unsubstituted or substituted $C_3$ to $C_{10}$ alkenyl group; an unsubstituted phenyl $C_1$ to $C_3$ alkyl group; or a phenyl $C_1$ to $C_3$ alkyl group substituted with one to three $C_1$ to $C_3$ alkoxy groups.

35. The compound of claim 34 wherein $R_1$ is selected from methyl, ethyl, propyl, butyl, pentyl, hexyl, trifluorobutyl, trifluoropropyl, benzyl, methoxybenzyl, phenylethyl, phenylpropyl, cyclopropylmethyl, cyclobutylmethyl, cyclohexylmethyl, or allyl.

36. The compound of claim 33 wherein $R_{11}$ is selected from hydrogen; an unsubstituted linear or branched saturated $C_1$ to $C_6$ alkyl group; a $C_1$ to $C_6$ linear or branched saturated alkyl group substituted with one to three halogens, $C_1$ to $C_3$ alkoxy groups, CN, COOalkyl, COOaryl or combinations thereof; an unsubstituted $C_3$ to $C_6$ cycloalkyl group; a $C_3$ to $C_6$ cycloalkyl group substituted with one to three $C_1$ to $C_3$ alkyl groups; a unsubstituted or substituted $C_3$ to $C_{10}$ alkenyl group; an unsubstituted phenyl $C_1$ to $C_3$ alkyl group; or a phenyl $C_1$ to $C_3$ alkyl group substituted with one to three $NO_2$ groups, $C_1$ to $C_3$ alkoxy groups, or $C_1$ to $C_3$ halogenated alkoxy groups.

37. The compound of claim 36 wherein $R_{11}$ is selected from hydrogen, methyl, ethyl, propyl, butyl, pentyl, hexyl, trifluorobutyl, trifluoropropyl, benzyl, methoxybenzyl, trifluoromethoxybenzyl, nitrobenzyl, phenylethyl, phenylpropyl, cyclopropylmethyl, cyclobutylmethyl or cyclohexylmethyl.

38. The compound of claim 31 wherein Y is $SO_2$.

39. The compound of claim 31 selected from at least one of:

2-methyl-5-(4-methyl-1,4-diazepan-1-yl)-2H-naphtho[1,8-cd]isothiazole 1,1-dioxide;

5-(4-ethyl-1,4-diazepan-1-yl)-2-methyl-2H-naphtho[1,8-cd]isothiazole 1,1-dioxide;

2-methyl-5-(4-propyl-1,4-diazepan-1-yl)-2H-naphtho[1,8-cd]isothiazole 1,1-dioxide;

5-(4-butyl-1,4-diazepan-1-yl)-2-methyl-2H-naphtho[1,8-cd]isothiazole 1,1-dioxide;

2-methyl-5-(4-neopentyl-1,4-diazepan-1-yl)-2H-naphtho[1,8-cd]isothiazole 1,1-dioxide;

5-(4-benzyl-1,4-diazepan-1-yl)-2-methyl-2H-naphtho[1,8-cd]isothiazole 1,1-dioxide;

2-methyl-5-[4-(2-phenylethyl)-1,4-diazepan-1-yl]-2H-naphtho[1,8-cd]isothiazole 1,1-dioxide;

5-(1,4-diazepan-1-yl)-2-methyl-2H-naphtho[1,8-cd]isothiazole 1,1-dioxide;

2-ethyl-5-(4-methyl-1,4-diazepan-1-yl)-2H-naphtho[1,8-cd]isothiazole 1,1-dioxide;

2-ethyl-5-(4-ethyl-1,4-diazepan-1-yl)-2H-naphtho[1,8-cd]isothiazole 1,1-dioxide;

2-ethyl-5-(4-propyl-1,4-diazepan-1-yl)-2H-naphtho[1,8-cd]isothiazole 1,1-dioxide;

5-(4-butyl-1,4-diazepan-1-yl)-2-ethyl-2H-naphtho[1,8-cd]isothiazole 1,1-dioxide;

2-ethyl-5-(4-neopentyl-1,4-diazepan-1-yl)-2H-naphtho[1,8-cd]isothiazole 1,1-dioxide;

5-(4-benzyl-1,4-diazepan-1-yl)-2-ethyl-2H-naphtho[1,8-cd]isothiazole 1,1-dioxide;

2-ethyl-5-[4-(2-phenylethyl)-1,4-diazepan-1-yl]-2H-naphtho[1,8-cd]isothiazole 1,1-dioxide;

5-(1,4-diazepan-1-yl)-2-ethyl-2H-naphtho[1,8-cd]isothiazole 1,1-dioxide;

5-(4-methyl-1,4-diazepan-1-yl)-2-propyl-2H-naphtho[1,8-cd]isothiazole 1,1-dioxide;

5-(4-ethyl-1,4-diazepan-1-yl)-2-propyl-2H-naphtho[1,8-cd]isothiazole 1,1-dioxide;

2-propyl-5-(4-propyl-1,4-diazepan-1-yl)-2H-naphtho[1,8-cd]isothiazole 1,1-dioxide;

5-(4-butyl-1,4-diazepan-1-yl)-2-propyl-2H-naphtho[1,8-cd]isothiazole 1,1-dioxide 5-(4-neopentyl-1,4-diazepan-1-yl)-2-propyl-2H-naphtho[1,8-cd]isothiazole 1,1-dioxide;

5-(4-benzyl-1,4-diazepan-1-yl)-2-propyl-2H-naphtho[1,8-cd]isothiazole 1,1-dioxide;

5-[4-(2-phenylethyl)-1,4-diazepan-1-yl]-2-propyl -2H-naphtho[1,8-cd]isothiazole 1,1-dioxide;

5-(1,4-diazepan-1-yl)-2-propyl-2H-naphtho[1,8-cd]isothiazole 1,1-dioxide;

5-(1,4-diazepan-1-yl)-2-isopropyl-2H-naphtho[1,8-cd]isothiazole 1,1-dioxide;

2-butyl-5-(1,4-diazepan-1-yl)-2H-naphtho[1,8-cd]isothiazole 1,1-dioxide;

5-(1,4-diazepan-1-yl)-2-hexyl-2H-naphtho[1,8-cd]isothiazole 1,1-dioxide;

2-isobutyl-5-(4-methyl-1,4-diazepan-1-yl)-2H-naphtho[1,8-cd]isothiazole 1,1-dioxide;

5-(4-ethyl-1,4-diazepan-1-yl)-2-isobutyl-2H-naphtho[1,8-cd]isothiazole 1,1-dioxide;

2-isobutyl-5-(4-propyl-1,4-diazepan-1-yl)-2H-naphtho[1,8-cd]isothiazole 1,1-dioxide;

5-(4-butyl-1,4-diazepan-1-yl)-2-isobutyl-2H-naphtho[1,8-cd]isothiazole 1,1-dioxide;

2-isobutyl-5-(4-neopentyl-1,4-diazepan-1-yl)-2H-naphtho[1,8-cd]isothiazole 1,1-dioxid 5-(4-benzyl-1,4-diazepan-1-yl)-2-isobutyl-2H-naphtho[1,8-cd]isothiazole 1,1-dioxide 2-isobutyl-5-[4-(2-phenylethyl)-1,4-diazepan-1-yl]-2H-naphtho[1,8-cd]isothiazole 1,1-dioxide;

5-(4-methyl-1,4-diazepan-1-yl)-2-pentyl-2H-naphtho[1,8-cd]isothiazole 1,1-dioxide;

5-(4-ethyl-1,4-diazepan-1-yl)-2-pentyl-2H-naphtho[1,8-cd]isothiazole 1,1-dioxide;

2-pentyl-5-(4-propyl-1,4-diazepan-1-yl)-2H-naphtho[1,8-cd]isothiazole 1,1-dioxide;

5-(4-benzyl-1,4-diazepan-1-yl)-2-pentyl-2H-naphtho[1,8-cd]isothiazole 1,1-dioxide;

2-pentyl-5-[4-(2-phenylethyl)-1,4-diazepan-1-yl]-2H-naphtho[1,8-cd]isothiazole 1,1dioxide; or 5-(1,4-diazepan-1-yl)-2-pentyl-2H-naphtho[1,8-cd]isothiazole 1,1-dioxide; or a pharmaceutically acceptable salt thereof.

40. The compound of claim 31 selected from at least one of:

5-(4-methyl-1,4-diazepan-1-yl)-2-(2-phenylethyl)-2H-naphtho[1,8-cd]isothiazole 1,1-dioxide;

5-(4-ethyl-1,4-diazepan-1-yl)-2-(2-phenylethyl)-2H-naphtho[1,8-cd]isothiazole 1,1-dioxide;

2-(2-phenylethyl)-5-(4-propyl-1,4-diazepan-1-yl)-2H-naphtho[1,8-cd]isothiazole 1,1-dioxide;

5-(4-butyl-1,4-diazepan-1-yl)-2-(2-phenylethyl)-2H-naphtho[1,8-cd]isothiazole 1,1-dioxide;

5-(4-neopentyl-1,4-diazepan-1-yl)-2-(2-phenylethyl)-2H-naphtho[1,8-cd]isothiazole 1,1-dioxide;

5-(4-benzyl-1,4-diazepan-1-yl)-2-(2-phenylethyl)-2H-naphtho[1,8-cd]isothiazole 1,1-dioxide;

2-(2-phenylethyl)-5-[4-(2-phenylethyl)-1,4-diazepan-1-yl]-2H-naphtho[1,8-cd]isothiazole 1,1-dioxide;

5-(4-methyl-1,4-diazepan-1-yl)-2-(3-phenylpropyl)-2H-naphtho[1,8-cd]isothiazole 1,1-dioxide;

5-(4-ethyl-1,4-diazepan-1-yl)-2-(3-phenylpropyl)-2H-naphtho[1,8-cd]isothiazole 1,1-dioxide;

2-(3-phenylpropyl)-5-(4-propyl-1,4-diazepan-1-yl)-2H-naphtho[1,8-cd]isothiazole 1,1-dioxide;

5-(4-butyl-1,4-diazepan-1-yl)-2-(3-phenylpropyl)-2H-naphtho[1,8-cd]isothiazole 1,1-dioxide;

5-(4-benzyl-1,4-diazepan-1-yl)-2-(3-phenylpropyl)-2H-naphtho[1,8-cd]isothiazole 1,1-dioxide;

5-[4-(2-phenylethyl)-1,4-diazepan-1-yl]-2-(3-phenylpropyl)-2H-naphtho[1,8-cd]isothiazole 1,1-dioxide;

2-(cyclohexylmethyl)-5-(4-methyl-1,4-diazepan-1-yl)-2H-naphtho[1,8-cd]isothiazole 1,1-dioxide;

2-(cyclohexylmethyl)-5-(4-propyl-1,4-diazepan-1-yl)-2H-naphtho[1,8-cd]isothiazole 1,1-dioxide;

5-(4-butyl-1,4-diazepan-1-yl)-2-(cyclohexylmethyl)-2H-naphtho[1,8-cd]isothiazole 1,1-dioxide;

2-(cyclohexylmethyl)-5-(4-neopentyl-1,4-diazepan-1-yl)-2H-naphtho[1,8-cd]isothiazole 1,1-dioxide;

5-(4-benzyl-1,4-diazepan-1-yl)-2-(cyclohexylmethyl)-2H-naphtho[1,8-cd]isothiazole 1,1-dioxide; or 2-(cyclohexylmethyl)-5-[4-(2-phenylethyl)-1,4-diazepan-1-yl]-2H-naphtho[1,8-cd]isothiazole 1,1-dioxide; or a pharmaceutically acceptable salt thereof.

41. The compound of claim 1 wherein X is C and Y is SO or $SO_2$.

42. The compound of claim 41 wherein $R_2$, $R_3$, $R_4$, $R_5$ and $R_6$ are hydrogen.

43. The compound of claim 42 wherein each of $R_7$, $R_8$, $R_9$, $R_{10}$, $R_{12}$, $R_{13}$, $R_{14}$, $R_{15}$, $R_{16}$, and $R_{17}$ are hydrogen.

44. The compound of claim 43 wherein $R_1$ and $R_{1a}$ are independently selected from hydrogen; an unsubstituted linear or branched saturated $C_1$ to $C_6$ alkyl group; an unsubstituted $C_3$ to $C_6$ cycloalkyl group; a $C_3$ to $C_6$ cycloalkyl group substituted with one to three $C_1$ to $C_3$ alkyl groups; an unsubstituted phenyl $C_1$ to $C_3$ alkyl group; or a phenyl $C_1$ to $C_3$ alkyl group substituted with one to three $C_1$ to $C_3$ alkoxy groups; or $R_1$ and $R_{1a}$ may form together with the carbon atom to which they are attached a $C_4$ to $C_6$ cycloalkyl group in spiro form.

45. The compound of claim 44 wherein $R_1$ and $R_{1a}$ are the same.

46. The compound of claim 43 wherein $R_{11}$ is selected from hydrogen; an unsubstituted linear or branched saturated $C_1$ to $C_6$ alkyl group; a $C_1$ to $C_6$ linear or branched saturated alkyl group substituted with one to three halogens; an unsubstituted $C_3$ to $C_6$ cycloalkyl group; a $C_3$ to $C_6$ cycloalkyl group substituted with one to three $C_1$ to $C_3$ alkyl groups; unsubstituted or substituted $C_3$ to $C_{10}$ alkenyl group; an unsubstituted phenyl $C_1$ to $C_3$ alkyl group; or a phenyl $C_1$ to $C_3$ alkyl group substituted with one to three $C_1$ to $C_3$ alkoxy groups or $C_1$ to $C_3$ halogenated alkoxy groups.

47. The compound of claim 43 wherein Y is $SO_2$.

48. A method for treating one or more conditions selected from schizophrenia, schizoaffective disorder, schizophreniform disorder; depressive disorders, eating disorders, obesity, or anxiety disorders or combinations thereof comprising:

administering to a mammal suffering from one or more of the conditions a pharmaceutically effective amount of at least one compound of claim 1.

49. A pharmaceutical composition comprising a pharmaceutically effective amount of at least one compound of claim 1 and at least one pharmaceutically acceptable carrier.

50. A compound of Formula (I) or a pharmaceutically acceptable salt thereof:

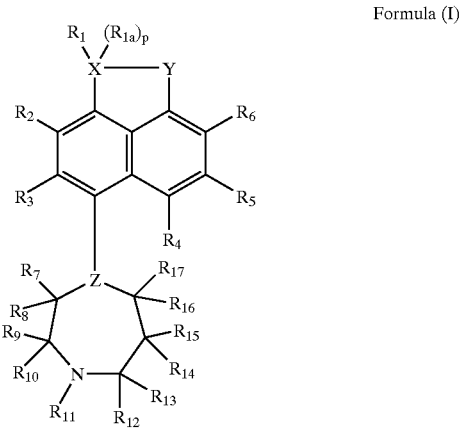

Formula (I)

wherein:

X is C or N;

Y is $CH_2$, C=O, S=O, or $SO_2$;

Z is C;

$R_1$, $R_{1a}$ and $R_{11}$ are each independently selected from hydrogen, an alkyl or alkenyl group, a $C_3$ to $C_8$ cycloalkyl group, or an arylalkyl or heteroarylalkyl group, or when X is C, $R_1$ and $R_{1a}$ may form together with the carbon atom to which they are attached a $C_3$ to $C_8$ cycloalkyl group in spiro form;

$R_2$, $R_3$, $R_4$, $R_5$ and $R_6$ are each independently selected from hydrogen, halogen, an alkyl, alkenyl, or alkynyl group, a $C_3$ to $C_8$ cycloalkyl group, or a cycloheteroalkyl, aryl, heteroaryl, arylalkyl, alkanoyl, CN, CHO, alkoxy, aryloxy, heteroaryloxy, alkenyloxy, alkynyloxy, OCOOalkyl, OCOOaryl, OCONR$_{18}$, COOH, COOalkyl, COOaryl, CONR$_{18}$R$_{19}$, CONHOH, NR$_{18}$R$_{19}$, SO$_2$NR$_{18}$R$_{19}$, NO$_2$, NH$_2$, or OH group, where $R_{18}$ and $R_{19}$ are independently selected from hydrogen, an alkyl, alkenyl, or alkynyl group, a $C_3$ to $C_8$ cycloalkyl group, or an aryl, heteroaryl, arylalkyl, perfluoroalkyl, COalkyl, COaryl, COheteroaryl, COOalkyl, COOaryl, COOheteroaryl, CONHalkyl, CON(alkyl)$_2$, CONHaryl, CONHheteroaryl, cycloheteroalkyl, S(O)$_m$-alkyl or S(O)$_m$-aryl group, where m is 0, 1 or 2;

$R_7$, $R_8$, $R_9$, $R_{10}$, $R_{12}$, $R_{13}$, $R_{14}$, $R_{15}$, $R_{16}$, and $R_{17}$ are each independently selected from hydrogen, an alkyl, alkenyl or alkynyl group, a $C_3$ to $C_8$ cycloalkyl group, or a cycloheteroalkyl, aryl, arylalkyl or heteroaryl group;

p is 1 when X is carbon, and p is zero when X is nitrogen;

wherein aryl is

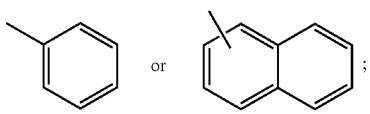

cycloheteroalkyl is

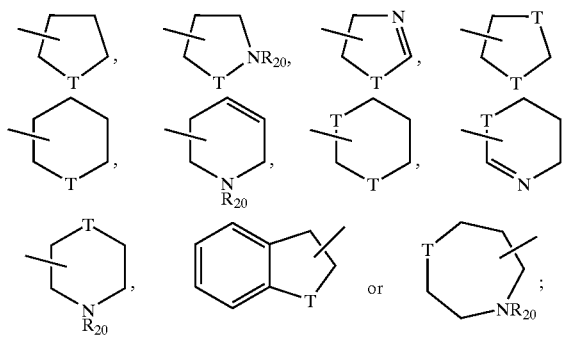

heteroaryl is

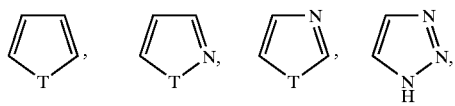

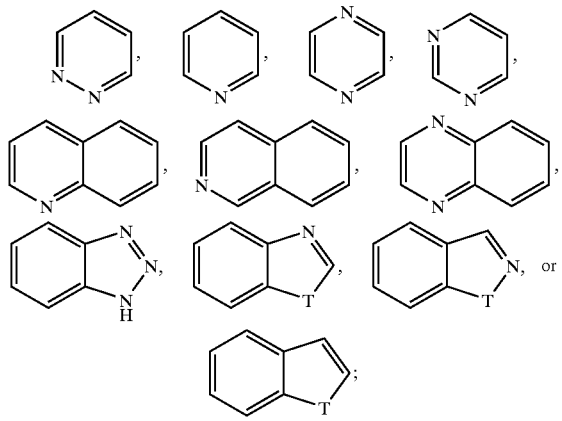

where a carbon of the cycloheteroalkyl may optionally be double bonded to either O or S where T is NR$_{18}$, O, or S, and where $R_{20}$ is hydrogen, halogen, an alkenyl or alkynyl group, a $C_3$ to $C_8$ cycloalkyl group, a cycloheteroalkyl, aryl, arylalkyl, heteroaryl, alkanoyl, CN, CHO, alkoxy, aryloxy, heteroaryloxy, alkenyloxy, alkynyloxy, OCOOalkyl, OCOOaryl, OCONR$_{18}$, COOH, COOalkyl, COOaryl, CONR$_{18}$R$_{19}$, CONHOH, NR$_{18}$R$_{19}$, SO$_2$NR$_{18}$R$_{19}$, NO$_2$, NH$_2$, OH, S(O)$_m$-alkyl or S(O)$_m$-aryl group, where the alkyl or alkoxy groups of $R_{20}$ may be optionally substituted with one or more halogens; and wherein any alkyl, alkenyl, alkynyl, aryl, arylalkyl, heteroaryl or cycloalkyl moiety of $R_1$, $R_{1a}$, or $R_2$ to $R_{17}$ may optionally be substituted with one to three groups independently selected from $R_{20}$ and where any cycloheteroaryl moiety of $R_1$, $R_{1a}$, or $R_2$ to $R_{17}$ may optionally be substituted with one to six groups independently selected from $R_{20}$.

51. The compound of claim 50 wherein $R_2$, $R_3$, $R_4$, $R_5$ and $R_6$ are hydrogen.

52. The compound of claim 51 wherein each of $R_7$, $R_8$, $R_9$, $R_{10}$, $R_{12}$, $R_{13}$, $R_{14}$, $R_{15}$, $R_{16}$, and $R_{17}$ are hydrogen.

53. A method for treating one or more conditions selected from schizophrenia, schizoaffective disorder, schizophreniform disorder, depressive disorders, eating disorders, obesity, or anxiety disorders, or combinations thereof comprising:

administering to a mammal suffering from one or more of the conditions a pharmaceutically effective amount of at least one compound of claim 50.

54. A pharmaceutical composition comprising a pharmaceutically effective amount of at least one compound of claim 50 and at least one pharmaceutically acceptable carrier.

* * * * *